Figure 4:
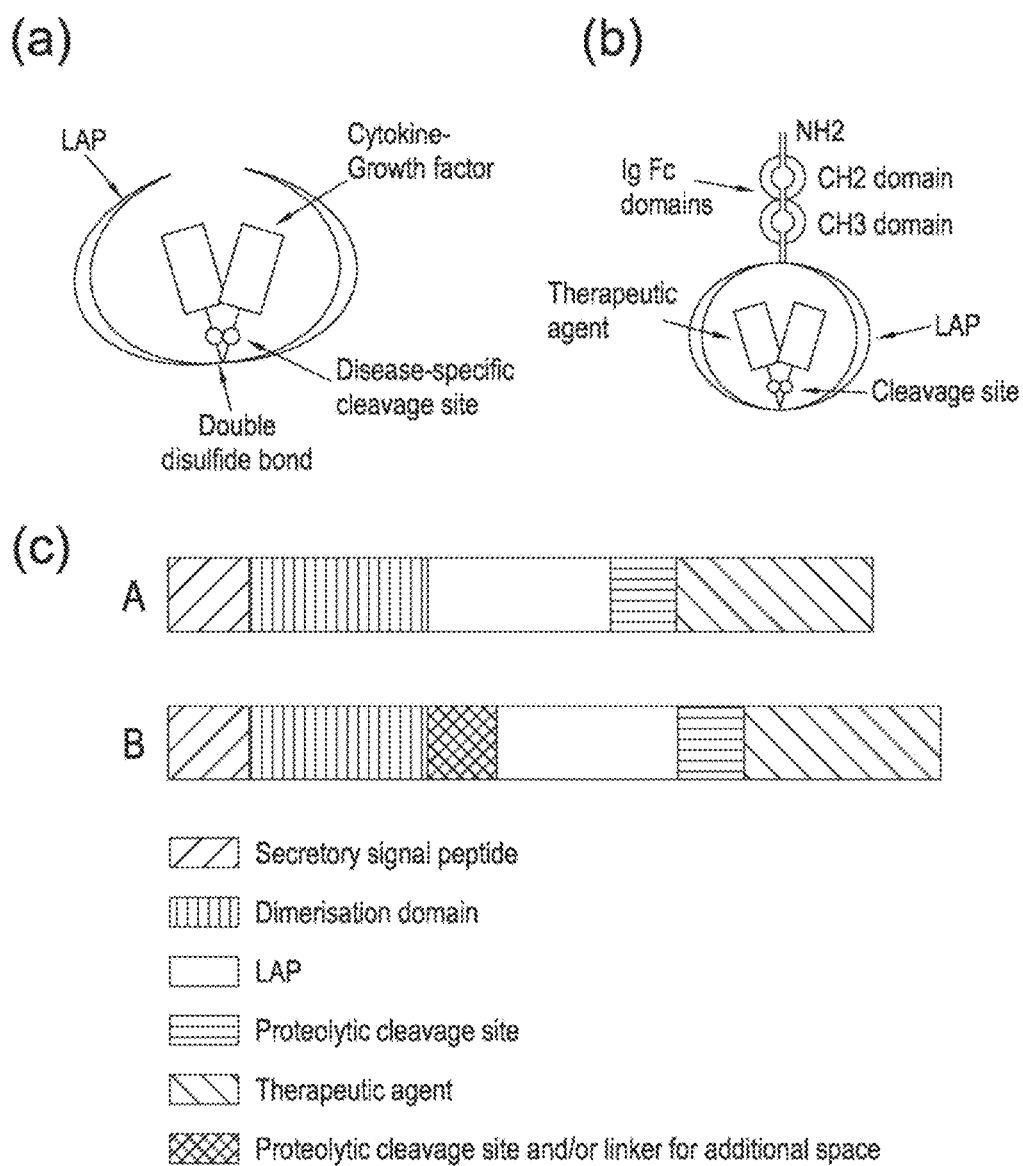

US010435451B2

(12) United States Patent
Chernajovsky et al.

(10) Patent No.: US 10,435,451 B2
(45) Date of Patent: Oct. 8, 2019

(54) MODIFIED LATENCY ASSOCIATED PROTEIN CONSTRUCT

(71) Applicant: Stealthyx Therapeutics Limited, Cambridge (GB)

(72) Inventors: Yuti Chernajovsky, London (GB); Lisa Mullen, London (GB); Gillian Adams, London (GB); David James Gould, London (GB); Hawzheen Muhammad, London (GB)

(73) Assignee: Stealthyx Therapeutics Limited, Cambridge (GB)

( * ) Notice: Subject to any disclaimer, the term of this patent is extended or adjusted under 35 U.S.C. 154(b) by 0 days.

(21) Appl. No.: 15/322,129

(22) PCT Filed: Jun. 26, 2015

(86) PCT No.: PCT/GB2015/051877
§ 371 (c)(1),
(2) Date: Dec. 26, 2016

(87) PCT Pub. No.: WO2015/198072
PCT Pub. Date: Dec. 30, 2015

(65) Prior Publication Data

US 2017/0129931 A1 May 11, 2017

(30) Foreign Application Priority Data

Jun. 27, 2014 (GB) .................................. 1411506.7

(51) Int. Cl.
*C07K 14/495* (2006.01)
*C07K 16/28* (2006.01)

(52) U.S. Cl.
CPC ........ *C07K 14/495* (2013.01); *C07K 16/2863* (2013.01); *C07K 2319/02* (2013.01); *C07K 2319/30* (2013.01); *C07K 2319/50* (2013.01); *C07K 2319/73* (2013.01)

(58) Field of Classification Search
None
See application file for complete search history.

(56) References Cited

U.S. PATENT DOCUMENTS

| | | | | |
|---|---|---|---|---|
| 2003/0022316 A1* | 1/2003 | Fox | C07K 14/47 | 435/69.7 |
| 2010/0310515 A1* | 12/2010 | Chernajovsky | C07K 14/495 | 424/93.2 |

FOREIGN PATENT DOCUMENTS

| | | |
|---|---|---|
| WO | WO02055098 | 7/2002 |
| WO | WO09077755 | 6/2009 |

OTHER PUBLICATIONS

Mullen et al, J Biotech 161:269-277, 2012 (Year: 2012).*
Mullen et al (Chapter 16, Fusion Protein Technology for Biopharmaceuticals, published 2013, IDS-2 filed on Apr. 3, 2017 (Year: 2013).*
Mullen, Lisa M. et al., "Increased disulphide dimer formation of latent associated peptide fusions of TGF-[beta] by addition of 1-cystine", Journal of Biotechnology, 2012, 161(3) 269-277.
Mullen, Lisa et al., "Development of latent cytokine fusion proteins", Fusion Protein Technologies for Biopharmaceuticals, 2013, 237-252.
Mullen, Lisa et al., "Latency can be conferred to a variety of cytokines by fusion with latency-associated peptide from TGF-[beta]", Expert Opinion on Drug Delivery, 2014,11(1) 5-16.
Czajkowsky, Daniel M. et al., "Fc-fusion proteins: new developments and future perspectives", EMBO Molecular Medicine, 2012, 4(10) 1015-1028.

* cited by examiner

*Primary Examiner* — Lei Yao
(74) *Attorney, Agent, or Firm* — Stradley Ronon Stevens & Young, LLP

(57) ABSTRACT

The present invention provides a fusion protein comprising a latency associated peptide (LAP), a pharmaceutically active agent and an amino acid sequence comprising a dimerization domain, wherein the LAP and the pharmaceutically active agent are connected by an amino acid sequence comprising a proteolytic cleavage site. Also provided are nucleic acids enclosing such fusion proteins, process for their preparation, pharmaceutical compositions, kits and uses thereof in medicine.

7 Claims, 20 Drawing Sheets

Specification includes a Sequence Listing.

Fig. 1

Fig. 1 (continued)

| Protein | Sequence | Reference | SEQ ID NO: |
|---|---|---|---|
| MMP-1/MMP-8 | | | |
| Human type I collagen (α1) | Ala-Pro-Gln-Gly$_{775}$-Ile$_{776}$-Ala-Gly-Gln | 80 | 6 |
| Human type I collagen (α2) | Gly-Pro-Gln-Gly$_{775}$-Leu$_{776}$-Leu-Gly-Ala | 80 | 7 |
| Human type II collagen | Gly-Pro-Gln-Gly$_{775}$-Leu$_{776}$-Ala-Gly-Gln | 80 | 8 |
| Human type III collagen | Gly-Pro-Leu-Gly$_{775}$-Ile$_{776}$-Ala-Gly-Ile | 80 | 9 |
| Human α$_2$-macroglobulin | Gly-Pro-Glu-Gly$_{679}$-Leu$_{680}$-Arg-Val-Gly | 84 | 10 |
| Rat α$_1$-macroglobulin | Ala-Ala-Tyr-His$_{681}$-Leu$_{682}$-Val-Ser-Gln | 94 | 11 |
| Rat α$_1$-macroglobulin | Met-Asp-Ala-Phe$_{691}$-Leu$_{692}$-Glu-Ser-Ser | 84 | 12 |
| Rat α$_1$-macroglobulin | Glu-Pro-Gln-Ala$_{687}$-Leu$_{688}$-Ala-Met-Ser | 84 | 13 |
| Rat α$_1$-macroglobulin | Gln-Ala-Leu-Ala$_{688}$-Met$_{689}$-Ser-Ala-Ile | 84 | 14 |
| Chicken ovostatin | Pro-Ser-Tyr-Phe$_{676}$-Leu$_{677}$-Asn-Ala-Gly | 79 | 15 |
| Human pregnancy zone protein | Tyr-Glu-Ala-Gly$_{686}$-Leu$_{687}$-Gly-Val-Val | 84 | 16 |
| Human pregnancy zone protein | Ala-Gly-Leu-Gly$_{687}$-Val$_{688}$-Val-Glu-Arg | 84 | 17 |
| Human pregnancy zone protein | Ala-Gly-Leu-Gly$_{687}$-Ile$_{688}$-Ser-Ser-Thr | 84 | 18 |
| α$_1$-protease inhibitor | Gly-Ala-Met-Phe$_{352}$-Leu$_{353}$-Glu-Ala-Ile | 85 | 19 |
| Human aggrecan | Ile-Pro-Glu-Asn$_{341}$-Phe$_{342}$-Phe-Gly-Val | 86 | 20 |
| Human aggrecan | Thr-Glu-Gly-Glu$_{373}$-Ala$_{374}$-Arg-Gly-Ser | 86 | 21 |
| Human cartilage link | Arg-Ala-Ile-His$_{16}$-Ile$_{17}$-Gln-Ala-Glu | 87 | 22 |
| Human insulin-like growth factor binding protein-3 | Leu-Arg-Ala-Tyr$_{99}$-Leu$_{100}$-Leu-Pro-Ala | 88 | 23 |
| MMP-2 | | | |
| Guinea pig α1 (I) gelatin | Gly-Ala-Hyp-Gly$_{447}$-Leu$_{448}$-Glx-Gly-His | 24 | 24 |
| Rat α1 (I) gelatin | Gly-Pro-Gln-Gly$_{286}$-Val$_{287}$-Arg-Gly-Glu | 30 | 25 |
| Rat α1 (I) gelatin | Gly-Pro-Ala-Gly$_{277}$-Val$_{278}$-Gln-Gly-Pro | 30 | 26 |
| Rat α1 (I) gelatin | Gly-Pro-Ser-Gly$_{288}$-Leu$_{289}$-Hyp-Gly-Pro | 30 | 27 |
| Rat α1 (I) gelatin | Gly-Pro-Ala-Gly$_{295}$-Glu$_{296}$-Arg-Gly-Ser | 30 | 28 |

Fig. 2

| Protein | Sequence | Reference | SEQ ID NO: |
|---|---|---|---|
| Rat α1 (I) gelatin | Gly-Ala-Lys-Gly$_{581}$-Leu$_{582}$-Thr-Gly-Ser | 30 | 29 |
| Rat α1 (I) gelatin | Gly-Pro-Ala-Gly$_{586}$-Gln$_{587}$-Asp-Gly-Pro | 30 | 30 |
| Rat α1 (I) gelatin | Gly-Pro-Ala-Gly$_{614}$-Phe$_{615}$-Ala-Gly-Pro | 30 | 31 |
| Rat α1 (I) gelatin | Gly-Pro-Ile-Gly$_{616}$-Asn$_{617}$-Val-Gly-Ala | 30 | 32 |
| Rat α1 (I) gelatin | Gly-Pro-Hyl-Gly$_{685}$-Ser$_{686}$-Arg-Gly-Ala | 30 | 33 |
| Bovine type 1 collagen (α1) | Gly-Pro-Gln-Gly$_{775}$-Ile$_{776}$-Ala-Gly-Gln | 22 | 34 |
| Bovine type 1 collagen (α2) | Gly-Pro-Gln-Gly$_{775}$-Leu$_{776}$-Leu-Gly-Ala | 22 | 35 |
| Human aggrecan | Ile-Pro-Glu-Asn$_{341}$-Phe$_{342}$-Phe-Gly-Val | 89 | 36 |
| Human galectin-3 | Pro-Pro-Gly-Ala$_{62}$-Tyr$_{63}$-His-Gly-Ala | 90 | 37 |
| Human cartilage link | Arg-Ala-Ile-His$_{16}$-Ile$_{17}$-Gln-Ala-Glu | 87 | 38 |
| Human cartilage link | Gly-Pro-His-Leu$_{25}$-Leu$_{26}$-Val-Glu-Ala | 87 | 39 |
| Human insulin-like growth factor binding protein-3 | Leu-Arg-Ala-Tyr$_{98}$-Leu$_{99}$-Leu-Pro-Ala | 88 | 40 |
| MMP-3 | | | |
| Human α$_2$-macroglobulin | Gly-Pro-Glu-Gly$_{679}$-Leu$_{680}$-Arg-Val-Gly | 79 | 41 |
| Human α$_2$-macroglobulin | Arg-Val-Gly-Phe$_{684}$-Tyr$_{685}$-Glu-Ser-Asp | 79 | 42 |
| Human α$_1$-antichymotrypsin | Leu-Leu-Ser-Ala$_{360}$-Leu$_{361}$-Val-Glu-Thr | 91 | 43 |
| α$_1$-protease inhibitor | Glu-Ala-Ile-Pro$_{357}$-Met$_{358}$-Ser-Ile-Pro | 91 | 44 |
| Antithrombin III | Ile-Ala-Gly-Arg$_{385}$-Ser$_{386}$-Leu-Asn-Pro | 91 | 45 |
| Chicken ovostatin | Leu-Asn-Ala-Gly$_{377}$-Phe$_{378}$-Thr-Ala-Ser | 79, 82 | 46 |
| Human aggrecan | Ile-Pro-Glu-Asn$_{341}$-Phe$_{342}$-Phe-Gly-Val | 93 | 47 |
| Substance P | Lys-Pro-Gln-Gln$_6$-Phe$_7$-Phe-Gly-Leu | 37 | 48 |
| Human ProMMP-1 | Asp-Val-Ala-Gln$_{80}$-Phe$_{81}$-Val-Leu-Thr | 43 | 49 |
| Human ProMMP-3 | Asp-Thr-Leu-Glu$_{68}$-Val$_{69}$-Met-Arg-Lys | 94 | 50 |
| Human ProMMP-3 | Asp-Val-Gly-His$_{82}$-Phe$_{83}$-Arg-Thr-Phe | 94 | 51 |
| Human ProMMP-8 | Asp-Ser-Gly-Gly$_{77}$-Phe$_{78}$-Met-Leu-Thr | 95 | 52 |
| Human ProMMP-9 | Arg-Val-Ala-Gly$_{41}$-Met$_{42}$-Arg-Gly-Glu | 48 | 53 |
| Human ProMMP-9 | Asp-Leu-Gly-Arg$_{87}$-Phe$_{88}$-Gln-Thr-Phe | 48 | 54 |

Fig. 2
(continued)

| Protein | Sequence | Reference | SEQ ID NO: |
|---|---|---|---|
| Human fibronectin | Pro-Phe-Ser-Pro$_{89}$-Leu$_{90}$-Val-Ala-Thr | 21 | 55 |
| Human insulin-like growth factor binding protein-3 | Leu-Arg-Ala-Tyr$_{99}$-Leu$_{100}$-Leu-Pro-Ala | 88 | 56 |
| | Ala-Pro-Gly-Asn$_{109}$-Ala$_{110}$-Ser-Glu-Ser | 88 | 57 |
| | Phe-Ser-Ser-Glu$_{116}$-Ser$_{117}$-Lys-Arg-Glu | 88 | 58 |
| Bovine 1(II)collagen,N-telopeptide | Ala-Gly-Gly-Ala$_{115}$-Gln$_{116}$-Met-Gly-Val | 96 | 59 |
| Bovine 1(II)collagen,N-telopeptide | Gln-Met-Gly-Val$_{118}$-Met$_{119}$-Gln-Gly-Pro | 96 | 60 |
| Bovine α1(IX)collagen,NC2 | Met-Ala-Ala-Ser-Leu-Lys-Arg-Pro | 96 | 61 |
| Bovine α2(IX)collagen,NC2 | -Ala-Lys-Arg-Glu | 96 | 62 |
| Bovine α3(IX)collagen,NC2 | -Leu-Arg-Lys-Pro | 96 | 63 |
| Bovine α1(XI)collagen,N-telopeptide | Gln-Ala-Gln-Ala-Ile-Leu-Gln-Gln | 96 | 64 |
| Human cartilage link | Arg-Ala-Ile-His$_{16}$-Ile$_{17}$-Gln-Ala-Glu | 87 | 65 |
| Bovine insulin, B chain | Leu-Val-Glu-Ala$_{14}$-Leu$_{15}$-Tyr-Leu-Val | 97 | 66 |
| Bovine insulin, B chain MMP-7 | Glu-Ala-Leu-Tyr$_{16}$-Leu$_{17}$-Val-Cys-Gly | 21, 97 | 67 |
| Human aggrecan | Ile-Pro-Glu-Asn$_{26}$-Phe$_{26}$-Phe-Gly-Val | 89 | 68 |
| Human cartilage link | Gly-Pro-His-Leu$_{25}$-Leu$_{26}$-Val-Glu-Ala | 87 | 69 |
| Human prourokinase MMP-9 | Pro-Pro-Glu-Glu$_{143}$-Leu$_{144}$-Lys-Phe-Gln | 98 | 70 |
| Human type V collagen (α1) | Gly-Pro-Pro-Gly$_{435}$-Val$_{436}$-Val-Gly-Pro | 99 | 71 |
| Human type V collagen (α2) | Gly-Pro-pro-Gly$_{445}$-Leu$_{446}$-Arg-Gly-Glu | 99 | 72 |
| Human type XI collagen (α1) | Gly-Pro-Gly-Gly$_{449}$-Val$_{450}$-Val-Gly-Glu | 99 | 73 |
| Human aggrecan | Ile-Pro-Glu-Asn$_{26}$-Phe$_{26}$-Phe-Gly-Val | 89 | 74 |
| Human galectin-3 | Pro-Pro-Gly-Ala$_{62}$-Tyr$_{63}$-Ala-Gly-Ala | 90 | 75 |
| Human cartilage link MMP-10 | Arg-Ala-Ile-His$_{16}$-Ile$_{17}$-Gln-Ala-Glu | 87 | 76 |
| Human cartilage link | Arg-Ala-Ile-His$_{16}$-Ile$_{17}$-Gln-Ala-Glu | 87 | 77 |
| Human cartilage link | Gly-Pro-His-Leu$_{25}$-Leu$_{26}$-Val-Glu-Ala | 87 | 78 |

Fig. 2
(continued)

| Phage Code | Peptide Sequence | Avg. % Cleaved | SEQ ID NO: |
|---|---|---|---|
| D04 | ----MM█-GQR-█ERVLT | 99.7 | 79 |
| B05 | ----HN██-█QR██MVF-- | 99.6 | 80 |
| B07 | --NWQ█Q-AKR█-AY--- | 99.5 | 81 |
| D03 | ----L█I-█SN-█IMRWP | 99.4 | 82 |
| C02 | --DYM█I-█RQM█-QM--- | 99.4 | 83 |
| F03 | ---AL██-RAAD-█EYHF- | 99.3 | 84 |
| D01 | VEHLM█-QRKT-█---- | 99.2 | 85 |
| C05 | ---GVEV-█RQL█-HYM-- | 99.1 | 86 |
| B08 | -----QE█VGANIETYML | 99.0 | 87 |
| C06 | --QQM█V-SRYV-Q█KW--- | 98.9 | 88 |
| F05 | ---LQS█-RQAP-█DIWW- | 98.9 | 89 |
| H04 | ---QE█-RGKIE█QPFK-- | 98.9 | 90 |
| E03 | ---QQ█-MSGQYD█IP--- | 98.8 | 91 |
| D07 | ---SM█-A-ATV█STPE-- | 98.7 | 92 |
| C07 | ---EQQ█-█GRQ█HIII--- | 98.5 | 93 |
| B02 | -----M█-█GQ-█DMPYII | 98.5 | 94 |
| F01 | --GAY█V-GRW█YVDA-- | 98.3 | 95 |
| E01 | ---GQP█-TSPKI█-HK--- | 98.2 | 96 |
| B06 | --DVQ█-█GV-█-VIR-- | 98.0 | 97 |
| A05 | ----H█-█TVS█TYLML- | 98.0 | 98 |
| C04 | ---YM█-RGST█-FFN-- | 97.9 | 99 |
| F06 | ----Q█IGSY-█MPTN- | 97.9 | 100 |
| E01 | -HYY█-█DIEM█----- | 97.9 | 101 |
| A06 | ----N█HSSGI█-MLR-- | 97.8 | 102 |
| H01 | -DHPM█-█SKI█-K----- | 97.8 | 103 |
| A01 | --TFA█-█GTVS█AL--- | 97.7 | 104 |
| F04 | -GVHM█SM█RY-█-I---- | 97.7 | 105 |
| E05 | ---FQ█-ITG-█-DIMDP | 97.6 | 106 |
| A04 | -FQAVE█S█-TLH█W---- | 97.6 | 107 |
| D02 | ---VI█-TSR█Y-█TVWP- | 97.5 | 108 |
| F08 | -TDYL█-█SQPI█Y---- | 97.2 | 109 |
| B03 | -TFEQE█-RAPN-█SW--- | 97.1 | 110 |
| B04 | ---PQ█-VQG█AVE█-V- | 96.9 | 111 |
| F10 | ----APA-█AS-█HVYLM | 96.8 | 112 |
| D09 | --DYM█-VGNKI█-NI----- | 96.7 | 113 |
| F09 | --VIM█-V-GRR█-LQ--- | 96.5 | 114 |
| D10 | --FQA█-A█AV-█SS--- | 96.5 | 115 |
| F07 | -EDYVY█-█DVG█TN---- | 96.4 | 116 |
| A08 | ----Q█-AHH█-KLKS-- | 96.2 | 117 |
| C03 | ---YN█-█ATP█AVV--- | 95.8 | 118 |
| H03 | -----█FHANT█RIVQS- | 95.4 | 119 |
| G02 | ---AL█-S█FI-█-DIN-- | 95.3 | 120 |
| C01 | ----W█-VAAP--█MHTWV | 94.3 | 121 |
| E02 | ---PQ█-█AAE█WM--- | 94.1 | 122 |
| F02 | --NTLY█V-APPV█YV--- | 90.4 | 123 |
| G01 | -FQPY█-Q█IT-█-W---- | 89.9 | 124 |
| A02 | --KPM█SG█RT-█YY--- | 88.5 | 125 |
| G05 | ----M█-█GALQ█RLQP- | 82.9 | 126 |
| H02 | ---PQ█-█QARK█IIB-- | 79.4 | 127 |
| A07 | -YRQQ█-N█HIQI█----- | 34.2 | 128 |
| | E-[AFVLMY]-X(0,1)-[RK]-X(2,3)-[ST]-[VYIFWMLA] | | 129 |

Fig. 3

```
                              >CstNI         HaeI
            >CjePI            KpnI           MscI
             |                 |              |
AAG GCT CCA CAG GTG TAC ACC ATT CCA CCT CTC AAG GAG CAG ATG GCC AAG GAT AAA GTC   < 480
 K   A   P   Q   V   Y   T   I   P   P   L   K   E   Q   M   A   K   D   K   V

>BspMI                                          MslI            <CjePI
         |                                              |                |
AGT CTG ACC TGC ATG ATA ACA GAC TTC TTC CCT GAA GAC ATT ACT GTG GAG TGG CAG TGG   < 540
 S   L   T   C   M   I   T   D   F   F   P   E   D   I   T   V   E   W   Q   W

AAT GGG CAG CCA GCG GAG AAC TAC AAG AAC ACT CAG CCC ATC ATG GAC ACA GAT GGC TCT   < 600
 N   G   Q   P   A   E   N   Y   K   N   T   Q   P   I   M   D   T   D   G   S

SfcI
        AccI                              <SapI      >SmrI                >AarI
         |                                  |          |                    |
TAC TTC GTC TAC AGC AAG CTC AAT GTG CAG AAG AGC AAC TGG GAG GCA GGA AAT ACT TTC   < 660
 Y   F   V   Y   S   K   L   N   V   Q   K   S   N   W   E   A   G   N   T   F

Eco0109I
 >BspMI            PasI                                        <SapI          BstXI
   |                |                                            |              |
ACC TGC TCT GTG TTA CAT GAG GCC CTG CAC AAC CAC CAT ACT GAG AAG AGC CTC TCC CAC   < 720
 T   C   S   V   L   H   E   A   L   H   N   H   H   T   E   K   S   L   S   H

NcoI                              MslI
                         StyI         ApoI            <BcgI  >CdiI
              HindIII                 EcoRI           <BcgI  BstXI
                |          |            |               ||     ||
TCT CCT GGT AAA AAG CTT CCA TGG agg aat tcc tcc acc agc aag acc atc gac atg gag   < 780
 S   P   G   K   K   L   P   W   R   N   S   S   T   S   K   T   I   D   M   E AlwNI
                                            <Bsp24I
                                      HaeI
                                      MscI
                     >CdiI         StgI  >CjePI
                      |             |     |  |
ctg gtg aaa cgg aag cgc atc gaa gcc atc cgt ggc cag atc ctg tcc aaa cta agg ctc   < 840
 L   V   K   R   K   R   I   E   A   I   R   G   Q   I   L   S   K   L   R   L
                 BanI
```

Fig. 5 (continued)

```
                              KpnI
                              Acc65I
       <BsmFI          |
          |            |
gcc agt ccc cca agc cag ggg gag gta ccg ccc ggc ccg ctg ccc gag gcg gtg ctc gct  < 900
 A   S   P   S   Q   G   E   V   P   P   G   P   L   P   E   A   V   L   A BsiEI
                BstUI                        HaeII
                SelI                         KpnI     <SimI
                 |                             |        |
ttg tac aac agc acc cgc gac cgg gtg gca ggc gag agc gcc gac cca gag ccg gag ccc  < 960
 L   Y   N   S   T   R   D   R   V   A   G   E   S   A   D   P   E   P   E   P BstUI
                              AleI                    VpaK11AI
                              MalI                    PspOMI
                        BstEII   SelI                 AvaII
                          |       |                     |
gaa gtg gac tac tat gct aaa gag gtc acc cgc gtg cta atg gtg gac cgc aac aac gcc  < 1020
 E   V   D   Y   Y   A   K   E   V   T   R   V   L   M   V   D   R   N   N   A atc tat gag aaa acc aaa gac atc tca cac agt ata tat atg ttc ttc aat acg tca gac  < 1080
 I   Y   E   K   T   K   D   I   S   H   S   I   Y   M   F   F   N   T   S   D <BsrDI  <BsmFI                                BsaBI
                          |      |                                     |
att cgg gaa gca gtg ccc gaa ccc cca ttg ctg tcc cgt gca gag ctg cgc ttg cag aga  < 1140
 I   R   E   A   V   P   E   P   P   L   L   S   R   A   E   L   R   L   Q   R AflIII
                  NciI
MaeI              NspI
 |                 |
tta aaa tca agt gtg gag caa cat gtg gaa ctc tac cag aaa tat agc aac aat tcc tgg  < 1200
 L   K   S   S   V   E   Q   H   V   E   L   Y   Q   K   Y   S   N   N   S   W BsaBI
          BsrFI                              <HinfI                AatII
          BstEII    <SimI                      BglI                TraI
            |        |                          |                    |
cgt tac ctt ggt aac cgg ctg ctg acc ccc act gat acg cct gag tgg ctg tct ttt gac  < 1260
 R   Y   L   G   N   R   L   L   T   P   T   D   T   P   E   W   L   S   F   D
```

Fig. 5 (continued)

Fig. 5 (continued)

```
CAG AAG AGT TAC ACT GCC TTT GCC ATC CAA GAG ATG CTC CAG AAT GTC TTT CTT GTC TTC  < 1740
 Q   K   S   Y   T   A   F   A   I   Q   E   M   L   Q   N   V   F   L   V   F

>PfoI
                  >BmrI                                       >BsmAI
                  DraIII               <BsmAI                 >BsmBI                         
                    |                    |                      ||
AGA AAC AAT TTC TCC AGC ACT GGG TGG AAT GAG ACT ATT GTT GTA CGT CTC CTG GAT GAA  < 1800
 R   N   N   F   S   S   T   G   W   N   E   T   I   V   V   R   L   L   D   E

BfaI
                                ScaI                                         <BmgBI
                                  |                                            |
CTC CAC CAG CAG ACA GTG TTT CTG AAG ACA GTA CTA GAG GAA AAG CAA GAG CAA AGA TTG  < 1860
 L   H   Q   Q   T   V   F   L   K   T   V   L   E   E   K   Q   E   Q   R   L

KpnI
      >SplI                                                                Acc65I
      >BplI                              <SapI                             BanI
        |                                  |                                 |
ACG TGG GAG ATG TCC TCA ACT GCT CTC CAC TTG AAG AGC TAT TAC TGG AGG GTC CAA AGG  < 1920
 T   W   E   M   S   S   T   A   L   H   L   K   S   Y   Y   W   R   V   Q   R

<HinfI
                                                   VpaKllAI
                                                   AvaII
       NaeI     BspHI                              PspOMI           BglII
         |        |                                   |               |
TAC CTT AAA CTC ATG AAG TAC AAC AGC TAC GCC TGG ATG GTC GTC CGA CCA GAG ATC TTC  < 1980
 Y   L   K   L   M   K   Y   N   S   Y   A   W   M   V   V   R   P   E   I   F BfaI
                                                              XbaI
                                                              HinfI
                    BstBI                                     TfiI
                      |                                        ||
AGG AAC TTT CTC ATT ATT CGA AGA CTT ACC AGA AAC TTC CAA AAC TGA aTC TAG ACC     < 2037
 R   N   F   L   I   I   R   R   L   T   R   N   F   Q   N   *   I   *   T
```

Fig. 5 (continued)

SEQ ID
NO:
132 ATG TAC AGG ATG CAA CTC CTG TCT TGC ATT GCA CTA AGT CTT GCA CTT GTC ACG AAT TCC   < 60
133  M   Y   R   M   Q   L   L   S   C   I   A   L   S   L   A   L   V   T   N   S
134 TAC ATG TCC TAC GTT GAG GAC AGA ACG TAA CGT GAT TCA GAA CGT GAA CAG TGC TTA AGG

```
              >BdaI                                              >AcuI   <BpuBI
          <WviI                                                  >Eco57I
            |   |                                                   |   |
```

GAG CCC AAA TCT TGT GAC AAA ACT CAC ACA TGC CCA CCG TGC CCA GCA CCT GAA GCT GCG   < 120
 E   P   K   S   C   D   K   T   H   T   C   P   P   C   P   A   P   E   A   A
CTC GGG TTT AGA ACA CTG TTT TGA GTG TGT ACG GGT GGC ACG GGT CGT GGA CTT CGA CGC

```
    Eam1105I
    DriI                                              RcaI
    AhdI                                              PagI
    AspEI                                             CciI
    BmeRI                          >CchIII            BspHI    PfoI
        |                              |                  |        |
```

GGG GGA CCG TCA GTC TTC CTC TTC CCC CCA AAA CCC AAG GAC ACC CTC ATG ATC TCC CGG   < 180
 G   G   P   S   V   F   L   F   P   P   K   P   K   D   T   L   M   I   S   R
CCC CCT GGC AGT CAG AAG GAG AAG GGG GGT TTT GGG TTC CTG TGG GAG TAC TAG AGG GCC

```
                                <BtrI
                                <BmgBI
                                <AjiI      >BstEII
                                    |          |
```

ACC CCT GAG GTC ACA TGC GTG GTG GTG GAC GTG AGC CAC GAA GAC CCT GAG GTC AAG TTC   < 240
 T   P   E   V   T   C   V   V   V   D   V   S   H   E   D   P   E   V   K   F
TGG GGA CTC CAG TGT ACG CAC CAC CAC CTG CAC TCG GTG CTT CTG GGA CTC CAG TTC AAG

AAC TGG TAC GTG GAC GGC GTG GAG GTG CAT AAT GCC AAG ACA AAG CCG CGG GAG GAG CAG   < 300
 N   W   Y   V   D   G   V   E   V   H   N   A   K   T   K   P   R   E   E   Q
TTG ACC ATG CAC CTG CCG CAC CTC CAC GTA TTA CGG TTC TGT TTC GGC GCC CTC CTC GTC

```
                                                IagI
                                                BstENI
                                                EcoNI
                                                    |
```

TAC AAC AGC ACG TAC CGT GTG GTC AGC GTC CTC ACC GTC CTG CAC CAG GAC TGG CTG AAT   < 360
 Y   N   S   T   Y   R   V   V   S   V   L   T   V   L   H   Q   D   W   L   N
ATG TTG TCG TGC ATG GCA CAC CAG TCG CAG GAG TGG CAG GAC GTG GTC CTG ACC GAC TTA

Fig. 8

```
                                    >BsaI
                                    >Eco31I
         <PstI                      >Bso31I
         |                          |
         GGC AAG GAG TAC AAG TGC AAG GTC TCC AAC AAA GCC CTC CCA GCC CCC ATC GAG AAA ACC  < 420
          G   K   E   Y   K   C   K   V   S   N   K   A   L   P   A   P   I   E   K   T
         CCG TTC CTC ATG TTC ACG TTC CAG AGG TTG TTT CGG GAG GGT CGG GGG TAG CTC TTT TGG

ATC TCC AAA GCC AAA GGG CAG CCC CGA GAA CCA CAG GTG TAC ACC CTG CCC CCA TCC CGG  < 480
          I   S   K   A   K   G   Q   P   R   E   P   Q   V   Y   T   L   P   P   S   R
         TAG AGG TTT CGG TTT CCC GTC GGG GCT CTT GGT GTC CAC ATG TGG GAC GGG GGT AGG GCC

NahI
                          CaiI
                          SexAI
                          |
         GAG GAG ATG ACC AAG AAC CAG GTC AGC CTG ACC TGC CTG GTC AAA GGC TTC TAT CCC AGC  < 540
          E   E   M   T   K   N   Q   V   S   L   T   C   L   V   K   G   F   Y   P   S
         CTC CTC TAC TGG TTC TTG GTC CAG TCG GAC TGG ACG GAC CAG TTT CCG AAG ATA GGG TCG

<BtgII
         |
         GAC ATC GCC GTG GAG TGG GAG AGC AAT GGG CAG CCG GAG AAC AAC TAC AAG ACC ACG CCT  < 600
          D   I   A   V   E   W   E   S   N   G   Q   P   E   N   N   Y   K   T   T   P
         CTG TAG CGG CAC CTC ACC CTC TCG TTA CCC GTC GGC CTC TTG TTG ATG TTC TGG TGC GGA

Spy99I
                     |
         CCC GTG CTG GAC TCC GAC GGC TCC TTC TTC CTC TAT AGC AAG CTC ACC GTG GAC AAG AGC  < 660
          P   V   L   D   S   D   G   S   F   F   L   Y   S   K   L   T   V   D   K   S
         GGG CAC GAC CTG AGG CTG CCG AGG AAG AAG GAG ATA TCG TTC GAG TGG CAC CTG TTC TCG

Mph1103I
                     Asp700I                           NsiI
                     XmnI                              EcoT22I
                     MroXI                             Ppu10I
                     PdmI                              Zsp2I
                     |                                 |
         AGG TGG CAG CAG GGG AAC GTC TTC TCA TGC TCC GTG ATG CAT GAG GCT CTG CAC AAC CAC  < 720
          R   W   Q   Q   G   N   V   F   S   C   S   V   M   H   E   A   L   H   N   H
         TCC ACC GTC GTC CCC TTG CAG AAG AGT ACG AGG CAC TAC GTA CTC CGA GAC GTG TTG GTG

<BspjI
         <LguI
         <SapI                                          NcoI
                                                        Bsp19I
```

Fig. 8 (continued)

```
              <PciSI                              HindIII
               |                                   |
TAC ACG CAG AAG AGC CTC TCC CTG TCT CCG GGT AAA AAG CTT CCA TGG AGG AAT TCC CTA  < 780
 Y   T   Q   K   S   L   S   L   S   P   G   K   K   L   P   W   R   N   S   L
ATG TGC GTC TTC TCG GAG AGG GAC AGA GGC CCA TTT TTC GAA GGT ACC TCC TTA AGG GAT >ApyPI
                           |
TCC ACC AGT AAG ACT ATC GAC ATG GAG CTG GTG AAG CGG AAG CGC ATC GAG GCC ATC CGC  < 840
 S   T   S   K   T   I   D   M   E   L   V   K   R   K   R   I   E   A   I   R
AGG TGG TCA TTC TGA TAG CTG TAC CTC GAC CAC TTC GCC TTC GCG TAG CTC CGG TAG GCG GGC CAG ATC CTG TCC AAG CTG CGG CTC GCC AGC CCC CCG AGC CAG GGG GAG GTG CCG CCC  < 900
 G   Q   I   L   S   K   L   R   L   A   S   P   P   S   Q   G   E   V   P   P
CCG GTC TAG GAC AGG TTC GAC GCC GAG CGG TCG GGG GCT CGG TCC CCC CTC CAC GGC GGG GGC CCG CTG CCC GAG GCC GTG CTC GCC CTG TAC AAC AGC ACC CGC GAC CAG GTG GCC GGG  < 960
 G   P   L   P   E   A   V   L   A   L   Y   N   S   T   R   D   Q   V   A   G
CCG GGC GAC GGG CTC CGG CAC GAG CGG GAC ATG TTG TCG TGG GCG CTG GTC CAC CGG CCC GAG AGT GCA GAA CCG GAG CCC GAG CCT GAG GCC GAC TAC TAC GCC AAG GAG GTC ACC CGC  < 1020
 E   S   A   E   P   E   P   E   P   E   A   D   Y   Y   A   K   E   V   T   R
CTC TCA CGT CTT GGC CTC GGG CTC GGA CTC CGG CTG ATG ATG CGG TTC CTC CAG TGG GCG >Pth111II
                                               |
GTG CTA ATG GTG GAA ACC CAC AAC GAA ATC TAT GAC AAG TTC AAG CAG AGT ACA CAC AGC  < 1080
 V   L   M   V   E   T   H   N   E   I   Y   D   K   F   K   Q   S   T   H   S
CAC GAT TAC CAC CTT TGG GTG TTG CTT TAG ATA CTG TTC AAG TTC GTC TCA TGT GTG TCG ATA TAT ATG TTC TTC AAC ACA TCA GAG CTC CGA GAA GCG GTA CCT GAA CCC GTG TTG CTC  < 1140
 I   Y   M   F   F   N   T   S   E   L   R   E   A   V   P   E   P   V   L   L
TAT ATA TAC AAG AAG TTG TGT AGT CTC GAG GCT CTT CGC CAT GGA CTT GGG CAC AAC GAG AcvI
                                                            PmaCI
                                                            BbrPI
                                                            PmlI
                             <BpuEI                         Eco72I
                             <Bce83I                        PspCI
                              |                              |
TCC CGG GCA GAG CTG CGT CTG CTG AGG CTC AAG TTA AAA GTG GAG CAG CAC GTG GAG CTG  < 1200
 S   R   A   E   L   R   L   L   R   L   K   L   K   V   E   Q   H   V   E   L
AGG GCC CGT CTC GAC GCA GAC GAC TCC GAG TTC AAT TTT CAC CTC GTC GTG CAC CTC GAC
```

Fig. 8 (continued)

```
                                              AlfI
TAC CAG AAA TAC AGC AAC AAT TCC TGG CGA TAC CTC AGC AAC CGG CTG CTG GCA CCC AGC   < 1260
 Y   Q   K   Y   S   N   N   S   W   R   Y   L   S   N   R   L   L   A   P   S
ATG GTC TTT ATG TCG TTG TTA AGG ACC GCT ATG GAG TCG TTG CCG GAC GAC CGT GGG TCG

GAC TCG CCA GAG TGG TTA TCT TTT GAT GTC ACC GGA GTT GTG CGG CAA TGG TTG AGC CGT   < 1320
 D   S   P   E   W   L   S   F   D   V   T   G   V   V   R   Q   W   L   S   R
CTG AGC GGT CTC ACC AAT AGA AAA CTA CAG TGG CCT CAA CAC GCC GTC ACC AAC TCG GCA

BstH2I
                              BaeII
                              LpnI
                              BfoI
GGA GGG GAA ATT GAG GGC TTT CGC CTT AGC GCC CAC TGC TCC TGT GAC AGC AGG GAT AAC   < 1380
 G   G   E   I   E   G   F   R   L   S   A   H   C   S   C   D   S   R   D   N
CCT CCC CTT AAC TCC CCG AAA GCG GAA TCG CGG GTG ACG AGG ACA CTG TCG TCC CTA TTG

ACA CTG CAA GTG GAC ATC AAC GGG TTC ACT ACT GGC CGC CGA GGT GAC CTG GCC ACC ATT   < 1440
 T   L   Q   V   D   I   N   G   F   T   T   G   R   R   G   D   L   A   T   I
TGT GAC GTT CAC CTG TAG TTG CCC AAG TGA TGA CCG GCG GCT CCA CTG GAC CGG TGG TAA

ApaI
                                                                          PspOMI
                                          BstII                           Bsp120I
CAT GGC ATG AAC CGG CCT TTC CTG CTT CTC ATG GCC ACC CCC CTG GAG AGG GCC CAG CAT   < 1500
 H   G   M   N   R   P   F   L   L   L   M   A   T   P   L   E   R   A   Q   H
GTA CCG TAC TTG GCC GGA AAG GAC GAA GAG TAC CGG TGG GGG GAC CTC TCC CGG GTC GTA

AhfI
  ApaBI  SdaI                         AatII
  BstAPI Sse8387I                     ZraI
CTG CAA AGC CTG CAG GGA GGC GGG GGT TCA GAC GTC CAA GAG TTC CGC GGC GTC ACA GCT   < 1560
 L   Q   S   L   Q   G   G   G   G   S   D   V   Q   E   F   R   G   V   T   A
GAC GTT TCG GAC GTC CCT CCG CCC CCA AGT CTG CAG GTT CTC AAG GCG CCG CAG TGT CGA
                       BclI
```

Fig. 8 (continued)

Fig. 8 (continued)

```
                                          AspI
                                          Mth111I
                          EcoRII          PflFI
                          EcoRV           PsyI         <HpaBSI
                                            |           |
GGC GGA TCG GGA GGC GGA GGA TCC GAT ATC CAG ATG ACC CAG TCC CCG AGC TCC CTG TCC  < 2040
 G   G   S   G   G   G   G   S   D   I   Q   M   T   Q   S   P   S   S   L   S
CCG CCT AGC CCT CCG CCT CCT AGG CTA TAG GTC TAC TGG GTC AGG GGC TCG AGG GAC AGG

GCC TCT GTG GGC GAT AGG GTC ACC ATC ACC TGC CGT GCC AGT CAG GAT GTG AAT ACT GCT  < 2100
 A   S   V   G   D   R   V   T   I   T   C   R   A   S   Q   D   V   N   T   A
CGG AGA CAC CCG CTA TCC CAG TGG TAG TGG ACG GCA CGG TCA GTC CTA CAC TTA TGA CGA

GTA GCC TGG TAT CAA CAG AAA CCA GGA AAA GCT CCG AAA CTA CTG ATT TAC TCG GCA TCC  < 2160
 V   A   W   Y   Q   Q   K   P   G   K   A   P   K   L   L   I   Y   S   A   S
CAT CGG ACC ATA GTT GTC TTT GGT CCT TTT CGA GGC TTT GAT GAC TAA ATG AGC CGT AGG

BglII
                                            |
TTC CTC TAC TCT GGA GTC CTT TCT CGC TTC TCT GGG TCC AGA TCT GGG ACG GAT TTC ACT  < 2220
 F   L   Y   S   G   V   L   S   R   F   S   G   S   R   S   G   T   D   F   T
AAG GAG ATG AGA CCT CAG GAA AGA GCG AAG AGA CCC AGG TCT AGA CCC TGC CTA AAG TGA

CTG ACC ATC AGC AGT CTG CAG CCG GAG GAC TTC GCA ACT TAT TAC TGT CAG CAA TAT AAT  < 2280
 L   T   I   S   S   L   Q   P   E   D   F   A   T   Y   Y   C   Q   Q   Y   N
GAC TGG TAG TCG TCA GAC GTC GGC CTC CTG AAG CGT TGA ATA ATG ACA GTC GTT ATA TTA

NotI
                                       <BaeI                            CciNI
                                          |                               |
ACT ACT CCT CCC ACG TTC GGA CAG GGT ACC AAG GTG GAG ATC AAA CGC GCG GAT GCG GCC  < 2340
 T   T   P   P   T   F   G   Q   G   T   K   V   E   I   K   R   A   D   A   A
TGA TGA GGA GGG TGC AAG CCT GTC CCA TGG TTC CAC CTC TAG TTT GCG CGC CTA CGC CGG

XhoI
   Sfr274I
   SlaI
   SciI
   StrI
   PaeR7I
 PspXI
  | |
GCA CTC GAG CAC CAC CAC CAC CAC CAC TGA  < 2370
 A   L   E   H   H   H   H   H   H   *
CGT GAG CTC GTG GTG GTG GTG GTG GTG ACT
```

Fig. 8 (continued)

MODIFIED LATENCY ASSOCIATED PROTEIN CONSTRUCT

The present invention relates to the use of proteins, protein derivatives and DNA constructs that confer latency to pharmaceutically active agents. The present invention also relates to improved methods of providing latency to pharmaceutically active agents.

Most cytokines and growth factors are expressed under tight control mechanisms. Their gene expression is regulated by environmental stimuli such as infection, cell-cell interactions, change in extracellular matrix composition and interactions with adhesion molecules or via stimulation with other cytokines.

In addition to the control at the transcriptional and post-transcriptional level, some cytokines are not released into the medium unless a second signal activates the cell. A third level of regulation for cytokine activity is found in molecules which are secreted in a latent form and become "activated" by releasing the cytokine moiety where processes of inflammation, wound healing and tissue repair takes place (Khalil N, Microbes and Infection, 1, 1255-1263 (1999). In this latter respect, transforming growth factor beta (TGFβ) has received greatest attention.

TGFβ is synthesized as a dimeric latent cytokine composed of an amino terminal latency associated protein (LAP) and the active TGFβ cytokine at its COOH terminal end (Roberts and Sporn, Peptide Growth Factors and their Receptors: Sporn, M B and Roberts, A B, Springer-Verlag, 419-472 (1996); Roth-Eicchorn et al., Hepatology, 28 1588-1596 (1998)). The precursor peptide contains a signal peptide (residues 1-29) necessary for protein secretion and guiding the molecule through the Golgi apparatus to become processed by proteolytic cleavage and glycosylation. The LAP domain is separated from TGFβ by proteolytic cleavage at arginines (277-278). Mature TGFβ begins at alanine 279. The LAP, in addition to protect TGFβ, contains important residues necessary for the interaction with other molecules. Mutations in the LAP domain have recently been associated with the autosomal dominant Camurati-Engelmann disease (Janssens et al., Nature Genetics, 26, 273-275 (2000). Cysteines 224 and 226 are important in the intermolecular disulphide bond between two LAPs. Their mutation to serine renders the molecule "active" (Sanderson et al., Proc. Natl. Acad. Sci. USA, 92, 2572-2576 (1995); Brunner et al., Mol. Endocrinol. 6, 1691-1700 (1992); Brunner et al., J. Biol. Chem, 264, 13660-13664 (1989)). The RGD motif (245-247) facilitates the interaction with integrins (Munger et al., Mol, Biol. of the Cell, 9, 2627-2638 (1998; Derynck R, TIBS, 19, 548-553 (1994)). Nucleic acid encoding TGFβ is described in U.S. Pat. No. 5,801,231.

In most cell types studied, including those of mesenchymal, epithelial and endothelial origin, TGFβ is secreted in a latent form consisting of TGFβ and its latency associated peptide (LAP) propeptide dimers, covalently linked to latent TGFβ-binding proteins (LTBPs). LTBPs are also needed for the secretion and folding of TGFβ (Miyazano et al., EMBO J. 10, 1091-1101 (1991); Miyazano et al., J. Biol. Chem. 267, 5668-5675 (1992); Eklov et al., Cancer Res. 53, 3193-3197 (1993)). Cysteine 33 is important for the disulphide bridge with the third 8 cysteine-rich repeat of latent TGFβ binding protein (LTBP) (Saharinen et al., The EMBO Journal, 15, 245-253 (1996). Modification of LTBP by enzymes such as thrombospondin (Schultz et al., The Journal of Biological Chemistry, 269, 26783-26788 (1994); Crawford et al., Cell, 93, 1159-1170 (1998)), transglutaminase (Nunes et al., J. Cell, Biol. 136, 1151-1163 (1997); Kojima et al., The Journal of Cell Biology, 121, 439-448 (1993)) and MMP9, MMP2 (Yu and Stamenkovic, Genes and Dev, 14, 163-176 (2000)) could release the active portion of TGFβ from the latent complex.

Cytokines are natural products serving as soluble local mediators of cell-cell interactions. They have a variety of pleiotropic actions, some of which can be harnessed for therapeutic purposes. Targeting of cytokines to specific cell types using scFv (Lode et al., Pharmacol. Ther, 80, 277-292 (1998)) and vWF (Gordon et al., Human Gene Therapy, 8, 1385-1394 (1997)) have focused entirely on the active cytokine moiety of the cytokine complex.

Pharmacologically active proteins or other medicines based on such agents, which have to be administered at very high concentrations systemically in order to achieve biologically effective concentrations in the tissue being targeted, tend to give rise to undesirable systemic effects, for example toxicity, which limit their use and efficacy.

The principles underlying the construction of such a system for providing latency to pharmaceutically active agents using the LAP of TGF-β was described in WO 02/055098 and WO 2009/077755. In the naturally occurring LAP-TGF-β complex, the latency associated peptide forms a protective shell around TGFβ preventing it from being degraded. The closed nature of the shell is guaranteed because of internal interactions between TGFβ with LAP. These interactions are not necessarily expected when the 'payload' is another cytokine, growth factor or peptide or pharmaceutically active compound, and may result in a permeable shell which allows entry of mobile target molecules into the shell. For example, if the target molecule is a soluble receptor, the receptor may be able to enter the shell and interact with the pharmaceutically active agent even when the pharmaceutically active agent is bound to the LAP. This could lead to off-site activity which may have undesirable side effects. Furthermore, while improving protein production utilizing suspension cell cultures according to WO 2009/077755, the inventors found that, along with dimers, the LAP fusion proteins also tended to form active monomers.

The present inventors have now developed an improved means for providing pharmaceutically active agents in latent form based on this system.

According to the first aspect of the invention there is provided a fusion protein comprising a latency associated peptide (LAP), a pharmaceutically active agent and an amino acid sequence comprising a dimerisation domain wherein the LAP and pharmaceutically active agent are connected by an amino acid sequence comprising a proteolytic cleavage site.

The fusion protein comprising a LAP, a proteolytic cleavage site, a pharmaceutically active agent and a dimerisation domain may provide for site specific activation of the latent pharmaceutically active agent. The term "site specific activation" as used herein means, in general terms and not limited to the removal or reduction of latency, conferred on a pharmaceutically active agent, by site-specific cleavage at the proteolytic cleavage site.

Site-specific cleavage at the proteolytic cleavage site is expected to take place concomitantly with the restored activation of the pharmaceutically active agent.

The term "latent pharmaceutically active agent" as used herein may include, but is not limited to, pharmaceutically active agents which are latent due to their association with LAP and a proteolytic cleavage site. Specifically, the pharmaceutically active agent may be latent by virtue of its fusion to a LAP associated proteolytic cleavage site to form a latent fusion protein. The pharmaceutically active agent may be of natural or synthetic origin.

The fusion protein may be constructed as shown in FIG. 4(c) in which the dimerisation domain is fused to the LAP. An additional proteolytic cleavage site and/or linker sequence may be inserted also between the dimerisation domain and the LAP. A secretory signal peptide (i.e. the precursor peptide) may be fused to the dimerisation domain also at the N-terminal of the dimerisation domain.

The term "protein" in this text means, in general terms, a plurality of amino acid residues joined together by peptide bonds. It is used interchangeably and means the same as peptide, oligopeptide, oligomer or polypeptide, and includes glycoproteins and derivatives thereof. The term "protein" is also intended to include fragments, analogues and derivatives of a protein wherein the fragment, analogue or derivative retains essentially the same biological activity or function as a reference protein.

The fragment, analogue or derivative of the protein as defined in this text, may be at least 6, preferably 10 or 20, or up to 50 or 100 amino acids long.

The fragment, derivative or analogue of the protein may be (i) one in which one or more of the amino acid residues are substituted with a conserved or non-conserved amino acid residue (preferably, a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half life of the polypeptide (for example, polyethylene glycol), or (iv) one in which the additional amino acids are fused to the mature polypeptide, such as a leader or secretory sequence which is employed for purification of the polypeptide. Such fragments, derivatives and analogues are deemed to be within the scope of those skilled in the art from the teachings herein.

Particularly preferred are variants, analogues, derivatives and fragments having the amino acid sequence of the protein in which several e.g. 5 to 10, or 1 to 5, or 1 to 3, 2, 1 or no amino acid residues are substituted, deleted or added in any combination. Especially preferred among these are silent substitutions, additions and deletions, which do not alter the properties and activities of the protein of the present invention. Also especially preferred in this regard are conservative substitutions.

An example of a variant of the present invention is a fusion protein as defined above, apart from the substitution of one or more amino acids with one or more other amino acids. The skilled person is aware that various amino acids have similar properties. One or more such amino acids of a substance can often be substituted by one or more other such amino acids without eliminating a desired activity of that substance.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions.

Amino acid deletions or insertions may also be made relative to the amino acid sequence for the fusion protein referred to above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence of the fusion protein above can also be made. This may be done to alter the properties of a substance of the present invention (e.g. to assist in identification, purification or expression, as explained above in relation to fusion proteins).

Amino acid changes relative to the sequence for the fusion protein of the invention can be made using any suitable technique e.g. by using site-directed mutagenesis. It should be appreciated that amino acid substitutions or insertions within the scope of the present invention can be made using naturally occurring or non-naturally occurring amino acids. Whether or not natural or synthetic amino acids are used, it is preferred that only L-amino acids are present.

A protein according to the invention may have additional N-terminal and/or C-terminal amino acid sequences. Such sequences can be provided for various reasons, for example, glycosylation.

The term "fusion protein" in this text means, in general terms, one or more proteins joined together by chemical means, including hydrogen bonds or salt bridges, or by peptide bonds through protein synthesis or both.

The latency associated peptide (LAP) of the present invention may include, but is not limited to, the coding sequence for the precursor domain of TGFβ or a sequence which is substantially identical thereto.

"Identity" as known in the art is the relationship between two or more polypeptide sequences or two or more polynucleotide sequences, as determined by comparing the sequences. In the art, identity also means the degree of sequence relatedness (homology) between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic acids Research, 12, 387 (1984), BLASTP, BLASTN, and FASTA (Atschul et al., J. Molec. Biol. 215, 403 (1990).

The LAP of the present invention may comprise the precursor domain of TGFβ, for example, the precursor peptide of TGFβ-1, 2 or 3 (from human) (Derynck et al., Nature, 316, 701-705 (1985); De Martin et al., EMBO J. 6 3673-3677 (1987); Hanks et al., Proc. Natl. Acad. Sci. 85, 79-82 (1988); Derynck et al., EMBO J. 7, 3737-3743 (1988); Ten Dyke et al., Proc. Natl. Acad. Sci. USA, 85, 4715-4719 (1988)) TGFβ-4 (from chicken) (Jakowlew et al., Mol. Endocrinol. 2, 1186-1195 (1988)) or TGFβ-5 (from xenopus) (Kondaiah et al., J. Biol. Chem. 265, 1089-1093 (1990)). The term "precursor domain" is defined as a sequence encoding a secretory signal peptide (i.e. a precursor peptide) which does not include the sequence encoding the mature protein. The amino acid sequences of the precursor domain of TGFβ 1, 2, 3, 4 and 5 (Roberts and Sporn, Peptide Growth Factors and their Receptors: Sporn, M B and Roberts, A B, Springer-Verlag, Chapter 8, 422 (1996)) are shown in FIG. 1.

Preferably, the amino acid sequence of the LAP has at least 50% identity, using the default parameters of the BLAST computer program (Atschul et al., J. Mol. Biol. 215, 403-410 (1990) provided by HGMP (Human Genome Mapping Project), at the amino acid level, to the precursor domain of TGFβ 1, 2, 3, 4 or 5 (Roberts and Sporn, Peptide Growth Factors and their Receptors: Sporn, M B and Roberts, A B, Springer-Verlag, Chapter 8, 422 (1996)) as shown in FIG. 1. More preferably, the LAP may have at least 60%, 70%, 80%, 90% and still more preferably 95% (still more preferably at least 99%) identity, at the nucleic acid or amino acid level, to the precursor domain of TGFβ 1, 2, 3, 4 or 5 as shown in FIG. 1 which comprises residues 1 to 278.

The LAP may comprise the LAP of TGFβ 1, 2, 3, 4, or 5 (Roberts and Sporn, Peptide Growth Factors and their Receptors: Sporn, M B and Roberts, A B, Springer-Verlag, Chapter 8, 422 (1996)) as shown in FIG. 1.

The LAP may contain at least two, for example at least 4, 6, 8, 10 or 20 cysteine residues for the formation of disulphide bonds.

The LAP may also comprise a sequence which has at least 50%, 60%, 70%, 80%, 90%, 95% or 99% identity with a LAP sequence of FIG. 1, using the default parameters of the BLAST computer program provided by HGMP, thereto.

The "dimerisation domain" refers to a peptide having affinity for a second peptide, such that the two peptides associate under physiological conditions to form a dimer. The second peptide may be the same or a different peptide. The dimerisation domain may also refer to polypeptides. The peptides or polypeptides may interact with each other through covalent and/or non-covalent association(s).

The dimerisation domain may be linked to the latency associated peptide by a linker. The linker size can be varied to vary the size of the shell in order to accommodate the pharmaceutically active agent. The linker peptide may comprise the amino acid sequence GGGGS (SEQ ID NO:135) or a multimer thereof (for example a dimer, a trimer, or a tetramer), a suitable linker may be (GGGGS)$_3$ (SEQ ID NO:136), or a sequence of nucleotides which has at least 50%, 60%, 70%, 80%, 90%, 95% or 99% identity, using the default parameters of the BLAST computer program provided by HGMP, thereto.

Examples of dimerisation domains include antibody fragment polypeptides such as an immunoglobulin Fc polypeptide, an immunoglobulin hinge polypeptide, a CH3 domain polypeptide, a CH4 domain polypeptide, a CH1 domain or CL domain polypeptide; a leucine zipper domain (e.g., a jun/fos leucine zipper domain, see, e.g., Kostelney et al., J. Immunol., 148:1547-1553, 1992; or a yeast GCN4 leucine zipper domain); an isoleucine zipper domain; a dimerising region of a dimerising cell-surface receptor (e.g., interleukin-8 receptor (IL-8R); or an integrin heterodimer such as LFA-1 or GPIIIb/IIIa); a dimerising region of a secreted, dimerising ligand (e.g., nerve growth factor (NGF), neurotrophin-3 (NT-3), interleukin-8 (IL-8), vascular endothelial growth factor (VEGF), or brain-derived neurotrophic factor (BDNF); see, e.g., Arakawa et al., J. Biol. Chem. 269:27833-27839, 1994, and Radziejewski et al., Biochem. 32:1350, 1993); or a polypeptide comprising at least one cysteine residue (e.g., one, two, or three to about ten cysteine residues) such that disulfide bond(s) can form between the polypeptide and a second polypeptide comprising at least one cysteine residue. Suitably the dimerisation domain may be an Fc polypeptide.

An immunogobulin hinge polypeptide typically comprises a region which is rich in proline and cysteine amino acid residues. A common sequence motif present in the hinge polypeptide region may be may be CPXCP (SEQ ID NO:137) where X can be another residue that does not interfere with dimerisation, for example proline (P), arginine (R) or serine (S). The hinge region polypeptide may be from around 10 to 75 amino acid residues. The hinge region polypeptide may contain a plurality of cysteine-cysteine disulphide bonds, for example of from 2 to 15. The hinge region polypeptide may comprise the sequence CPXCP where X can be another residue that does not interfere with dimerisation, for example proline (P), arginine (R) or serine (S). A number of repeats of the sequence CPXCP may be present also, for example 2, 3, 4, or 5 repeats, or greater.

Wypych et al., J. Biol. Chem. 28316194-16205, 2008 defined the following hinge region peptide sequences for IgG antibodies as shown in Table 1 below:

TABLE 1

| IgG subtype | Core hinge sequences |
| --- | --- |
| IgG1 | EPKSCDKTHTCPPCP (SEQ ID NO: 138) |
| IgG2 | ERKCCVECPPCP (SEQ ID NO: 139) |
| IgG3 | ELKTPLGDTTHTCPRCP (SEQ ID NO: 140) |
|  | (EPKSCDTPPPCPRCP)$_3$ (SEQ ID NO: 141) |
| IgG4 | ESKYGPPCPSCP (SEQ ID NO: 142) |

The terms "antibody" and "immunoglobulin" are used herein interchangeably. An antibody molecule is made up of two identical heavy (H) and two identical light (L) chains held together by disulphide bonds. Each heavy chain comprises an Fc polypeptide. The two Fc polypeptides from the two heavy chains dimerise to form the Fc region of the antibody molecule. The term "Fc region" refers to the constant region of an antibody excluding the first constant region immunoglobulin domain of the heavy chain (CH1) that interacts with the constant portion of the light chain (CL) forming a CH1-CL domain pair. Thus, Fc region comprises the last two constant region immunoglobulin domains (CH2 and CH3) of IgA, IgD, and IgG, and the last three constant region immunoglobulin domains of IgE and IgM (CH2, CH3 and CH4), Any polypeptide of the various immunoglobulin constant domains may therefore be used in accordance with the present invention as a dimerisation domain.

Several antibody effector functions are mediated through the binding of the Fc region to Fc receptors (FcR) found on the surface of many cells for example lymphocytes, macrophages, natural killer cells, etc. FcRs are defined by their specificity for antibody isotypes. For example, Fc receptors for IgG antibodies are referred to as FcγR.

IgG is also bound by the neonatal Fc receptor (FcRn). In humans, IgG exhibits a long serum half-life. Studies indicate that this is due to the protective effect of FcRn which binds to the Fc region of IgG and prevents degradation by allowing intracellular recycling.

The Fc polypeptide may be selected to alter, e.g. increase or decrease the half-life of the fusion protein. As used herein, the term "half-life" refers to a biological half-life of a particular polypeptide or protein in vivo. Half-life may be represented by the time required for half the quantity administered to a subject to be cleared from the circulation and/or other tissues in the animal. In an embodiment of the invention the Fc polypeptide is an IgG Fc polypeptide.

IgG antibodies can be further subdivided into IgG1, IgG2, IgG3 and IgG4. In an embodiment of the invention the Fc polypeptide may be IgG1, IgG2, IgG3 and IgG4 polypeptide, for example an IgG1 polypeptide.

The Fc polypeptide may be selected to target the fusion protein to specific tissues, for example the mucosa. The IgA antibody plays an important role in mucosal immunity for e.g. in the respiratory tract and the gastrointestinal mucosal lining. In its secretory form, IgA is found in mucous secretions such as tears, saliva, colostrum, gastrointestinal and genitourinary fluids. IgA deficiency is associated with a number of autoimmune diseases such as rheumatoid arthritis, systemic lupus erythematosus and immune thrombocytopenic purpura. IgA deficiency is also associated with allergic diseases such as asthma. In another embodiment of the invention the Fc polypeptide may be an IgA polypeptide.

The Fc polypeptides may be derived from the same antibody isotype to form a homodimeric Fc region or from different antibody isotypes to form a heterodimeric Fc region. The Fc polypeptide may be a naturally occurring polypeptide or may be an engineered polypeptide.

The LAP may provide a protective "shell" around the pharmaceutically active agent thereby shielding it and hindering, or preventing, its interaction with other molecules in the cell surface or molecules important for its activity.

The dimerisation domain enables the fusion of the amino terminals of two latency associated proteins thereby effectively closing the LAP shell. The dimerisation domains are therefore complementary and permit dimerisation to occur. The closure of the shell does not depend on the interaction of LAP with the pharmaceutically active agent. The closure also prevents monomer formation of the LAP fusion proteins.

Closure of the shell also prevents any interaction between the pharmaceutically active agent and its target molecule unless the pharmaceutically active agent is released from the LAP fusion protein by proteolytic activity. This ensures site-specific delivery of the pharmaceutically active agent and may reduce off-site activity.

In one alternative embodiment of the invention, therefore, there is provided a protein construct comprising two fusion proteins as defined in the first aspect of the invention which are present as a dimer. The dimer is composed of monomers of the first aspect of the invention which may be the same or different with respect to the latency associated peptide (LAP), the pharmaceutically active agent, and the amino acid sequence comprising a proteolytic cleavage site.

The dimer may therefore be composed of a first monomer and a second monomer, in which the first monomer comprises a latency associated peptide (LAP), a pharmaceutically active agent and an amino acid sequence comprising a dimerisation domain wherein the LAP and pharmaceutically active agent are connected by an amino acid sequence comprising a proteolytic cleavage site, and a second monomer comprising a latency associated peptide (LAP), a pharmaceutically active agent and an amino acid sequence comprising a dimerisation domain wherein the LAP and pharmaceutically active agent are connected by an amino acid sequence comprising a proteolytic cleavage site.

The present invention therefore provides a composition comprising two fusion proteins according to the first aspect, wherein the fusion proteins are associated at the dimerisation domain in each fusion protein.

The proteolytic cleavage site may comprise any protease specific cleavage site. The proteolytic cleavage site may include, but is not limited to, a matrix metalloproteinase (MMP) cleavage site, a serine protease cleavage site, an aggrecanase cleavage site, a site cleavable by a parasitic protease derived from a pathogenic organism (Zhang et al., J. Mol. Biol. 289, 1239-1251 (1999); Voth et al., Molecular and Biochemical Parasitology, 93, 31-41 (1998); Yoshioka et al., Folia Pharmacologica Japonica, 110, 347-355 (1997); Tort et al, Advances in Parasitology, 43, 161-266 (1999); McKerrow, International Journal for Parasitology, 29, 833-837 (1999); Young et al., International Journal for Parasitology, 29, 861-867 (1999); Coombs and Mottram, Parasitology, 114, 61-80 (1997)) or a site cleavable by the proteins of the complement cascade (Carroll, Annu. Rev. Immunol. 16, 545-568 (1998); Williams et al., Ann. Allergy, 60, 293-300 (1988)).

Suitably, the proteolytic cleavage site of the fusion proteins of the present invention is cleaved when the fusion protein is located at or introduced to a site of disease diagnosed as an inflammatory condition, e.g. arthritis, or cancer which can be characterized by inflammation and/or tissue remodelling.

A MMP cleavage site may comprise a number of amino acid residues recognisable by MMP. Preferably, the MMP cleavage site comprises the minimum number of amino acid residues required for recognition and cleavage by MMP. Moreover, the amino acids of the MMP site may be linked by one or more peptide bonds which are cleavable, proteolytically, by MMP. MMPs which may cleave the MMP site include, but are not limited to, MMP1, MMP2, MMP3, MMP7, MMP8, MMP9, MMP10 and MMP13 (Yu and Stamenkovic, Genes and Dev. 14, 163-176 (2000); Nagase and Fields, Biopolymers, 40, 399-416 (1996); Massova et al., J. Mol. Model. 3, 17-30 (1997); reviewed in Vu and Werb; Genes and Dev. 14, 2123-2133 (2000)).

The MMP cleavage site e.g. any one or more of MMP1, MMP2, MMP3, MMP7, MMP8, MMP9 or MMP10 may be as shown in FIG. 2 or a sequence of amino acids which has at least 50%, 60%, 70%, 80%, 90%, 95% or 99% identity with the sequences shown in FIG. 2, using the default parameters of the BLAST computer program provided by HGMP, thereto. In an embodiment the MMP proteolytic cleavage site has the amino acid sequence PLGLWA.

The proteolytic cleavage site may also comprise any aggrecanase specific cleavage site which is cleavable by an aggrecanase. An aggrecanase cleavage site may comprise a number of amino acid residues recognisable by an aggrecanase. Moreover, the amino acids of the aggrecanase site may be linked by one or more peptide bonds which are cleavable, proteolytically, by aggrecanase.

Aggrecanases which may cleave the aggrecanase site include, but are not limited to ADAMTS-4 (aggrecanase-1), ADAMTS-5 (aggrecanase-2) and ADAMTS-11 (Tortorella, M. D., et al Osteoarthritis Cartilage, 2001. 9(6): p. 539-552); Abbaszade, I., et al J Biol Chem, 1999. 274(33): p. 23443-23450).

The sequences of the protein cleavage sites of ADAMTS-4 (aggrecanase-1) are shown in FIG. 3. Suitable ADAMTS-4 sites include:

```
HNEFRQRETYMVF        (SEQ ID NO: 80)

DVQEFRGVTAVIR        (SEQ ID NO: 97)
```

The consensus ADAMTS-4 cleavage motif can be represented according to Hills et al (J. Biol. Chem. 282 11101-11109 (2007)) as:

(SEQ ID NO: 129)
E-[AFVLMY]-X$_{(0,1)}$-[RK]X$_{(2,3)}$-[ST]-[VYIFWMLA]

The aggrecanase proteolytic cleavage site of the present invention may be cleaved by ADAMTS-4 (aggrecanase-1), ADAMTS-5 (aggrecanase-2) or ADAMTS-11.

The amino acid sequence of the aggrecanase cleavage site may include a sequence which has at least 50%, 60%, 70%, 80%, 90%, 95% or 99% identity, using the default parameters of the BLAST computer program provided by HGMP, thereto. Preferably, the nucleic acid sequence encoding the aggrecanase cleavage site comprises the minimum number of residues required for recognition and cleavage by an aggrecanase.

The present invention may further provide a "linker" peptide. Preferably the linker peptide is linked to the amino acid sequence of the proteolytic cleavage site. The linker peptide may be provided at the C terminal or N terminal end of the amino acid sequence encoding the proteolytic cleavage site. Preferably, the linker peptide is continuous with the amino acid sequence of the proteolytic cleavage site. The linker peptide may comprise the amino acid sequence GGGGS (SEQ ID NO:135) or a multimer thereof (for example a dimer, a trimer, or a tetramer), a suitable linker may be (GGGGS)$_3$ (SEQ ID NO:136), or a sequence of nucleotides which has at least 50%, 60%, 70%, 80%, 90%, 95% or 99% identity, using the default parameters of the BLAST computer program provided by HGMP, thereto.

The term "linker peptide" is intended to define any sequence of amino acid residues which preferably provide a hydrophilic region when contained in an expressed protein. Such a hydrophilic region may facilitate cleavage by an enzyme at the proteolytic cleavage site.

The constructs of the invention may also comprise an additional linker sequence and/or proteolytic cleavage site between the dimerisation domain and the LAP.

The term "latency" as used herein, may relate to a shielding effect which may hinder interaction between the fusion protein and other molecules in the cell surface. Alternatively the term latency may be used to describe a reduction in the activity (up to and including ablation of activity) of a molecule/agent associated with the fusion protein. The term latency may also relate to a stabilising effect of the fusion protein. The effect may be in full or partial, where a partial effect is sufficient to achieve the latency of the active agent.

The term "associating with" in the context of the present invention is intended to include all means of association including, but not limited to, chemical cross-linking or peptide bond linkage.

The pharmaceutically active agent may be a pharmaceutically active protein which can include, but is not limited to, an antibody, a growth factor (e.g. TGFβ, epidermal growth factor (EGF), platelet derived growth factor (PDGF), nerve growth factor (NGF), colony stimulating factor (CSF), hepatocyte growth factor, insulin-like growth factor, placenta growth factor); a differentiation factor; a cytokine e.g. an interleukin, (e.g. IL1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32 or IL-33 or an interferon (e.g. IFN-α, IFN-β and IFN-γ), tumour necrosis factor (TNF), IFN-γ inducing factor (IGIF), a bone morphogenetic protein (BMP, e.g. BMP-1, BMP-2, BMP-3, BMP-4, BMP-4, BMP-5, BMP-6, BMP-7, BMP-8, BMP-9, BMP10, BMP-11, BMP-12, BMP-13); an interleukin receptor antagonist (e.g. IL-1ra, IL-1RII), a tumor necrosis factor inhibitor (TNF-R or anti-TNF); a chemokine (e.g. MIPs (Macrophage Inflammatory Proteins) e.g. MIP1α and MIP1β; MCPs (Monocyte Chemotactic Proteins) e.g. MCP1, 2 or 3; RANTES (regulated upon activation normal T-cell expressed and secreted)); a trophic factor; a cytokine inhibitor; a cytokine receptor; a free-radical scavenging enzyme e.g. superoxide dismutase or catalase; a pro-drug converting enzyme (e.g. angiotensin converting enzyme, deaminases, dehydrogenases, reductases, kinases, urate oxidase and phosphatases); a peptide mimetic; a protease inhibitor; a tissue inhibitor of metalloproteinases (TIMPs e.g. TIMP1, TIMP2, TIMP3 or TIMP4) or a serpin (inhibitors of serine proteases). Preferably, the pharmaceutically active agent will be derived from the species to be treated e.g. human origin for the treatment of humans.

Preferably, the pharmaceutically active agent may be a cytokine, e.g. IFNβ, IL-4, or IL-1ra, or a cytokine inhibitor, such as an antibody or antibody fragment, e.g. trastuzumab, and as defined herein below.

The interleukins and cytokines may be anti-inflammatory or pro-inflammatory. Anti-inflammatory cytokines and certain interleukins, such as IL-4 and/or IL-10, are suitable for the treatment of arthritis, whereas pro-inflammatory cytokines and other interleukins, such as IL-1 and IL-2, are suitable for the treatment of cancer.

As used herein "peptide mimetics" includes, but is not limited to, agents having a desired peptide backbone conformation embedded into a non-peptide skeleton which holds the peptide in a particular conformation. Peptide mimetics, which do not have some of the drawbacks of peptides, are of interest in those cases where peptides are not suitable in medicine.

Peptide mimetics may comprise a peptide backbone which is of the L- or D-conformation. Examples of peptides mimetics include melanocortin, adrenocorticotrophin hormone (ACTH) and other peptide mimetic agents which play a role in the central nervous system, endocrine system in signal transduction and in infection and immunity.

The pharmaceutically active agent may comprise a chemical compound such as a chemotherapeutic agent or other synthetic drug. Alternatively, the pharmaceutically active agent may comprise an siRNA or a peptide nucleic acid (PNA) sequence e.g. a poly-lysine sequence which binds to nucleic acids and permeabilises lipid bilayers (Wyman et al., Biological Chemistry, 379, 1045-1052 (1998)) or a KALA peptide which facilitates transfer through lipid bilayers (Wyman et al., Biochemistry, 36, 3008-3017 (1997)) or a protein transduction domain (PTD) that enables polypeptides to enter cells via the plasma membrane (Pi et al Molecular Therapy 2, 339-347 (2000)).

The pharmaceutically active agent may be suitable for interacting with soluble target molecules. Examples of soluble target molecules include cytokines, growth factors, signaling proteins and other ligands and receptors.

The pharmaceutically active agent may be a cytokine inhibitor. The term "cytokine inhibitor" refers to a molecule that can block, reduce, inhibit or neutralise a function, an activity and/or the expression of a cytokine. The cytokine inhibitor may be a protein (for example soluble cytokine receptor protein); an antibody or antibody fragment; nucleic acid (for example siRNA or anti-sense nucleic acid) or organic or inorganic molecules.

Examples of suitable antibodies include but are not limited to anti-TNF (e.g. anti-TNF α, anti-TNF β), anti-interleukins (e.g. anti-IL-1, anti-IL-2, anti-IL-3, anti-IL-4, anti-IL-5, anti-II-6, anti-IL-7, anti-IL-8, anti-IL-9, anti-IL-10, anti-IL-11, anti-IL-12, anti-IL-13, anti-IL-14, anti-IL-15, anti-IL-16, anti-IL-17, anti-IL-18, anti-IL-19, anti-IL-20, anti-IL-21, anti-IL-22, anti-IL-23, anti-IL-24, anti-IL-25, anti-IL-26, anti-IL-27, anti-IL-28, anti-IL-29, anti-IL-30, anti-IL-31, anti-IL-32, anti-IL-33, anti-IL-34, anti-IL-35 and IL-36), anti-interferons (e.g. anti-INF-α, anti-INF-β, anti-INF-γ and anti-INF-ω) and fragments thereof.

Examples of such molecules also include trastuzumab (also known as Herclon™/Herceptin™), a monoclonal antibody to the HER2/neu receptor.

The pharmaceutically active agent may be an antibody or an antibody fragment. An "antibody fragment" as referred to herein means any portion of a full length antibody. Examples of antibody fragments include, but are not limited to, Fab, Fab', F(ab')2, scFv, Fv, dsFv diabody and Fd fragments.

The term "single chain variable fragment" or "scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

The antibody or antibody fragment may be suitable for use in the treatment of inflammatory conditions such as arthritis, gout, atherosclerosis, allograft rejection, Crohn's disease, inflammatory bowel disease, irritable bowel syndrome and colitis.

In an alternative embodiment, the invention further provides the fusion protein of the present invention optionally in association with latent TGFβ binding protein (LTBP). Typically, the fusion protein is covalently linked to LTBP to form a complex. Preferably, the association is mediated by disulphide bond(s) between Cys No. 33 of LAP and the third 8 Cys residue of LTBP. The LTBP associated with the fusion protein may include, but is not limited to, LTBP 1, 2, 3 or 4 (Kanzaki et al., Cell, 61, 1051-1061 (1990); Tsuji et al., Proc. Natl. Acad. Sci. USA, 87, 8835-8839 (1990); Moren et al., J. Biol. Chem. 269, 32469-32478 (1994); Yin et al., J. Biol. Chem. 270, 10147-10160 (1995); Gibson et al., Mol. Cell. Biol. 15, 6932-6942 (1995); Saharinen et al., J. Biol. Chem. 273, 18459-18469 (1998)), or fragments of LTBP such as that containing the third 8 Cys repeat, or homologues having a sequence of amino acids or nucleotides which has at least 50%, 60%, 70%, 80%, 90%, 95% or 99% identity, using the default parameters of the BLAST computer program provided by HGMP, to that of LTBP.

Cleavage of LTBP may release the fusion protein from the LTBP complex. Enzymes which may cleave LTBP in this manner include, but are not limited to, thrombospondin (Schultz et al., The Journal of Biological Chemistry, 269, 26783-26788 (1994); Crawford et al., Cell, 93, 1159-1170 (1998)), transglutaminase (Nunes et al., J. Cell, Biol. 136, 1151-1163 (1997); Kojima et al., The Journal of Cell Biology, 121, 439-448 (1993)) MMP9 and MMP2 (Yu and Stamenkovic, Genes and Dev, 14, 163-176 (2000)).

The invention further provides nucleic acid encoding the fusion protein of the first aspect of the invention as defined above. A second aspect of the invention provides a nucleic acid construct comprising a first nucleic acid sequence encoding a pharmaceutically active agent, a second nucleic acid sequence encoding a LAP and a third nucleic acid sequence encoding a dimerisation domain polypeptide.

The term "nucleic acid construct" generally refers to any length of nucleic acid which may be DNA, cDNA or RNA such as mRNA obtained by cloning or produced by chemical synthesis. The DNA may be single or double stranded. Single stranded DNA may be the coding sense strand, or it may be the non-coding or anti-sense strand. For therapeutic use, the nucleic acid construct is preferably in a form capable of being expressed in the subject to be treated.

The pharmaceutically active agent may be suitable for interacting with soluble target molecules. Examples of soluble target molecules include cytokines, growth factors, signaling proteins and other ligands and receptors.

In an embodiment of the invention, the first nucleic acid sequence encodes a cytokine inhibitor. The term "cytokine inhibitor" refers to a molecule that can block, reduce, inhibit or neutralise a function, an activity and/or the expression of a cytokine. The cytokine inhibitor may be a protein (for example soluble cytokine receptor protein); an antibody or antibody fragment; nucleic acid (for example siRNA or anti-sense nucleic acid).

Where the first nucleic acid construct encodes an antibody or an antibody fragment, the antibody fragment may be, for example, an Fab, Fab', F(ab')2, scFv, Fv, dsFv diabody or Fd fragment. Examples of such molecules include trastuzumab (also known as Herclon™/Herceptin™), a monoclonal antibody to the HER2/neu receptor.

In some embodiments, the first nucleic acid sequence encodes the protein IFNβ, IL-4 or IL-1ra. In one embodiment of the invention, the first nucleic acid sequence encodes IFNβ, IL-4 or IL-1ra from a mouse or a human.

The nucleic acid construct of the second aspect of the invention may be in the form of a vector, for example, an expression vector, and may include, among others, chromosomal, episomal and virus-derived vectors, for example, vectors derived from bacterial plasmids, from bacteriophage, from transposons, from yeast episomes, from insertion elements, from yeast chromosomal elements, from viruses such as baculo-viruses, papova-viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express nucleic acid to express a polypeptide in a host, may be used for expression in this regard. The vector may comprise a plurality of the nucleic acid constructs defined above, for example 2 or more.

The invention further provides a protein encoded by the nucleic acid construct of the second aspect of the invention optionally in association with latent TGFβ binding protein (LTBP) described herein. Typically, the protein encoded by the nucleic acid construct is covalently linked to LTBP to form a complex. Preferably, the association is mediated by disulphide bond(s) between Cys No. 33 of LAP and the third 8 Cys residue of LTBP.

The nucleic acid construct of the second aspect of the invention preferably includes a promoter or other regulatory sequence which controls expression of the nucleic acid. Promoters and other regulatory sequences which control expression of a nucleic acid have been identified and are known in the art. The person skilled in the art will note that it may not be necessary to utilise the whole promoter or other regulatory sequence. Only the minimum essential regulatory element may be required and, in fact, such elements can be used to construct chimeric sequences or other promoters. The essential requirement is, of course, to retain the tissue and/or temporal specificity. The promoter may be any suitable known promoter, for example, the human cytomegalovirus (CMV) promoter, the CMV immediate early promoter, the HSV thymidine kinase, the early and late SV40 promoters or the promoters of retroviral LTRs, such as those of the Rous Sarcoma virus (RSV) and metallothionine promoters such as the mouse metallothionine-I promoter. The promoter may comprise the minimum comprised for promoter activity (such as a TATA element without enhancer elements) for example, the minimum sequence of the CMV promoter. Preferably, the promoter is contiguous to the first and/or second nucleic acid sequence.

As stated herein, the nucleic acid construct of the second aspect of the invention may be in the form of a vector. Vectors frequently include one or more expression markers which enable selection of cells transfected (or transformed) with them, and preferably, to enable a selection of cells containing vectors incorporating heterologous DNA. A suitable start and stop signal will generally be present.

One embodiment of the invention relates to a cell comprising the nucleic acid construct of the second aspect of the invention. The cell may be termed a "host" cell, which is useful for the manipulation of the nucleic acid, including cloning. Alternatively, the cell may be a cell in which to obtain expression of the nucleic acid. Representative examples of appropriate host cells for expression of the nucleic acid construct of the invention include virus packaging cells which allow encapsulation of the nucleic acid into a viral vector; bacterial cells, such as *Streptococci, Staphylococci, E. coli, Streptomyces* and *Bacillus subtilis*; single cells, such as yeast cells, for example, *Saccharomyces cerevisiae*, and *Aspergillus* cells; insect cells such as *Drosophila* S2 and *Spodoptera* Sf9 cells, animal cells such as CHO, COS, C127, 3T3, PHK.293, and Bowes Melanoma cells and other suitable human cells; and plant cells e.g. *Arabidopsis thaliana*.

Introduction of an expression vector into the host cell can be affected by calcium phosphate transfection, DEAE-dextran mediated transfection, microinjection, cationic—lipid-mediated transfection, electroporation, transduction, scrape loading, ballistic introduction, infection or other methods. Such methods are described in many standard laboratory manuals, such as Sambrook et al, Molecular Cloning, a Laboratory Manual, Second Edition, Coldspring Harbor Laboratory Press, Coldspring Harbor, N.Y. (1989).

Mature proteins can be expressed in host cells, including mammalian cells such as CHO cells, yeast, bacteria, or other cells under the control of appropriate promoters. Cell-free translation systems can be employed to produce such proteins using RNAs derived from the nucleic acid construct of the second aspect of the present invention. Appropriate cloning and expression vectors for use with prokaryotic and eukaryotic hosts are described by Sambrook et al, Molecular Cloning, a Laboratory Manual, Second Edition, Coldspring Harbor Laboratory Press, Coldspring Harbor, N.Y. (1989).

Proteins can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography, high performance liquid chromatography, lectin and/or heparin chromatography. For therapy, the nucleic acid construct e.g. in the form of a recombinant vector, may be purified by techniques known in the art, such as by means of column chromatography as described in Sambrook et al, Molecular Cloning, a Laboratory Manual, Second Edition, Coldspring Harbor Laboratory Press, Coldspring Harbor, N.Y. (1989).

According to a third aspect of the invention, there is provided a composition in accordance with the first aspect of the invention for use in the treatment of inflammatory conditions or cancer. This aspect of the invention therefore extends to and includes a method for the treatment of inflammatory conditions or cancer comprising the administration to a subject of a composition comprising a fusion protein comprising a latency associated protein, a dimerisation domain and a pharmaceutically active agent.

The present invention provides a composition as described above for use in the treatment of inflammatory conditions or cancer. Inflammatory conditions include, without limitation, atherosclerosis, acute and chronic lung inflammation (e.g., chronic bronchitis, asthma, lung infection including bacterial and viral infections such as SARS and influenza, cystic fibrosis, etc.), inflammation of virus-infected tissues (e.g., viral lung infections, viral myocarditis, viral meningitis, etc.), ulcerative colitis, endotoxic shock, arthritis (e.g., rheumatoid arthritis, juvenile arthritis, osteoarthritis, psoriatic arthritis, reactive arthritis, viral or post-viral arthritis, ankylosing spondylarthritis, etc.), psoriasis, Crohn's disease, inflammatory bowel disease, insulin dependent diabetes mellitus, injury independent type II diabetes, ischemia induced inflammation, otitis media (middle ear infection), gout, multiple sclerosis, cachexia, and Ataxia Telangiectasia. Arthritis defines a group of disease conditions (or arthropathies) where damage is caused to the joints of the body and includes osteoarthritis (also known as degenerative joint disease) which can occur following trauma to the joint, following an infection of the joint or as a result of aging. Other forms of arthritis include rheumatoid arthritis and psoriatic arthritis, which are autoimmune diseases, and septic arthritis is caused by infection in the joints. Cancer defines a group of diseases characterized by an abnormal proliferation of cells in the body, which can be defined as tumors, for example glioma. Types of gliomas include ependymomas, astrocytomas, oligodendrogliomas and mixed gliomas. A Grade 4 astrocytoma is also known as a glioblastoma.

In a fourth aspect, the invention provides a nucleic acid sequence in accordance with the second aspect of the invention for use in the treatment of inflammatory conditions or cancer. This aspect therefore extends to and includes a method for the treatment of inflammatory conditions or cancer comprising the administration to a subject a nucleic acid construct of the second aspect of the invention. Where the nucleic acid construct is used in the therapeutic method of the invention, the construct may be used as part of an expression construct, e.g. in the form of an expression vector such as a plasmid or virus. In such a method, the construct may be administered intravenously, intradermally, intramuscularly, orally or by other routes.

The nucleic acid construct of the second aspect of the invention, and proteins derived therefrom, may be employed alone or in conjunction with other compounds, such as therapeutic compounds, e.g. anti-inflammatory drugs, cytotoxic agents, cytostatic agents or antibiotics. The nucleic acid constructs and proteins useful in the present invention are preferably provided in an isolated form, and preferably are purified to homogeneity.

As used herein, the term "treatment" includes any regime that can benefit a human or a non-human animal. The treatment of "non-human animals" extends to the treatment of domestic animals, including horses and companion animals (e.g. cats and dogs) and farm/agricultural animals including members of the ovine, caprine, porcine, bovine and equine families. The treatment may be in respect of any existing condition or disorder, or may be prophylactic (preventive treatment). The treatment may be of an inherited or an acquired disease. The treatment may be of an acute or chronic condition. Preferably, the treatment is of a condition/disorder associated with inflammation. The first nucleic acid sequence of the nucleic acid construct of the third aspect of the invention may encode a protein for use in the treatment of the disorder, including, but not limited to osteoarthritis, scleroderma, renal disease, rheumatoid arthritis, inflammatory bowel disease, multiple sclerosis, atherosclerosis, cancer, or any inflammatory disease.

The nucleic acid construct of the second aspect of the invention may be used therapeutically in a method of the invention by way of gene therapy. Alternatively, protein encoded by the nucleic acid construct may be directly administered as described herein.

Administration of the nucleic acid construct of the second aspect may be directed to the target site by physical methods. Examples of these include topical administration of the "naked" nucleic acid in the form of a vector in an appropriate vehicle, for example, in solution in a pharmaceutically acceptable excipient, such as phosphate buffered saline, or administration of a vector by physical method such as particle bombardment according to methods known in the art.

Other physical methods for administering the nucleic acid construct or proteins of the third aspect of the invention directly to the recipient include ultrasound, electrical stimulation, electroporation and microseeding. Further methods of administration include oral administration or administration through inhalation.

Particularly preferred is the microseeding mode of delivery which is a system for delivering genetic material into cells in situ in a patient. This method is described in U.S. Pat. No. 5,697,901.

The nucleic acid construct according to the second aspect of the invention may also be administered by means of delivery vectors. These include viral delivery vectors, such as adenovirus, retrovirus or lentivirus delivery vectors known in the art. Other non-viral delivery vectors include lipid delivery vectors, including liposome delivery vectors known in the art.

Administration may also take place via transformed host cells. Such cells include cells harvested from the subject, into which the nucleic acid construct is transferred by gene transfer methods known in the art. Followed by the growth of the transformed cells in culture and grafting to the subject.

As used herein the term "gene therapy" refers to the introduction of genes by recombinant genetic engineering of body cells (somatic gene therapy) for the benefit of the patient. Furthermore, gene therapy can be divided into ex vivo and in vivo techniques. Ex vivo gene therapy relates to the removal of body cells from a patient, treatment of the removed cells with a vector i.e., a recombinant vector, and subsequent return of the treated cells to the patient. In vivo gene therapy relates to the direct administration of the recombinant gene vector by, for example, intravenous or intravascular means. Preferably the method of gene therapy of the present invention is carried out ex vivo.

Preferably in gene therapy, the expression vector of the present invention is administered such that it is expressed in the subject to be treated. Thus for human gene therapy, the promoter is preferably a human promoter from a human gene, or from a gene which is typically expressed in humans, such as the promoter from human CMV.

For gene therapy, the present invention may provide a method for manipulating the somatic cells of human and non-human mammals.

The present invention also provides a gene therapy method which may involve the manipulation of the germ line cells of a non-human mammal.

The present invention therefore provides a method for providing a human with a therapeutic protein comprising introducing mammalian cells into a human, the human cells having been treated in vitro to insert therein a nucleic acid construct according to the second aspect of the invention.

Each of the individual steps of the ex vivo somatic gene therapy method are also covered by the present invention. For example, the step of manipulating the cells removed from a patient with the nucleic acid construct of the third aspect of the invention in an appropriate vector. As used herein, the term "manipulated cells" covers cells transfected with a recombinant vector. Also contemplated is the use of the transfected cells in the manufacture of a medicament for the treatment of inflammatory conditions, such as arthritis or cancer, as defined herein above.

The present invention may also find application in veterinary medicine for treatment/prophylaxis of domestic animals including horses and companion animals (e.g. cats and dogs) and farm animals which may include mammals of the ovine, porcine, caprine, bovine and equine families.

The present invention also relates to compositions comprising the nucleic acid construct or proteins of the first or second aspects of the invention. Therefore, the fusion protein or nucleic acid constructs of the present invention may be employed in combination with the pharmaceutically acceptable carrier or carriers. Such carriers may include, but are not limited to, saline, buffered saline, dextrose, liposomes, water, glycerol, ethanol and combinations thereof.

The pharmaceutical compositions of the invention may comprise two fusion proteins according to the first aspect of the invention, wherein the fusion proteins are associated at the dimerisation domain in each fusion protein, or a nucleic acid sequence encoding two fusion proteins according to the first aspect of the invention.

The pharmaceutical compositions may be administered in any effective, convenient manner effective for treating a patient's disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg up to 10 mg/kg body weight, typically around 1 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention References to uses of the fusions proteins, nucleic acid constructs, vectors, or host cells of the present invention in the treatment of diseases, such as inflammatory diseases or cancer, includes embodiments relating to the use of the fusion protein, nucleic acid construct, vector, or host cell in the manufacture of a medicament for the treatment of said diseases.

A fifth aspect of the invention provides a fusion protein comprising a LAP, a pharmaceutically active agent and an amino acid sequence comprising a dimerisation domain, wherein the LAP and the pharmaceutically active agent are connected by an amino acid sequence comprising a proteolytic cleavage site for use in the treatment of inflammatory conditions or cancer. The pharmaceutically active agent may be as described above. In some embodiments of this aspect of the invention, the pharmaceutically active agent may be an siRNA or PNA molecule.

The invention further provides a nucleic acid construct encoding the fusion protein of the fifth aspect of the invention. The nucleic acid construct preferably comprises a nucleic acid sequence encoding a LAP adjacent a nucleic acid sequence encoding a proteolytic cleavage site. Preferably, the nucleic acid sequence encoding a LAP is suitably operably linked to a nucleic acid sequence encoding a proteolytic cleavage site.

The invention further provides the fusion protein of the fifth aspect of the invention optionally in association with latent TGFβ binding protein (LTBP) described herein.

The fusion protein of the fifth aspect of the invention may be associated with the pharmaceutically active agent by means of a peptide bond linkage. Alternatively, the fusion protein may be associated with the pharmaceutically active agent by means of a chemical linkage e.g. by cross-linking the fusion protein to a chemical compound such as a chemotherapeutic agent, synthetic drug or PNA.

Preferably, the pharmaceutically active agent is linked to the C-terminal end of the amino acid sequence of the proteolytic cleavage site in the fusion protein of the seventh aspect of the invention. More preferably, the pharmaceutically active agent is continuous with the C-terminal residue of the amino acid sequence of the proteolytic cleavage site.

The fusion protein, and associated pharmaceutically active agent of the fifth aspect of the invention may be employed alone or in conjunction with other compounds, such as therapeutic compounds, e.g. anti-inflammatory drugs, cytotoxic agents, cytostatic agents or antibiotics. Such administration may be simultaneous, separate or sequential. The components may be prepared in the form of a kit which may comprise instructions as appropriate.

Preferably, the fusion protein and associated pharmaceutically active agent of the fifth aspect of the invention are directly administered to a patient as described herein.

The present invention also relates to compositions comprising the fusion protein and associated pharmaceutically active agent of the fifth aspect of the invention. Therefore, the fusion protein and associated pharmaceutically active agent may be employed in combination with the pharmaceutically acceptable carrier or carriers. Such carriers may include, but are not limited to, saline, buffered saline, dextrose, liposomes, water, glycerol, polyethylene glycol, ethanol and combinations thereof.

The pharmaceutical compositions may be administered in any effective, convenient manner effective for treating a disease of a patient including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

A sixth aspect of the invention provides a kit of parts comprising a fusion protein of the first aspect of the invention, a nucleic acid construct of the second aspect of the invention, or a fusion protein and associated pharmaceutically active agent according to the fifth aspect of the invention, and an administration vehicle including, but not limited to, tablets for oral administration, inhalers for lung administration and injectable solutions for intravenous administration.

A seventh aspect of the invention provides a process for preparing the fusion protein, of the first aspect of the invention comprising production of the fusion protein recombinant by expression in a host cell, purification of the expressed fusion protein and association of the pharmaceutically active agent to the purified fusion protein by means of peptide bond linkage, hydrogen or salt bond or chemical cross linking. In some embodiments of this aspect of the invention where the pharmaceutically active agent is a peptide, the fusion protein could be prepared using hydrogen or salt bonds where the peptide is capable or multimerisation, for example dimerisation or trimerisation.

An eighth aspect of the invention provides a process for preparing a nucleic acid construct of the second aspect of the invention comprising ligating together nucleic acid sequences encoding a latency associated peptide, a proteolytic cleavage sequence, and a pharmaceutically active agent, optionally including a linker sequence on either side of the proteolytic cleavage site.

One embodiment of the present invention provides a method of providing latency to a pharmaceutically active agent which is a cytokine, preferably interferon or an interleukin or a cytokine inhibitor such as a scFV or soluble cytokine receptor, the method comprising constructing a fusion protein having a latency associated peptide, preferably from TGFβ, associated with a proteolytic cleavage site, preferably an ADAM-TS4 cleavage site, and the pharmaceutically active agent. For example, the pharmaceutically active agent may be followed by the proteolytic cleavage site and the LAP as follows: Ig-LAP-cleavage site-active agent.

The present invention therefore enables the formation of a dimer which solves a problem of protein production in suspension cultures. The invention also enables (due to the closure of the "shell" of the LAP construct) the production of latent antibody fragments (e.g. inhibitors of cytokine action) as therapeutic agents. Previously, the fusion of a single peptide therapeutic agent with LAP left the "shell" partially open and thus potentially exposed without the need for release by protease action at the site of disease i.e. MMP/aggrecanase cleavage. For example, where the therapeutic peptide was a cytokine inhibitor, such as a scFv, it could interact if exposed with the cytokine before release at the site of disease.

The present invention can use any type of immunoglobulin (Ig) from any species (as their structure is extremely similar), but for certain clinical applications particular isotypes may be advantageous for example for in mucosal tissues IgA may be used, for binding to Fc receptors IgG2 may be used. Additionally, mutated forms of Fc that prevent them from binding to Fc receptors or activating cell mediated immunity or complement activation could be used if it was desirable for a particular clinical application.

All preferred features of the second and subsequent aspects of the invention are as for the first aspect mutatis mutandis.

The present invention will now be described by way of example only with reference to the accompanying figures wherein:

Figure 1:
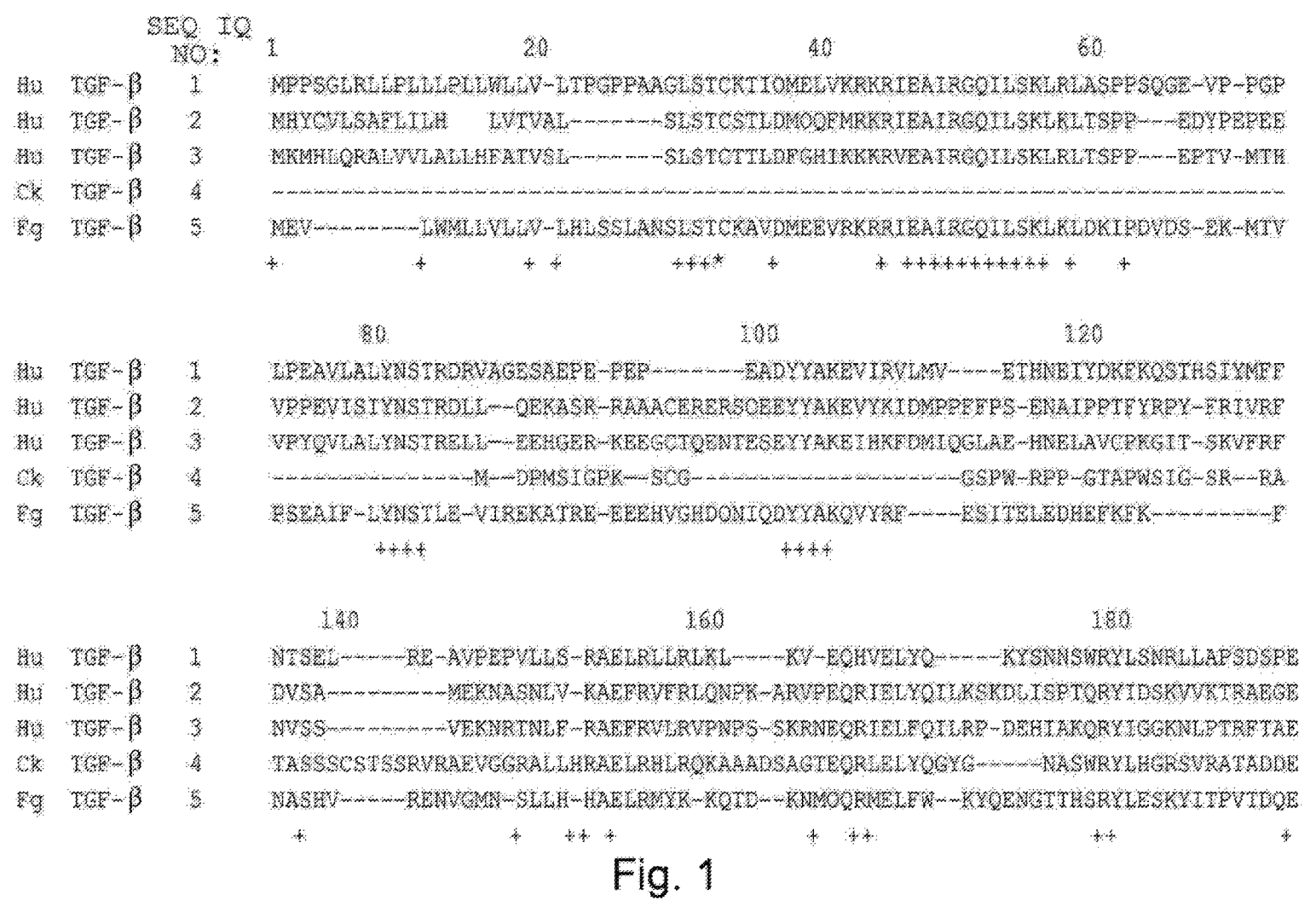
Figure 1:
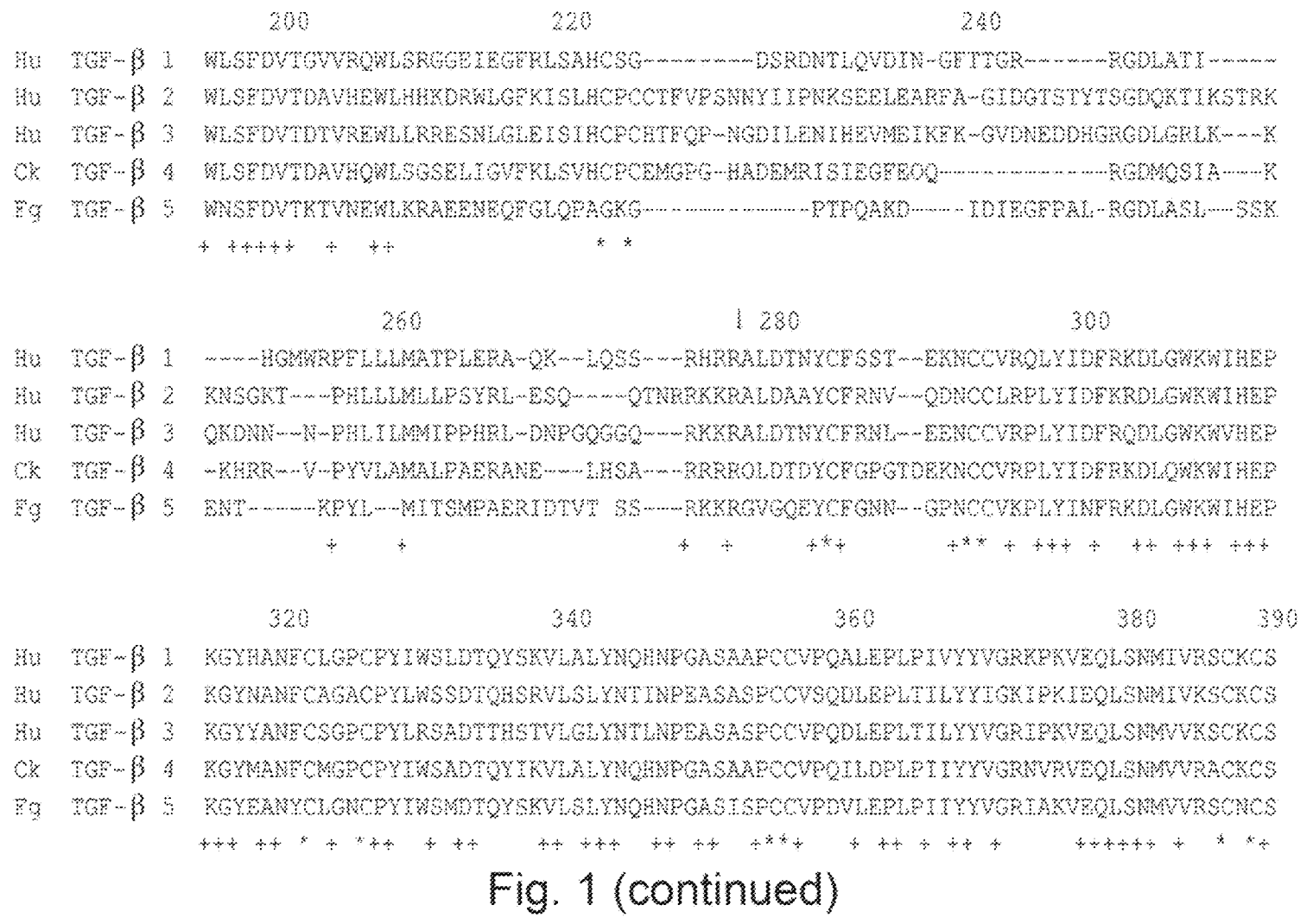

FIG. 1 shows amino acid sequences of the precursor domain of TGFβ 1, 2 and 3 (human, Hu) (SEQ ID NOs:1-3), TGFβ 4 (chicken, Ck) (SEQ ID NO:4), TGFβ (frog, Fg) (SEQ ID NO:5). Arrows indicate the position of the proteolytic processing resulting in cleavage of the signal peptide of TGFβ1 and of the mature TGFβs. N-linked glycosylation sites are underlined, as is the integrin cellular recognition sequence (Roberts and Sporn, Peptide Growth Factors and their Receptors: Sporn, M B and Roberts, A B, Springer-Verlag, Chapter 8, 422 (1996)).

FIG. 2 shows the sequences of protein cleavage sites of matrix metalloproteinases (MMPs) (Nagase and Fields, Biopolymers, 40, 399-416 (1996)) (SEQ ID NOs:6-78).

FIG. 3 shows a multiple sequence alignment of the ADAMTS-4 epitope sequences with corresponding average percentage of phagemid cleavage and the derived ADAMTS-4 cleavage motif. Predominant amino acids found at a frequency of greater than 40% in a particular position are illustrated with a black background, in contrast to related amino acids which are shown with a grey background (reproduced from Hills et al J. Biol. Chem. 282 11101-11109 (2007)) (SEQ ID NOs:79-129).

FIG. 4a shows the theoretical structure of LAP. FIG. 4b shows the theoretical structure of Ig-LAP. FIG. 4c shows a schematic representation of Ig-LAP.

Figure 5:
Figure 5:
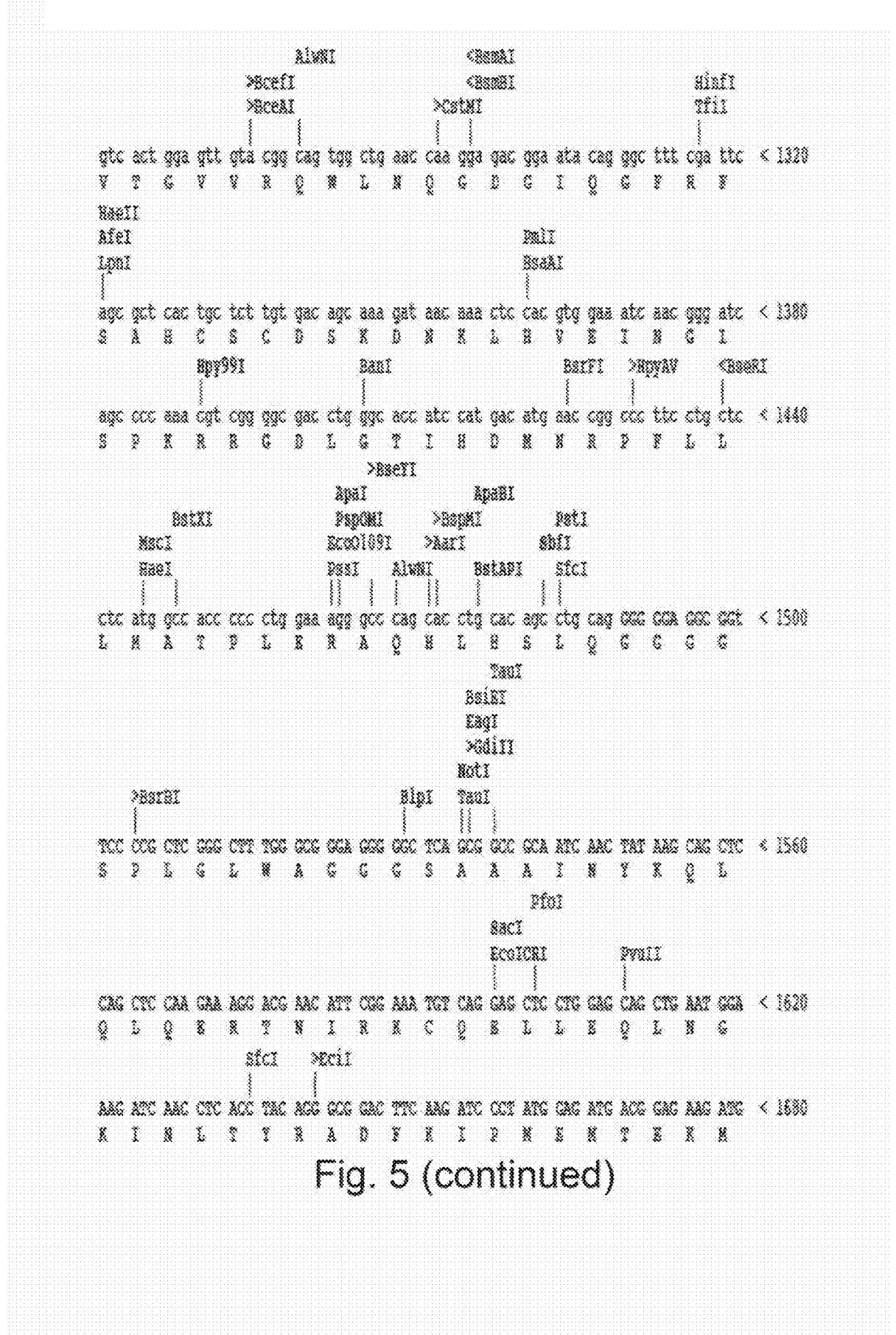

FIG. 5 shows the DNA sequence (SEQ ID NO:130) and predicted amino acid sequence (SEQ ID NO:131) of mouse IgG1(Fc)-LAP-MMP-IFN. Initiator ATG is at position 10 and stop codon at position 2025.

Figure 6:
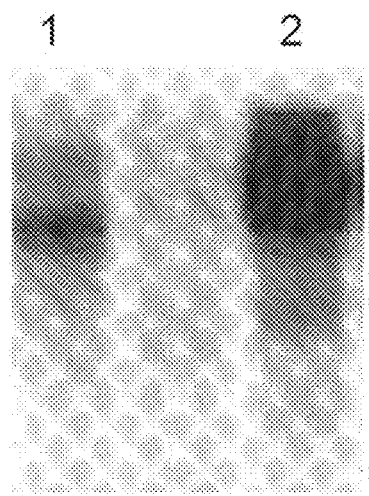

FIG. 6 shows the expression of Ig-LAP-IFN in CHO cells. Western blotting of LAP-IFN (slot 1) or Ig-LAP-IFN (slot 2). 20 μl supernatant from suspension CHO cells was run on 4-12% SDS-PAGE in non-denaturing conditions and blotted onto PDVF membrane. Then probed with goat anti-LAP antibodies. The bands were detected using HRP-conjugated anti-goat antibody by chemiluminescence (ECL, Amersham) and exposed to autoradiography.

Figure 7:
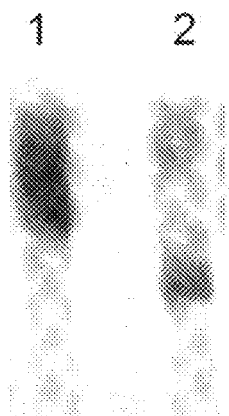

FIG. 7 shows the cleavage of Ig-LAP-IFN by MMP1. 20 μl of CHO cell supernatant was incubated at 37° C. overnight without (slot 1) or with MMP1 (slot 2). The products were then run on a 4-12% SDS-PAGE gradient gel in non-denaturing conditions and blotted to a PDVF membrane. Anti-LAP antibodies were used to detect the uncleaved (slot 1) and cleaved product (slot 2). The molecular weight of the cleaved Ig-LAP corresponds to the expected size of about 160 kDa.

FIG. 8 shows the DNA sequence of human Ig-LAP with anti-herNeu2 (Herceptin™) antibody (SEQ ID NOs:132-134). The cleavage site in this construct is an aggrecanase-specific site. The secretory signal peptide is derived from IL-2 (nucleotides 1-54), the human CH2 and CH3 domains are derived from IgG1 (nucleotides 55-757) and is followed by a spacer with unique restriction sites HindIII and NcoI (nucleotides 758-771) and the human LAP sequence (nucleotides 772-1515) is followed by the aggrecanase cleavage site which is flanked by GGGGS (SEQ ID NO:135) linkers (nucleotides 1516-1584) and finally the Herceptin™ scFv ending in a poly His tail (nucleotides 1585-2370).

Figure 9:
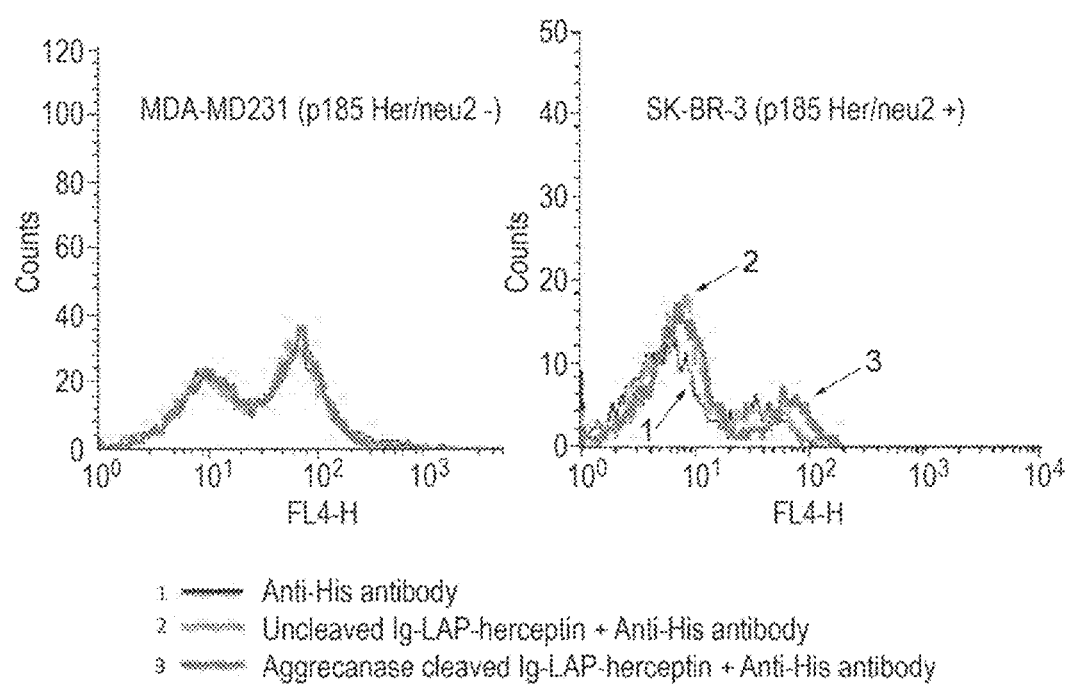

FIG. 9 shows the detection of Herceptin™ by anti-His antibody labelled with a fluorophore. Ig-LAP Herceptin™ was produced in CHO cells in suspension and the fusion protein was purified from cell supernatants by affinity chromatography using a Protein A column. A fraction from the purified material was applied to breast cancer cells expressing Her/neu2 (SKBR3) or non-expressing (MDA-MD-231) before or after cleavage by aggrecanase. Herceptin™ scFv binds to the P185 Her Neu2 on breast cancer cells only after aggrecanase release of Herceptin™ from the hulg-LAP fusion.

The invention is now described with reference to the following non-limiting examples:

EXAMPLE 1: CLONING THE IGG1 FC BETWEEN THE SIGNAL PEPTIDE OF IL-2 AND MOUSE LAP

An example of the preparation of a construct of the invention is as follows. PCR of mouse IgG1 was used for cloning the IgG1 Fc into an EcoR1 site after the signal peptide of muLAP-MMP-IFN. The following oligonucleotides were designed for linking in frame the coding regions.

```
Sense oligo:
                                   (SEQ ID NO: 143)
5' ATG AAT TCC GGT TGT AAG CCTTGCATA Anti-sense oligo:
                                   (SEQ ID NO: 144)
5' GT GA ATT CCT CCA TGG AAG CTT TTT ACC AGG
AGA GTG GGA GAG
```

The EcoR1 sites in the oligos are underlined and the Nco1 and HindIII sites are in bold. These latter sites were introduced to allow for direct cloning of additional MMP or aggrecanase cleavage sites. Because the IgG1 fragment could be inserted on the opposite orientation needed for in-frame translation, the resulting clones were analysed by restriction analysis and these containing the IgG1 fragment in the right orientation sent for DNA sequencing. FIG. 5 depicts the DNA sequence of a representative positive clone.

Ig-LAP-MMP-IFN is effectively secreted from CHO cells grown in suspension:

Supernatant from transiently transfected CHO cells was analysed after non-reducing SDS-PAGE by western blotting using a goat anti-LAP antibody (R&D systems) (FIG. 6). The molecular weight of the Ig-LAP-IFN was bigger than that of LAP-IFN (i.e. above 200 kDa as expected from a glycosylated dimerised protein).

Ig-LAP-Fusion is Cleaved by Recombinant MMP1:

In order to establish whether the Ig-LAP-IFN fusion is still cleavable by MMP the inventors digested the protein in the CHO supernatant with recombinant MMP-1 overnight at 37° C. The reaction was stopped with 25 mM EDTA and then analysed by western blotting after non-denaturing SDS-PAGE (FIG. 7).

After Cleavage with MMP, Ig-LAP-IFN Releases IFN Biological Activity:

Mouse L929 cells were plated at 104 cells/well in 96 well plates. The cells were incubated overnight with supernatants of Ig-LAP-IFN transfected CHO cell cultures that was treated or untreated with MMP-1 at double dilutions starting at 1:10. Then the medium was removed and the cells were infected with encephalomyocarditis virus in a volume of 50 μl for 16 hours as described (Adams et al. 2003). Cells were washed in PBS and 100 ml of Cell titer-Glo (Promega) cell lysis buffer. After 20 minutes and room temperature, 50 μl were transferred to an opaque plate and the luminescence (endogenous ATP levels) read in a Luminometer. 50% cell viability was assessed as half of luciferase activity compared to uninfected L929 cells (see Table 2 which shows MMP cleavage releases IFN activity from Ig-LAP-IFN).

TABLE 2

| Treatment | Luciferase activity | IFN biological activity (U/ml) |
|---|---|---|
| Control No infection | 10973 | N/A |
| Control (+EMC) | 64 | |
| Ig-LAP-IFN (no MMP1) + EMC | 64 | 0 |
| IgLAP-IFN (+MMP) + EMC | 5068 | 30 |

EXAMPLE 2: HUMAN IG-HUMAN LAP WITH ANTI-HERNEU2 (HERCEPTIN™) ANTIBODY

Human Ig-human LAP with anti-herNeu2 (Herceptin™—Markiv et al. BMC Biotechnology 2011, 11:117) antibody construct was created with an aggrecanase-specific cleavage site in CHO cells in suspension (FIG. 8). The secretory signal peptide was derived from IL-2 (nucleotides 1-54), the human CH2 and CH3 domains were derived from IgG1 (nucleotides 55-757). In the construct the human CH2 and CH3 domains are followed by a spacer with unique restriction sites HindIII and Nco1 (nucleotides 758-771). The human LAP sequence (nucleotides 772-1515) is followed by the aggrecanase cleavage site which is flanked by GGGGS linkers (nucleotides 1516-1584). The Herceptin™ scFv ends in a poly His tail (nucleotides 1585-2370). The fusion protein was purified from cell supernatants by affinity chromatography using a Protein A column. A fraction from the purified material was applied to breast cancer cells expressing Her/neu2 (SKBR3) or non-expressing (MDA-MD-231) before or after cleavage by aggrecanase. The bound Herceptin™ was detected by anti-His antibody labelled with a fluorophore (FIG. 9).

The invention claimed is:

1. A protein dimer composed of a pair of fusion proteins, each fusion protein comprising a latency associated peptide (LAP) which is the precursor domain of TGFβ-1, -2, -3, -4 or -5, a pharmaceutically active agent and an amino acid sequence comprising a dimerisation domain composed of a Fc region polypeptide, wherein the LAP and the pharmaceutically active agent are connected by an amino acid sequence comprising a proteolytic cleavage site, and the dimerisation domain is linked to the N-terminal of the LAP and wherein the fusion proteins are associated at the dimerisation domain in each fusion protein and form a closed shell around the pharmaceutically active agent, wherein the pharmaceutically active agent is a cytokine.

2. A protein dimer as claimed in claim 1 wherein the antibody fragment polypeptide is an Fc region polypeptide, an immunoglobulin hinge polypeptide, a CH3 domain polypeptide, a CH4 domain polypeptide, a CH1 domain polypeptide or a CL domain polypeptide.

3. A protein dimer as claimed in claim 1 wherein the Fc region polypeptide is derived from an IgG or IgA antibody.

4. A protein dimer as claimed in claim 1 wherein the dimerisation domain is linked to the latency associated peptide-by a linker sequence.

5. A protein dimer as claimed in claim 1 wherein the proteolytic cleavage site is a matrix metalloproteinase or an aggrecanase cleavage site.

6. A pharmaceutical composition comprising a protein dimer of claim 1.

7. A kit comprising a protein dimer as claimed in claim 1 as an administration vehicle.

* * * * *

SEQUENCE LISTING

<160> NUMBER OF SEQ ID NOS: 144

<210> SEQ ID NO 1
<211> LENGTH: 390
<212> TYPE: PRT
<213> ORGANISM: Homo sapiens

<400> SEQUENCE: 1

```
Met Pro Pro Ser Gly Leu Arg Leu Leu Pro Leu Leu Leu Pro Leu Leu
1               5                   10                  15

Trp Leu Leu Val Leu Thr Pro Gly Pro Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Ile Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Gly Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Trp Arg Pro
                245                 250                 255
```

```
Phe Leu Leu Leu Met Ala Thr Pro Leu Glu Arg Ala Gln Lys Leu Gln
                260                 265                 270

Ser Ser Arg His Arg Arg Ala Leu Asp Thr Asn Tyr Cys Phe Ser Ser
                275                 280                 285

Thr Glu Lys Asn Cys Cys Val Arg Gln Leu Tyr Ile Asp Phe Arg Lys
290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
                340                 345                 350

Ala Pro Cys Cys Val Pro Gln Ala Leu Glu Pro Leu Pro Ile Val Tyr
                355                 360                 365

Tyr Val Gly Arg Lys Pro Lys Val Glu Gln Leu Ser Asn Met Ile Val
                370                 375                 380

Arg Ser Cys Lys Cys Ser
385                 390

<210> SEQ ID NO 2
<211> LENGTH: 414
<212> TYPE: PRT
<213> ORGANISM: Homo sapiens

<400> SEQUENCE: 2

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
                20                  25                  30

Met Arg Lys Arg Ile Glu Ala Ile Arg Gly Gln Ile Leu Ser Lys Leu
                35                  40                  45

Lys Leu Thr Ser Pro Pro Glu Asp Tyr Pro Glu Pro Glu Glu Val Pro
50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
                100                 105                 110

Pro Ser Glu Asn Ala Ile Pro Pro Thr Phe Tyr Arg Pro Tyr Phe Arg
                115                 120                 125

Ile Val Arg Phe Asp Val Ser Ala Met Glu Lys Asn Ala Ser Asn Leu
130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Ile Ser Pro Thr Gln Arg Tyr Ile Asp Ser Lys Val Val Lys Thr
                180                 185                 190

Arg Ala Glu Gly Glu Trp Leu Ser Phe Asp Val Thr Asp Ala Val His
                195                 200                 205

Glu Trp Leu His His Lys Asp Arg Trp Leu Gly Phe Lys Ile Ser Leu
                210                 215                 220

His Cys Pro Cys Cys Thr Phe Val Pro Ser Asn Asn Tyr Ile Ile Pro
```

```
                225                 230                 235                 240

Asn Lys Ser Glu Glu Leu Glu Ala Arg Phe Ala Gly Ile Asp Gly Thr
                        245                 250                 255

Ser Thr Tyr Thr Ser Gly Asp Gln Lys Thr Ile Lys Ser Thr Arg Lys
                        260                 265                 270

Lys Asn Ser Gly Lys Thr Pro His Leu Leu Met Leu Leu Pro Ser
                        275                 280                 285

Tyr Arg Leu Glu Ser Gln Gln Thr Asn Arg Arg Lys Lys Arg Ala Leu
                        290                 295                 300

Asp Ala Ala Tyr Cys Phe Arg Asn Val Gln Asp Asn Cys Cys Leu Arg
        305                 310                 315                 320

Pro Leu Tyr Ile Asp Phe Lys Arg Asp Leu Gly Trp Lys Trp Ile His
                        325                 330                 335

Glu Pro Lys Gly Tyr Asn Ala Asn Phe Cys Ala Gly Ala Cys Pro Tyr
                        340                 345                 350

Leu Trp Ser Ser Asp Thr Gln His Ser Arg Val Leu Ser Leu Tyr Asn
                        355                 360                 365

Thr Ile Asn Pro Glu Ala Ser Ala Ser Pro Cys Cys Val Ser Gln Asp
                        370                 375                 380

Leu Glu Pro Leu Thr Ile Leu Tyr Tyr Ile Gly Lys Ile Pro Lys Ile
        385                 390                 395                 400

Glu Gln Leu Ser Asn Met Ile Val Lys Ser Cys Lys Cys Ser
                        405                 410

<210> SEQ ID NO 3
<211> LENGTH: 412
<212> TYPE: PRT
<213> ORGANISM: Homo sapiens

<400> SEQUENCE: 3

Met Lys Met His Leu Gln Arg Ala Leu Val Val Leu Ala Leu Leu His
        1               5                   10                  15

Phe Ala Thr Val Ser Leu Ser Leu Ser Thr Cys Thr Thr Leu Asp Phe
                        20                  25                  30

Gly His Ile Lys Lys Lys Arg Val Glu Ala Ile Arg Gly Gln Ile Leu
                        35                  40                  45

Ser Lys Leu Arg Leu Thr Ser Pro Pro Glu Pro Thr Val Met Thr His
                        50                  55                  60

Val Pro Tyr Gln Val Leu Ala Leu Tyr Asn Ser Thr Arg Glu Leu Leu
        65                  70                  75                  80

Glu Glu His Gly Glu Arg Lys Glu Gly Cys Thr Gln Glu Asn Thr
                        85                  90                  95

Glu Ser Glu Tyr Tyr Ala Lys Glu Ile His Lys Phe Asp Met Ile Gln
                        100                 105                 110

Gly Leu Ala Glu His Asn Glu Leu Ala Val Cys Pro Lys Gly Ile Thr
                        115                 120                 125

Ser Lys Val Phe Arg Phe Asn Val Ser Ser Val Glu Lys Asn Arg Thr
                        130                 135                 140

Asn Leu Phe Arg Ala Glu Phe Arg Val Leu Arg Val Pro Asn Pro Ser
        145                 150                 155                 160

Ser Lys Arg Asn Glu Gln Arg Ile Glu Leu Phe Gln Ile Leu Arg Pro
                        165                 170                 175

Asp Glu His Ile Ala Lys Gln Arg Tyr Ile Gly Gly Lys Asn Leu Pro
                        180                 185                 190
```

Thr Arg Gly Thr Ala Glu Trp Leu Ser Phe Asp Val Thr Asp Thr Val
            195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
            245                 250                 255

Asp Asp His Gly Arg Gly Asp Leu Gly Arg Leu Lys Lys Gln Lys Asp
            260                 265                 270

Asn Asn Asn Pro His Leu Ile Leu Met Met Ile Pro Pro His Arg Leu
            275                 280                 285

Asp Asn Pro Gly Gln Gly Gln Arg Lys Lys Arg Ala Leu Asp Thr
290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
            325                 330                 335

Lys Gly Tyr Tyr Ala Asn Phe Cys Ser Gly Pro Cys Pro Tyr Leu Arg
            340                 345                 350

Ser Ala Asp Thr Thr His Ser Thr Val Leu Gly Leu Tyr Asn Thr Leu
            355                 360                 365

Asn Pro Glu Ala Ser Ala Ser Pro Cys Cys Val Pro Gln Asp Leu Glu
            370                 375                 380

Pro Leu Thr Ile Leu Tyr Tyr Val Gly Arg Ile Pro Lys Val Glu Gln
385                 390                 395                 400

Leu Ser Asn Met Val Val Lys Ser Cys Lys Cys Ser
                405                 410

<210> SEQ ID NO 4
<211> LENGTH: 304
<212> TYPE: PRT
<213> ORGANISM: Gallus gallus

<400> SEQUENCE: 4

Met Asp Pro Met Ser Ile Gly Pro Lys Ser Cys Gly Ser Pro Trp
1               5                   10                  15

Arg Pro Pro Gly Thr Ala Pro Trp Ser Ile Gly Ser Arg Arg Ala Thr
            20                  25                  30

Ala Ser Ser Ser Cys Ser Thr Ser Ser Arg Val Arg Ala Glu Val Gly
        35                  40                  45

Gly Arg Ala Leu Leu His Arg Ala Glu Leu Arg His Leu Arg Gln Lys
    50                  55                  60

Ala Ala Asp Ser Ala Gly Thr Glu Gln Leu Glu Leu Tyr Gln
65                  70                  75                  80

Gly Tyr Gly Asn Ala Ser Trp Arg Tyr Leu His Gly Arg Ser Val Arg
                85                  90                  95

Ala Thr Ala Asp Asp Glu Trp Leu Ser Phe Asp Val Thr Asp Ala Val
            100                 105                 110

His Gln Trp Leu Ser Gly Ser Glu Leu Ile Gly Val Phe Lys Leu Ser
        115                 120                 125

Val His Cys Pro Cys Glu Met Gly Pro Gly His Ala Asp Glu Met Arg
    130                 135                 140

Ile Ser Ile Glu Gly Phe Glu Gln Gln Arg Gly Asp Met Gln Ser Ile
145                 150                 155                 160

```
Ala Lys Lys His Arg Arg Val Pro Tyr Val Leu Ala Met Ala Leu Pro
            165                 170                 175

Ala Glu Arg Ala Asn Glu Leu His Ser Ala Arg Arg Arg Arg Asp Leu
        180                 185                 190

Asp Thr Asp Tyr Cys Phe Gly Pro Gly Thr Asp Glu Lys Asn Cys Cys
    195                 200                 205

Val Arg Pro Leu Tyr Ile Asp Phe Arg Lys Asp Leu Gln Trp Lys Trp
210                 215                 220

Ile His Glu Pro Lys Gly Tyr Met Ala Asn Phe Cys Met Gly Pro Cys
225                 230                 235                 240

Pro Tyr Ile Trp Ser Ala Asp Thr Gln Tyr Ile Lys Val Leu Ala Leu
                245                 250                 255

Tyr Asn Gln His Asn Pro Gly Ala Ser Ala Ala Pro Cys Cys Val Pro
            260                 265                 270

Gln Ile Leu Asp Pro Leu Pro Ile Ile Tyr Tyr Val Gly Arg Asn Val
        275                 280                 285

Arg Val Glu Gln Leu Ser Asn Met Val Val Arg Ala Cys Lys Cys Ser
    290                 295                 300

<210> SEQ ID NO 5
<211> LENGTH: 383
<212> TYPE: PRT
<213> ORGANISM: Xenopus laevis

<400> SEQUENCE: 5

Met Glu Val Leu Trp Met Leu Leu Val Leu Leu Val Leu His Leu Ser
1               5                   10                  15

Ser Leu Ala Asn Ser Leu Ser Thr Cys Lys Ala Val Asp Met Glu Glu
            20                  25                  30

Val Arg Lys Arg Arg Ile Glu Ala Ile Arg Gly Gln Ile Leu Ser Lys
        35                  40                  45

Leu Lys Leu Asp Lys Ile Pro Asp Val Asp Ser Glu Lys Met Thr Val
    50                  55                  60

Pro Ser Glu Ala Ile Phe Leu Tyr Asn Ser Thr Leu Glu Val Ile Arg
65                  70                  75                  80

Glu Lys Ala Thr Arg Glu Glu Glu His Val Gly His Asp Gln Asn
            85                  90                  95

Ile Gln Asp Tyr Tyr Ala Lys Gln Val Tyr Arg Phe Glu Ser Ile Thr
            100                 105                 110

Glu Leu Glu Asp His Glu Phe Lys Phe Lys Phe Asn Ala Ser His Val
        115                 120                 125

Arg Glu Asn Val Gly Met Asn Ser Leu Leu His His Ala Glu Leu Arg
    130                 135                 140

Met Tyr Lys Lys Gln Thr Asp Lys Asn Met Asp Gln Arg Met Glu Leu
145                 150                 155                 160

Phe Trp Lys Tyr Gln Glu Asn Gly Thr Thr His Ser Arg Tyr Leu Glu
                165                 170                 175

Ser Lys Tyr Ile Thr Pro Val Thr Asp Gln Glu Trp Asn Ser Phe Asp
            180                 185                 190

Val Thr Lys Thr Val Asn Glu Trp Leu Lys Arg Ala Glu Glu Asn Glu
        195                 200                 205

Gln Phe Gly Leu Gln Pro Ala Gly Lys Gly Pro Thr Pro Gln Ala Lys
    210                 215                 220

Asp Ile Asp Ile Glu Gly Phe Pro Ala Leu Arg Gly Asp Leu Ala Ser
```

```
                225                 230                 235                 240
Leu Ser Ser Lys Glu Asn Thr Lys Pro Tyr Leu Met Ile Thr Ser Met
                    245                 250                 255
Pro Ala Glu Arg Ile Asp Thr Val Thr Ser Ser Arg Lys Lys Arg Gly
                260                 265                 270
Val Gly Gln Glu Tyr Cys Phe Gly Asn Asn Gly Pro Asn Cys Cys Val
            275                 280                 285
Lys Pro Leu Tyr Ile Asn Phe Arg Lys Asp Leu Gly Trp Lys Trp Ile
        290                 295                 300
His Glu Pro Lys Gly Tyr Glu Ala Asn Tyr Cys Leu Gly Asn Cys Pro
305                 310                 315                 320
Tyr Ile Trp Ser Met Asp Thr Gln Tyr Ser Lys Val Leu Ser Leu Tyr
                325                 330                 335
Asn Gln His Asn Pro Gly Ala Ser Ile Ser Pro Cys Cys Val Pro Asp
                340                 345                 350
Val Leu Glu Pro Leu Pro Ile Ile Tyr Tyr Val Gly Arg Ile Ala Lys
            355                 360                 365
Val Glu Gln Leu Ser Asn Met Val Val Arg Ser Cys Asn Cys Ser
        370                 375                 380

<210> SEQ ID NO 6
<211> LENGTH: 8
<212> TYPE: PRT
<213> ORGANISM: Homo sapiens

<400> SEQUENCE: 6

Ala Pro Gln Gly Ile Ala Gly Gln
1               5

<210> SEQ ID NO 7
<211> LENGTH: 8
<212> TYPE: PRT
<213> ORGANISM: Homo sapiens

<400> SEQUENCE: 7

Gly Pro Gln Gly Leu Leu Gly Ala
1               5

<210> SEQ ID NO 8
<211> LENGTH: 8
<212> TYPE: PRT
<213> ORGANISM: Homo sapiens

<400> SEQUENCE: 8

Gly Pro Gln Gly Leu Ala Gly Gln
1               5

<210> SEQ ID NO 9
<211> LENGTH: 8
<212> TYPE: PRT
<213> ORGANISM: Homo sapiens

<400> SEQUENCE: 9

Gly Pro Leu Gly Ile Ala Gly Ile
1               5

<210> SEQ ID NO 10
<211> LENGTH: 8
<212> TYPE: PRT
<213> ORGANISM: Homo sapiens
```

<400> SEQUENCE: 10

Gly Pro Glu Gly Leu Arg Val Gly
1               5

<210> SEQ ID NO 11
<211> LENGTH: 8
<212> TYPE: PRT
<213> ORGANISM: Rattus sp.

<400> SEQUENCE: 11

Ala Ala Tyr His Leu Val Ser Gln
1               5

<210> SEQ ID NO 12
<211> LENGTH: 8
<212> TYPE: PRT
<213> ORGANISM: Rattus sp.

<400> SEQUENCE: 12

Met Asp Ala Phe Leu Glu Ser Ser
1               5

<210> SEQ ID NO 13
<211> LENGTH: 8
<212> TYPE: PRT
<213> ORGANISM: Rattus sp.

<400> SEQUENCE: 13

Glu Pro Gln Ala Leu Ala Met Ser
1               5

<210> SEQ ID NO 14
<211> LENGTH: 8
<212> TYPE: PRT
<213> ORGANISM: Rattus sp.

<400> SEQUENCE: 14

Gln Ala Leu Ala Met Ser Ala Ile
1               5

<210> SEQ ID NO 15
<211> LENGTH: 8
<212> TYPE: PRT
<213> ORGANISM: Gallus gallus

<400> SEQUENCE: 15

Pro Ser Tyr Phe Leu Asn Ala Gly
1               5

<210> SEQ ID NO 16
<211> LENGTH: 8
<212> TYPE: PRT
<213> ORGANISM: Homo sapiens

<400> SEQUENCE: 16

Tyr Glu Ala Gly Leu Gly Val Val
1               5

<210> SEQ ID NO 17
<211> LENGTH: 8
<212> TYPE: PRT
<213> ORGANISM: Homo sapiens

<400> SEQUENCE: 17

Ala Gly Leu Gly Val Val Glu Arg
1               5

<210> SEQ ID NO 18
<211> LENGTH: 8
<212> TYPE: PRT
<213> ORGANISM: Homo sapiens

<400> SEQUENCE: 18

Ala Gly Leu Gly Ile Ser Ser Thr
1               5

<210> SEQ ID NO 19
<211> LENGTH: 8
<212> TYPE: PRT
<213> ORGANISM: Homo sapiens

<400> SEQUENCE: 19

Gly Ala Met Phe Leu Glu Ala Ile
1               5

<210> SEQ ID NO 20
<211> LENGTH: 8
<212> TYPE: PRT
<213> ORGANISM: Homo sapiens

<400> SEQUENCE: 20

Ile Pro Glu Asn Phe Phe Gly Val
1               5

<210> SEQ ID NO 21
<211> LENGTH: 8
<212> TYPE: PRT
<213> ORGANISM: Homo sapiens

<400> SEQUENCE: 21

Thr Glu Gly Glu Ala Arg Gly Ser
1               5

<210> SEQ ID NO 22
<211> LENGTH: 8
<212> TYPE: PRT
<213> ORGANISM: Homo sapiens

<400> SEQUENCE: 22

Arg Ala Ile His Ile Gln Ala Glu
1               5

<210> SEQ ID NO 23
<211> LENGTH: 8
<212> TYPE: PRT
<213> ORGANISM: Homo sapiens

<400> SEQUENCE: 23

Leu Arg Ala Tyr Leu Leu Pro Ala
1               5

<210> SEQ ID NO 24
<211> LENGTH: 8
<212> TYPE: PRT
<213> ORGANISM: Cavia porcellus
<220> FEATURE:
<221> NAME/KEY: MOD_RES
<222> LOCATION: (3)..(3)
<223> OTHER INFORMATION: Xaa is Hyp

```
<400> SEQUENCE: 24

Gly Ala Xaa Gly Leu Glx Gly His
1               5

<210> SEQ ID NO 25
<211> LENGTH: 8
<212> TYPE: PRT
<213> ORGANISM: Rattus sp.

<400> SEQUENCE: 25

Gly Pro Gln Gly Val Arg Gly Glu
1               5

<210> SEQ ID NO 26
<211> LENGTH: 8
<212> TYPE: PRT
<213> ORGANISM: Rattus sp.

<400> SEQUENCE: 26

Gly Pro Ala Gly Val Gln Gly Pro
1               5

<210> SEQ ID NO 27
<211> LENGTH: 8
<212> TYPE: PRT
<213> ORGANISM: Rattus sp.
<220> FEATURE:
<221> NAME/KEY: MOD_RES
<222> LOCATION: (6)..(6)
<223> OTHER INFORMATION: Xaa is Hyp

<400> SEQUENCE: 27

Gly Pro Ser Gly Leu Xaa Gly Pro
1               5

<210> SEQ ID NO 28
<211> LENGTH: 8
<212> TYPE: PRT
<213> ORGANISM: Rattus sp.

<400> SEQUENCE: 28

Gly Pro Ala Gly Glu Arg Gly Ser
1               5

<210> SEQ ID NO 29
<211> LENGTH: 8
<212> TYPE: PRT
<213> ORGANISM: Rattus sp.

<400> SEQUENCE: 29

Gly Ala Lys Gly Leu Thr Gly Ser
1               5

<210> SEQ ID NO 30
<211> LENGTH: 8
<212> TYPE: PRT
<213> ORGANISM: Rattus sp.

<400> SEQUENCE: 30

Gly Pro Ala Gly Gln Asp Gly Pro
1               5

<210> SEQ ID NO 31
<211> LENGTH: 8
<212> TYPE: PRT
```

```
<213> ORGANISM: Rattus sp.

<400> SEQUENCE: 31

Gly Pro Ala Gly Phe Ala Gly Pro
1               5

<210> SEQ ID NO 32
<211> LENGTH: 8
<212> TYPE: PRT
<213> ORGANISM: Rattus sp.

<400> SEQUENCE: 32

Gly Pro Ile Gly Asn Val Gly Ala
1               5

<210> SEQ ID NO 33
<211> LENGTH: 8
<212> TYPE: PRT
<213> ORGANISM: Rattus sp.
<220> FEATURE:
<221> NAME/KEY: MOD_RES
<222> LOCATION: (3)..(3)
<223> OTHER INFORMATION: Hyl

<400> SEQUENCE: 33

Gly Pro Lys Gly Ser Arg Gly Ala
1               5

<210> SEQ ID NO 34
<211> LENGTH: 8
<212> TYPE: PRT
<213> ORGANISM: Bos taurus

<400> SEQUENCE: 34

Gly Pro Gln Gly Ile Ala Gly Gln
1               5

<210> SEQ ID NO 35
<211> LENGTH: 8
<212> TYPE: PRT
<213> ORGANISM: Bos taurus

<400> SEQUENCE: 35

Gly Pro Gln Gly Leu Leu Gly Ala
1               5

<210> SEQ ID NO 36
<211> LENGTH: 8
<212> TYPE: PRT
<213> ORGANISM: Homo sapiens

<400> SEQUENCE: 36

Ile Pro Glu Asn Phe Phe Gly Val
1               5

<210> SEQ ID NO 37
<211> LENGTH: 8
<212> TYPE: PRT
<213> ORGANISM: Homo sapiens

<400> SEQUENCE: 37

Pro Pro Gly Ala Tyr His Gly Ala
1               5

<210> SEQ ID NO 38
```

```
<211> LENGTH: 8
<212> TYPE: PRT
<213> ORGANISM: Homo sapiens

<400> SEQUENCE: 38

Arg Ala Ile His Ile Gln Ala Glu
1               5

<210> SEQ ID NO 39
<211> LENGTH: 8
<212> TYPE: PRT
<213> ORGANISM: Homo sapiens

<400> SEQUENCE: 39

Gly Pro His Leu Leu Val Glu Ala
1               5

<210> SEQ ID NO 40
<211> LENGTH: 8
<212> TYPE: PRT
<213> ORGANISM: Homo sapiens

<400> SEQUENCE: 40

Leu Arg Ala Tyr Leu Leu Pro Ala
1               5

<210> SEQ ID NO 41
<211> LENGTH: 8
<212> TYPE: PRT
<213> ORGANISM: Homo sapiens

<400> SEQUENCE: 41

Gly Pro Glu Gly Leu Arg Val Gly
1               5

<210> SEQ ID NO 42
<211> LENGTH: 8
<212> TYPE: PRT
<213> ORGANISM: Homo sapiens

<400> SEQUENCE: 42

Arg Val Gly Phe Tyr Glu Ser Asp
1               5

<210> SEQ ID NO 43
<211> LENGTH: 8
<212> TYPE: PRT
<213> ORGANISM: Homo sapiens

<400> SEQUENCE: 43

Leu Leu Ser Ala Leu Val Glu Thr
1               5

<210> SEQ ID NO 44
<211> LENGTH: 8
<212> TYPE: PRT
<213> ORGANISM: Homo sapiens

<400> SEQUENCE: 44

Glu Ala Ile Pro Met Ser Ile Pro
1               5

<210> SEQ ID NO 45
<211> LENGTH: 8
<212> TYPE: PRT
```

```
<213> ORGANISM: Homo sapiens

<400> SEQUENCE: 45

Ile Ala Gly Arg Ser Leu Asn Pro
1               5

<210> SEQ ID NO 46
<211> LENGTH: 8
<212> TYPE: PRT
<213> ORGANISM: Gallus gallus

<400> SEQUENCE: 46

Leu Asn Ala Gly Phe Thr Ala Ser
1               5

<210> SEQ ID NO 47
<211> LENGTH: 8
<212> TYPE: PRT
<213> ORGANISM: Homo sapiens

<400> SEQUENCE: 47

Ile Pro Glu Asn Phe Phe Gly Val
1               5

<210> SEQ ID NO 48
<211> LENGTH: 8
<212> TYPE: PRT
<213> ORGANISM: Homo sapiens

<400> SEQUENCE: 48

Lys Pro Gln Gln Phe Phe Gly Leu
1               5

<210> SEQ ID NO 49
<211> LENGTH: 8
<212> TYPE: PRT
<213> ORGANISM: Homo sapiens

<400> SEQUENCE: 49

Asp Val Ala Gln Phe Val Leu Thr
1               5

<210> SEQ ID NO 50
<211> LENGTH: 8
<212> TYPE: PRT
<213> ORGANISM: Homo sapiens

<400> SEQUENCE: 50

Asp Thr Leu Glu Val Met Arg Lys
1               5

<210> SEQ ID NO 51
<211> LENGTH: 8
<212> TYPE: PRT
<213> ORGANISM: Homo sapiens

<400> SEQUENCE: 51

Asp Val Gly His Phe Arg Thr Phe
1               5

<210> SEQ ID NO 52
<211> LENGTH: 8
<212> TYPE: PRT
<213> ORGANISM: Homo sapiens
```

<400> SEQUENCE: 52

Asp Ser Gly Gly Phe Met Leu Thr
1               5

<210> SEQ ID NO 53
<211> LENGTH: 8
<212> TYPE: PRT
<213> ORGANISM: Homo sapiens

<400> SEQUENCE: 53

Arg Val Ala Glu Met Arg Gly Glu
1               5

<210> SEQ ID NO 54
<211> LENGTH: 8
<212> TYPE: PRT
<213> ORGANISM: Homo sapiens

<400> SEQUENCE: 54

Asp Leu Gly Arg Phe Gln Thr Phe
1               5

<210> SEQ ID NO 55
<211> LENGTH: 8
<212> TYPE: PRT
<213> ORGANISM: Homo sapiens

<400> SEQUENCE: 55

Pro Phe Ser Pro Leu Val Ala Thr
1               5

<210> SEQ ID NO 56
<211> LENGTH: 8
<212> TYPE: PRT
<213> ORGANISM: Homo sapiens

<400> SEQUENCE: 56

Leu Arg Ala Tyr Leu Leu Pro Ala
1               5

<210> SEQ ID NO 57
<211> LENGTH: 8
<212> TYPE: PRT
<213> ORGANISM: Homo sapiens

<400> SEQUENCE: 57

Ala Pro Gly Asn Ala Ser Glu Ser
1               5

<210> SEQ ID NO 58
<211> LENGTH: 8
<212> TYPE: PRT
<213> ORGANISM: Homo sapiens

<400> SEQUENCE: 58

Phe Ser Ser Glu Ser Lys Arg Glu
1               5

<210> SEQ ID NO 59
<211> LENGTH: 8
<212> TYPE: PRT
<213> ORGANISM: Bos taurus

<400> SEQUENCE: 59

Ala Gly Gly Ala Gln Met Gly Val
1               5

<210> SEQ ID NO 60
<211> LENGTH: 8
<212> TYPE: PRT
<213> ORGANISM: Bos taurus

<400> SEQUENCE: 60

Gln Met Gly Val Met Gln Gly Pro
1               5

<210> SEQ ID NO 61
<211> LENGTH: 8
<212> TYPE: PRT
<213> ORGANISM: Bos taurus

<400> SEQUENCE: 61

Met Ala Ala Ser Leu Lys Arg Pro
1               5

<210> SEQ ID NO 62
<211> LENGTH: 4
<212> TYPE: PRT
<213> ORGANISM: Bos taurus

<400> SEQUENCE: 62

Ala Lys Arg Glu
1

<210> SEQ ID NO 63
<211> LENGTH: 4
<212> TYPE: PRT
<213> ORGANISM: Bos taurus

<400> SEQUENCE: 63

Leu Arg Lys Pro
1

<210> SEQ ID NO 64
<211> LENGTH: 8
<212> TYPE: PRT
<213> ORGANISM: Bos taurus

<400> SEQUENCE: 64

Gln Ala Gln Ala Ile Leu Gln Gln
1               5

<210> SEQ ID NO 65
<211> LENGTH: 8
<212> TYPE: PRT
<213> ORGANISM: Homo sapiens

<400> SEQUENCE: 65

Arg Ala Ile His Ile Gln Ala Glu
1               5

<210> SEQ ID NO 66
<211> LENGTH: 8
<212> TYPE: PRT
<213> ORGANISM: Bos taurus

<400> SEQUENCE: 66

Leu Val Glu Ala Leu Tyr Leu Val
1               5

```
<210> SEQ ID NO 67
<211> LENGTH: 8
<212> TYPE: PRT
<213> ORGANISM: Bos taurus

<400> SEQUENCE: 67

Glu Ala Leu Tyr Leu Val Cys Gly
1               5

<210> SEQ ID NO 68
<211> LENGTH: 8
<212> TYPE: PRT
<213> ORGANISM: Homo sapiens

<400> SEQUENCE: 68

Ile Pro Glu Asn Phe Phe Gly Val
1               5

<210> SEQ ID NO 69
<211> LENGTH: 8
<212> TYPE: PRT
<213> ORGANISM: Homo sapiens

<400> SEQUENCE: 69

Gly Pro His Leu Leu Val Glu Ala
1               5

<210> SEQ ID NO 70
<211> LENGTH: 8
<212> TYPE: PRT
<213> ORGANISM: Homo sapiens

<400> SEQUENCE: 70

Pro Pro Glu Glu Leu Lys Phe Gln
1               5

<210> SEQ ID NO 71
<211> LENGTH: 8
<212> TYPE: PRT
<213> ORGANISM: Homo sapiens

<400> SEQUENCE: 71

Gly Pro Pro Gly Val Val Gly Pro
1               5

<210> SEQ ID NO 72
<211> LENGTH: 8
<212> TYPE: PRT
<213> ORGANISM: Homo sapiens

<400> SEQUENCE: 72

Gly Pro Pro Gly Leu Arg Gly Glu
1               5

<210> SEQ ID NO 73
<211> LENGTH: 8
<212> TYPE: PRT
<213> ORGANISM: Homo sapiens

<400> SEQUENCE: 73

Gly Pro Gly Gly Val Val Gly Glu
1               5
```

```
<210> SEQ ID NO 74
<211> LENGTH: 8
<212> TYPE: PRT
<213> ORGANISM: Homo sapiens

<400> SEQUENCE: 74

Ile Pro Glu Asn Phe Phe Gly Val
1               5

<210> SEQ ID NO 75
<211> LENGTH: 8
<212> TYPE: PRT
<213> ORGANISM: Homo sapiens

<400> SEQUENCE: 75

Pro Pro Gly Ala Tyr His Gly Ala
1               5

<210> SEQ ID NO 76
<211> LENGTH: 8
<212> TYPE: PRT
<213> ORGANISM: Homo sapiens

<400> SEQUENCE: 76

Arg Ala Ile His Ile Gln Ala Glu
1               5

<210> SEQ ID NO 77
<211> LENGTH: 8
<212> TYPE: PRT
<213> ORGANISM: Homo sapiens

<400> SEQUENCE: 77

Arg Ala Ile His Ile Gln Ala Glu
1               5

<210> SEQ ID NO 78
<211> LENGTH: 8
<212> TYPE: PRT
<213> ORGANISM: Homo sapiens

<400> SEQUENCE: 78

Gly Pro His Leu Leu Val Glu Ala
1               5

<210> SEQ ID NO 79
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 79

Met Met Phe Lys Gly Gln Arg Val Glu Arg Val Leu Thr
1               5                   10

<210> SEQ ID NO 80
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 80
```

```
His Asn Glu Phe Arg Gln Arg Glu Thr Tyr Met Val Phe
1               5                   10
```

<210> SEQ ID NO 81
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 81

```
Asn Trp Gln Glu Phe Gln Ala Lys Arg Ser Val Ala Tyr
1               5                   10
```

<210> SEQ ID NO 82
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 82

```
Leu Glu Leu Lys Ser Asn Ser Val Ile Met Arg Trp Pro
1               5                   10
```

<210> SEQ ID NO 83
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 83

```
Asp Tyr Met Glu Val Arg Arg Gln Met Ser Met Gln Met
1               5                   10
```

<210> SEQ ID NO 84
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 84

```
Ala Leu Glu Met Arg Ala Ala Asp Val Glu Tyr His Phe
1               5                   10
```

<210> SEQ ID NO 85
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 85

```
Val Glu His Leu Met Glu Val Gln Arg Lys Thr Thr Trp
1               5                   10
```

<210> SEQ ID NO 86
<211> LENGTH: 13
<212> TYPE: PRT
<213> ORGANISM: Artificial sequence
<220> FEATURE:

<223> OTHER INFORMATION: Synthetic sequence: Protein cleavage site of
      ADAMTS-4 (aggrecanase-1)

<400> SEQUENCE: 86

Gly Val Glu Val Lys Arg Gln Leu Ser Tyr His Tyr Met
1               5                   10

<210> SEQ ID NO 87
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 87

Gln Glu Leu Val Gly Ala Asn Ile Glu Thr Tyr Met Leu
1               5                   10

<210> SEQ ID NO 88
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 88

Gln Gln Met Glu Val Ser Arg Tyr Val Gln Tyr Lys Trp
1               5                   10

<210> SEQ ID NO 89
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 89

Leu Gln Ser Phe Arg Gln Ala Pro Val Asp Ile Trp Trp
1               5                   10

<210> SEQ ID NO 90
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 90

Gln Glu Leu Arg Gly Lys Ile Ser Ile Gln Pro Phe Lys
1               5                   10

<210> SEQ ID NO 91
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 91

Gln Gln Glu Tyr Met Ser Gly Gln Tyr Asp Ile Ile Phe
1               5                   10

```
<210> SEQ ID NO 92
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 92

Ser Met Glu Phe Ala Ala Thr Val Thr Ser Thr Phe Glu
1               5                   10

<210> SEQ ID NO 93
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 93

Glu Gln Gln Leu Lys Gly Arg Gln Thr His Ile Ile Ile
1               5                   10

<210> SEQ ID NO 94
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 94

Met Glu Leu Lys Gly Gln Thr Asp Met Phe Tyr Ile Ile
1               5                   10

<210> SEQ ID NO 95
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 95

Gly Ala Tyr Ala Val Gly Arg Trp Ser Tyr Val Asp Ala
1               5                   10

<210> SEQ ID NO 96
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 96

Gly Gln Phe Ala Thr Ser Pro Lys Ile Thr Ile His Lys
1               5                   10

<210> SEQ ID NO 97
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 97
```

```
Asp Val Gln Glu Phe Arg Gly Val Thr Ala Val Ile Arg
1               5                   10
```

<210> SEQ ID NO 98
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 98

```
His Glu Ala Arg Thr Val Ser Thr Thr Tyr Leu Met Leu
1               5                   10
```

<210> SEQ ID NO 99
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 99

```
Tyr Met Glu Met Arg Gly Ser Thr Thr Val Phe Phe Asn
1               5                   10
```

<210> SEQ ID NO 100
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 100

```
Gln Glu Leu Ile Gly Ser Tyr Ser Val Met Pro Thr Asn
1               5                   10
```

<210> SEQ ID NO 101
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 101

```
His Tyr Tyr Met Glu Ala Thr Arg Asp Ile Glu Met Val
1               5                   10
```

<210> SEQ ID NO 102
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 102

```
Asn Glu Ala His Ser Ser Gly Ile Thr Ile Met Leu Arg
1               5                   10
```

<210> SEQ ID NO 103
<211> LENGTH: 13
<212> TYPE: PRT
<213> ORGANISM: Artificial sequence

```
<220> FEATURE:
<223> OTHER INFORMATION: Synthetic sequence: Protein cleavage site of
      ADAMTS-4 (aggrecanase-1)

<400> SEQUENCE: 103

Asp His Pro Met Glu Phe Arg Ser Lys Ile Thr Met Lys
1               5                   10

<210> SEQ ID NO 104
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 104

Thr Phe Ala Glu Met Lys Gly Thr Val Ser Tyr Ala Leu
1               5                   10

<210> SEQ ID NO 105
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 105

Gly Val His Met Glu Ser Met Arg Arg Tyr Thr Val Ile
1               5                   10

<210> SEQ ID NO 106
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 106

Phe Gln Glu Tyr Thr Gly Thr Tyr Asp Ile Met Asp Pro
1               5                   10

<210> SEQ ID NO 107
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 107

Phe Gln Ala Val Glu Ala Ser Lys Thr Leu His Phe Trp
1               5                   10

<210> SEQ ID NO 108
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 108

Tyr Leu Glu Thr Ser Arg Thr Tyr Thr Thr Val Trp Pro
1               5                   10
```

<210> SEQ ID NO 109
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 109

Thr Asp Tyr Leu Glu Val Arg Ser Gln Pro Ile Ile Tyr
1               5                   10

<210> SEQ ID NO 110
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 110

Thr Phe Glu Gln Glu Val Arg Ala Pro Asn Ile Ser Trp
1               5                   10

<210> SEQ ID NO 111
<211> LENGTH: 12
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 111

Pro Gln Glu Val Gln Gly Ile Ala Val Glu Trp Val
1               5                   10

<210> SEQ ID NO 112
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 112

Ala Glu Ala Lys Ala Ser Thr Leu His Val Tyr Leu Met
1               5                   10

<210> SEQ ID NO 113
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 113

Asp Tyr Met Glu Val Val Gly Asn Lys Ile Ser Tyr Ile
1               5                   10

<210> SEQ ID NO 114
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

```
<400> SEQUENCE: 114

Val Ile Met Glu Ala Val Gly Arg Lys Thr Ile Leu Gln
1               5                   10

<210> SEQ ID NO 115
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 115

Phe Gln Ala Glu Ala Ala Arg Ala Val Thr Tyr Ser Ser
1               5                   10

<210> SEQ ID NO 116
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 116

Glu Asp Tyr Val Tyr Val Lys Asp Val Gly Thr Thr Asn
1               5                   10

<210> SEQ ID NO 117
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 117

Gln Glu Tyr Lys Ala His His Ser Tyr Lys Leu Met Ser
1               5                   10

<210> SEQ ID NO 118
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 118

Tyr Asn Glu Tyr Arg Ala Thr Pro Thr Phe Ala Val Val
1               5                   10

<210> SEQ ID NO 119
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 119

Glu Tyr Phe His Ala Asn Thr Thr Arg Ile Val Gln Ser
1               5                   10

<210> SEQ ID NO 120
<211> LENGTH: 13
<212> TYPE: PRT
```

```
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 120

Ala Leu Glu Ala Ser Arg Phe Ile Ser Trp Asp Ile Asn
1               5                   10

<210> SEQ ID NO 121
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 121

Trp Glu Ala Val Ala Ala Pro Ile Met His Thr Trp Val
1               5                   10

<210> SEQ ID NO 122
<211> LENGTH: 12
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 122

Phe Gln Glu Leu Lys Ala Ala Glu Thr Phe Trp Met
1               5                   10

<210> SEQ ID NO 123
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 123

Asn Thr Leu Tyr Ala Val Ala Pro Pro Val Ile Tyr Val
1               5                   10

<210> SEQ ID NO 124
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 124

Phe Gln Pro Tyr Glu Val Gln Arg Ile Thr Thr Val Met
1               5                   10

<210> SEQ ID NO 125
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 125

Lys Pro Met Glu Ser Gly Arg Arg Thr Thr Val Tyr Tyr
1               5                   10
```

```
<210> SEQ ID NO 126
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 126

Met Glu Phe Lys Gly Ala Leu Gln Tyr Arg Leu Gln Pro
1               5                   10

<210> SEQ ID NO 127
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 127

Pro Gln Glu Val Lys Gln Ala Arg Lys Trp Ile Ile Glu
1               5                   10

<210> SEQ ID NO 128
<211> LENGTH: 13
<212> TYPE: PRT
<213> ORGANISM: Artificial sequence
<220> FEATURE:
<223> OTHER INFORMATION: Synthetic sequence: Protein cleavage site of
      ADAMTS-4 (aggrecanase-1)

<400> SEQUENCE: 128

Tyr Arg Gln Gln Glu Val Lys Arg His Ile Gln Ile Val
1               5                   10

<210> SEQ ID NO 129
<211> LENGTH: 9
<212> TYPE: PRT
<213> ORGANISM: Artificial sequence
<220> FEATURE:
<223> OTHER INFORMATION: Synthetic sequence: Consensus ADAMTS-4 cleavage
      motif
<220> FEATURE:
<221> NAME/KEY: VARIANT
<222> LOCATION: (2)..(2)
<223> OTHER INFORMATION: Xaa is Ala, Phe, Val, Leu, Met, or Tyr
<220> FEATURE:
<221> NAME/KEY: VARIANT
<222> LOCATION: (3)..(3)
<223> OTHER INFORMATION: May be present or absent. If present, Xaa
      indicates no obvious consensus
<220> FEATURE:
<221> NAME/KEY: VARIANT
<222> LOCATION: (4)..(4)
<223> OTHER INFORMATION: Xaa is Arg or Lys
<220> FEATURE:
<221> NAME/KEY: VARIANT
<222> LOCATION: (5)..(7)
<223> OTHER INFORMATION: Any 1 Xaa may be present or absent: represents
      a range of 2-3 amino acids. If present, Xaa indicates no obvious
      consensus
<220> FEATURE:
<221> NAME/KEY: VARIANT
<222> LOCATION: (8)..(8)
<223> OTHER INFORMATION: Xaa is Ser or Thr
<220> FEATURE:
<221> NAME/KEY: VARIANT
<222> LOCATION: (9)..(9)
<223> OTHER INFORMATION: Xaa is Val, Tyr, Ile, Phe, Trp, Met, Leu, or
      Ala
```

<400> SEQUENCE: 129

Glu Xaa Xaa Xaa Xaa Xaa Xaa Xaa
1               5

<210> SEQ ID NO 130
<211> LENGTH: 2037
<212> TYPE: DNA
<213> ORGANISM: Artificial sequence
<220> FEATURE:
<223> OTHER INFORMATION: Synthetic sequence: Mouse lG1(Fc)-LAP-MMP-IFN
<220> FEATURE:
<221> NAME/KEY: CDS
<222> LOCATION: (1)..(2028)

<400> SEQUENCE: 130

| | | | | | | | | | | | | | | | |
|---|---|---|---|---|---|---|---|---|---|---|---|---|---|---|---|
| gga | tcc | acc | atg | tac | agg | atg | caa | ctc | ctg | tgc | att | gca | cta | agt | ctt | 48 |
| Gly | Ser | Thr | Met | Tyr | Arg | Met | Gln | Leu | Leu | Cys | Ile | Ala | Leu | Ser | Leu |
| 1 | | | | 5 | | | | | 10 | | | | | 15 | |
| gca | ctt | gtc | acg | aat | tcc | ggt | tgt | aag | cct | tgc | ata | tgt | aca | gtc | cca | 96 |
| Ala | Leu | Val | Thr | Asn | Ser | Gly | Cys | Lys | Pro | Cys | Ile | Cys | Thr | Val | Pro |
| | | | 20 | | | | | 25 | | | | | 30 | | |
| gaa | gta | tca | tct | gtc | ttc | atc | ttc | ccc | cca | aag | ccc | aag | gat | gtg | ctc | 144 |
| Glu | Val | Ser | Ser | Val | Phe | Ile | Phe | Pro | Pro | Lys | Pro | Lys | Asp | Val | Leu |
| | | 35 | | | | | 40 | | | | | 45 | | | |
| acc | att | act | ctg | act | cct | aag | gtc | acg | tgt | gtt | gtg | gta | gac | atc | agc | 192 |
| Thr | Ile | Thr | Leu | Thr | Pro | Lys | Val | Thr | Cys | Val | Val | Val | Asp | Ile | Ser |
| 50 | | | | | 55 | | | | | 60 | | | | | |
| aag | gat | gat | ccc | gag | gtc | cag | ttc | agc | tgg | ttt | gta | gat | gat | gtg | gag | 240 |
| Lys | Asp | Asp | Pro | Glu | Val | Gln | Phe | Ser | Trp | Phe | Val | Asp | Asp | Val | Glu |
| 65 | | | | | 70 | | | | | 75 | | | | | 80 |
| gtg | cac | aca | gct | cag | acg | caa | ccc | cgg | gag | gag | cag | ttc | aac | agc | act | 288 |
| Val | His | Thr | Ala | Gln | Thr | Gln | Pro | Arg | Glu | Glu | Gln | Phe | Asn | Ser | Thr |
| | | | | 85 | | | | | 90 | | | | | 95 | |
| ttc | cgc | tca | gtc | agt | gaa | ctt | ccc | atc | atg | cac | cag | gac | tgg | ctc | aat | 336 |
| Phe | Arg | Ser | Val | Ser | Glu | Leu | Pro | Ile | Met | His | Gln | Asp | Trp | Leu | Asn |
| | | | 100 | | | | | 105 | | | | | 110 | | |
| ggc | aag | gag | ttc | aaa | tgc | agg | gtc | aac | agt | gca | gct | ttc | cct | gcc | ccc | 384 |
| Gly | Lys | Glu | Phe | Lys | Cys | Arg | Val | Asn | Ser | Ala | Ala | Phe | Pro | Ala | Pro |
| | | 115 | | | | | 120 | | | | | 125 | | | |
| atc | gag | aaa | acc | atc | tcc | aaa | acc | aaa | ggc | aga | ccg | aag | gct | cca | cag | 432 |
| Ile | Glu | Lys | Thr | Ile | Ser | Lys | Thr | Lys | Gly | Arg | Pro | Lys | Ala | Pro | Gln |
| 130 | | | | | 135 | | | | | 140 | | | | | |
| gtg | tac | acc | att | cca | cct | ccc | aag | gag | cag | atg | gcc | aag | gat | aaa | gtc | 480 |
| Val | Tyr | Thr | Ile | Pro | Pro | Pro | Lys | Glu | Gln | Met | Ala | Lys | Asp | Lys | Val |
| 145 | | | | | 150 | | | | | 155 | | | | | 160 |
| agt | ctg | acc | tgc | atg | ata | aca | gac | ttc | ttc | cct | gaa | gac | att | act | gtg | 528 |
| Ser | Leu | Thr | Cys | Met | Ile | Thr | Asp | Phe | Phe | Pro | Glu | Asp | Ile | Thr | Val |
| | | | | 165 | | | | | 170 | | | | | 175 | |
| gag | tgg | cag | tgg | aat | ggg | cag | cca | gcg | gag | aac | tac | aag | aac | act | cag | 576 |
| Glu | Trp | Gln | Trp | Asn | Gly | Gln | Pro | Ala | Glu | Asn | Tyr | Lys | Asn | Thr | Gln |
| | | | 180 | | | | | 185 | | | | | 190 | | |
| ccc | atc | atg | gac | aca | gat | ggc | tct | tac | ttc | gtc | tac | agc | aag | ctc | aat | 624 |
| Pro | Ile | Met | Asp | Thr | Asp | Gly | Ser | Tyr | Phe | Val | Tyr | Ser | Lys | Leu | Asn |
| | | 195 | | | | | 200 | | | | | 205 | | | |
| gtg | cag | aag | agc | aac | tgg | gag | gca | gga | aat | act | ttc | acc | tgc | tct | gtg | 672 |
| Val | Gln | Lys | Ser | Asn | Trp | Glu | Ala | Gly | Asn | Thr | Phe | Thr | Cys | Ser | Val |
| 210 | | | | | 215 | | | | | 220 | | | | | |
| tta | cat | gag | ggc | ctg | cac | aac | cac | cat | act | gag | aag | agc | ctc | tcc | cac | 720 |
| Leu | His | Glu | Gly | Leu | His | Asn | His | His | Thr | Glu | Lys | Ser | Leu | Ser | His |
| 225 | | | | | 230 | | | | | 235 | | | | | 240 |

-continued

| | |
|---|---|
| tct cct ggt aaa aag ctt cca tgg agg aat tcc tcc acc agc aag acc<br>Ser Pro Gly Lys Lys Leu Pro Trp Arg Asn Ser Ser Thr Ser Lys Thr<br>245 250 255 | 768 |
| atc gac atg gag ctg gtg aaa cgg aag cgc atc gaa gcc atc cgt ggc<br>Ile Asp Met Glu Leu Val Lys Arg Lys Arg Ile Glu Ala Ile Arg Gly<br>260 265 270 | 816 |
| cag atc ctg tcc aaa cta agg ctc gcc agt ccc cca agc cag ggg gag<br>Gln Ile Leu Ser Lys Leu Arg Leu Ala Ser Pro Pro Ser Gln Gly Glu<br>275 280 285 | 864 |
| gta ccg ccc ggc ccg ctg ccc gag gcg gtg ctc gct ttg tac aac agc<br>Val Pro Pro Gly Pro Leu Pro Glu Ala Val Leu Ala Leu Tyr Asn Ser<br>290 295 300 | 912 |
| acc cgc gac cgg gtg gca ggc gag agc gcc gac cca gag ccg gag ccc<br>Thr Arg Asp Arg Val Ala Gly Glu Ser Ala Asp Pro Glu Pro Glu Pro<br>305 310 315 320 | 960 |
| gaa gcg gac tac tat gct aaa gag gtc acc cgc gtg cta atg gtg gac<br>Glu Ala Asp Tyr Tyr Ala Lys Glu Val Thr Arg Val Leu Met Val Asp<br>325 330 335 | 1008 |
| cgc aac aac gcc atc tat gag aaa acc aaa gac atc tca cac agt ata<br>Arg Asn Asn Ala Ile Tyr Glu Lys Thr Lys Asp Ile Ser His Ser Ile<br>340 345 350 | 1056 |
| tat atg ttc ttc aat acg tca gac att cgg gaa gca gtg ccc gaa ccc<br>Tyr Met Phe Phe Asn Thr Ser Asp Ile Arg Glu Ala Val Pro Glu Pro<br>355 360 365 | 1104 |
| cca ttg ctg tcc cgt gca gag ctg cgc ttg cag aga tta aaa tca agt<br>Pro Leu Leu Ser Arg Ala Glu Leu Arg Leu Gln Arg Leu Lys Ser Ser<br>370 375 380 | 1152 |
| gtg gag caa cat gtg gaa ctc tac cag aaa tat agc aac aat tcc tgg<br>Val Glu Gln His Val Glu Leu Tyr Gln Lys Tyr Ser Asn Asn Ser Trp<br>385 390 395 400 | 1200 |
| cgt tac ctt ggt aac cgg ctg ctg acc ccc act gat acg cct gag tgg<br>Arg Tyr Leu Gly Asn Arg Leu Leu Thr Pro Thr Asp Thr Pro Glu Trp<br>405 410 415 | 1248 |
| ctg tct ttt gac gtc act gga gtt gta cgg cag tgg ctg aac caa gga<br>Leu Ser Phe Asp Val Thr Gly Val Val Arg Gln Trp Leu Asn Gln Gly<br>420 425 430 | 1296 |
| gac gga ata cag ggc ttt cga ttc agc gct cac tgc tct tgt gac agc<br>Asp Gly Ile Gln Gly Phe Arg Phe Ser Ala His Cys Ser Cys Asp Ser<br>435 440 445 | 1344 |
| aaa gat aac aaa ctc cac gtg gaa atc aac ggg atc agc ccc aaa cgt<br>Lys Asp Asn Lys Leu His Val Glu Ile Asn Gly Ile Ser Pro Lys Arg<br>450 455 460 | 1392 |
| cgg ggc gac ctg ggc acc atc cat gac atg aac cgg ccc ttc ctg ctc<br>Arg Gly Asp Leu Gly Thr Ile His Asp Met Asn Arg Pro Phe Leu Leu<br>465 470 475 480 | 1440 |
| ctc atg gcc acc ccc ctg gaa agg gcc cag cac ctg cac agc ctg cag<br>Leu Met Ala Thr Pro Leu Glu Arg Ala Gln His Leu His Ser Leu Gln<br>485 490 495 | 1488 |
| ggg gga ggc ggt tcc ccg ctc ggg ctt tgg gcg gga ggg ggc tca gcg<br>Gly Gly Gly Gly Ser Pro Leu Gly Leu Trp Ala Gly Gly Gly Ser Ala<br>500 505 510 | 1536 |
| gcc gca atc aac tat aag cag ctc cag ctc caa gaa agg acg aac att<br>Ala Ala Ile Asn Tyr Lys Gln Leu Gln Leu Gln Glu Arg Thr Asn Ile<br>515 520 525 | 1584 |
| cgg aaa tgt cag gag ctc ctg gag cag ctg aat gga aag atc aac ctc<br>Arg Lys Cys Gln Glu Leu Leu Glu Gln Leu Asn Gly Lys Ile Asn Leu<br>530 535 540 | 1632 |
| acc tac agg gcg gac ttc aag atc cct atg gag atg acg gag aag atg<br>Thr Tyr Arg Ala Asp Phe Lys Ile Pro Met Glu Met Thr Glu Lys Met<br>545 550 555 560 | 1680 |

```
cag aag agt tac act gcc ttt gcc atc caa gag atg ctc cag aat gtc      1728
Gln Lys Ser Tyr Thr Ala Phe Ala Ile Gln Glu Met Leu Gln Asn Val
            565                 570                 575 ttt ctt gtc ttc aga aac aat ttc tcc agc act ggg tgg aat gag act      1776
Phe Leu Val Phe Arg Asn Asn Phe Ser Ser Thr Gly Trp Asn Glu Thr
            580                 585                 590 att gtt gta cgt ctc ctg gat gaa ctc cac cag cag aca gtg ttt ctg      1824
Ile Val Val Arg Leu Leu Asp Glu Leu His Gln Gln Thr Val Phe Leu
            595                 600                 605 aag aca gta cta gag gaa aag caa gag gaa aga ttg acg tgg gag atg      1872
Lys Thr Val Leu Glu Glu Lys Gln Glu Glu Arg Leu Thr Trp Glu Met
            610                 615                 620 tcc tca act gct ctc cac ttg aag agc tat tac tgg agg gtg caa agg      1920
Ser Ser Thr Ala Leu His Leu Lys Ser Tyr Tyr Trp Arg Val Gln Arg
625                 630                 635                 640 tac ctt aaa ctc atg aag tac aac agc tac gcc tgg atg gtg gtc cga      1968
Tyr Leu Lys Leu Met Lys Tyr Asn Ser Tyr Ala Trp Met Val Val Arg
            645                 650                 655 gca gag atc ttc agg aac ttt ctc atc att cga aga ctt acc aga aac      2016
Ala Glu Ile Phe Arg Asn Phe Leu Ile Ile Arg Arg Leu Thr Arg Asn
            660                 665                 670 ttc caa aac tga atctagacc                                            2037
Phe Gln Asn
    675

<210> SEQ ID NO 131
<211> LENGTH: 675
<212> TYPE: PRT
<213> ORGANISM: Artificial sequence
<220> FEATURE:
<223> OTHER INFORMATION: Synthetic Construct

<400> SEQUENCE: 131

Gly Ser Thr Met Tyr Arg Met Gln Leu Leu Cys Ile Ala Leu Ser Leu
1               5                   10                  15

Ala Leu Val Thr Asn Ser Gly Cys Lys Pro Cys Ile Cys Thr Val Pro
            20                  25                  30

Glu Val Ser Ser Val Phe Ile Phe Pro Pro Lys Pro Lys Asp Val Leu
        35                  40                  45

Thr Ile Thr Leu Thr Pro Lys Val Thr Cys Val Val Val Asp Ile Ser
    50                  55                  60

Lys Asp Asp Pro Glu Val Gln Phe Ser Trp Phe Val Asp Asp Val Glu
65                  70                  75                  80

Val His Thr Ala Gln Thr Gln Pro Arg Glu Glu Gln Phe Asn Ser Thr
                85                  90                  95

Phe Arg Ser Val Ser Glu Leu Pro Ile Met His Gln Asp Trp Leu Asn
            100                 105                 110

Gly Lys Glu Phe Lys Cys Arg Val Asn Ser Ala Ala Phe Pro Ala Pro
        115                 120                 125

Ile Glu Lys Thr Ile Ser Lys Thr Lys Gly Arg Pro Lys Ala Pro Gln
    130                 135                 140

Val Tyr Thr Ile Pro Pro Pro Lys Glu Gln Met Ala Lys Asp Lys Val
145                 150                 155                 160

Ser Leu Thr Cys Met Ile Thr Asp Phe Phe Pro Glu Asp Ile Thr Val
                165                 170                 175

Glu Trp Gln Trp Asn Gly Gln Pro Ala Glu Asn Tyr Lys Asn Thr Gln
            180                 185                 190
```

```
Pro Ile Met Asp Thr Asp Gly Ser Tyr Phe Val Tyr Ser Lys Leu Asn
        195                 200                 205
Val Gln Lys Ser Asn Trp Glu Ala Gly Asn Thr Phe Thr Cys Ser Val
210                 215                 220
Leu His Glu Gly Leu His Asn His His Thr Glu Lys Ser Leu Ser His
225                 230                 235                 240
Ser Pro Gly Lys Lys Leu Pro Trp Arg Asn Ser Ser Thr Ser Lys Thr
                245                 250                 255
Ile Asp Met Glu Leu Val Lys Arg Lys Arg Ile Glu Ala Ile Arg Gly
            260                 265                 270
Gln Ile Leu Ser Lys Leu Arg Leu Ala Ser Pro Ser Gln Gly Glu
        275                 280                 285
Val Pro Pro Gly Pro Leu Pro Glu Ala Val Leu Ala Leu Tyr Asn Ser
    290                 295                 300
Thr Arg Asp Arg Val Ala Gly Glu Ser Ala Asp Pro Glu Pro Glu Pro
305                 310                 315                 320
Glu Ala Asp Tyr Tyr Ala Lys Glu Val Thr Arg Val Leu Met Val Asp
                325                 330                 335
Arg Asn Asn Ala Ile Tyr Glu Lys Thr Lys Asp Ile Ser His Ser Ile
            340                 345                 350
Tyr Met Phe Phe Asn Thr Ser Asp Ile Arg Glu Ala Val Pro Glu Pro
        355                 360                 365
Pro Leu Leu Ser Arg Ala Glu Leu Arg Leu Gln Arg Leu Lys Ser Ser
    370                 375                 380
Val Glu Gln His Val Glu Leu Tyr Gln Lys Tyr Ser Asn Asn Ser Trp
385                 390                 395                 400
Arg Tyr Leu Gly Asn Arg Leu Leu Thr Pro Thr Asp Thr Pro Glu Trp
                405                 410                 415
Leu Ser Phe Asp Val Thr Gly Val Val Arg Gln Trp Leu Asn Gln Gly
            420                 425                 430
Asp Gly Ile Gln Gly Phe Arg Phe Ser Ala His Cys Ser Cys Asp Ser
        435                 440                 445
Lys Asp Asn Lys Leu His Val Glu Ile Asn Gly Ile Ser Pro Lys Arg
450                 455                 460
Arg Gly Asp Leu Gly Thr Ile His Asp Met Asn Arg Pro Phe Leu Leu
465                 470                 475                 480
Leu Met Ala Thr Pro Leu Glu Arg Ala Gln His Leu His Ser Leu Gln
                485                 490                 495
Gly Gly Gly Gly Ser Pro Leu Gly Leu Trp Ala Gly Gly Ser Ala
            500                 505                 510
Ala Ala Ile Asn Tyr Lys Gln Leu Gln Leu Gln Glu Arg Thr Asn Ile
        515                 520                 525
Arg Lys Cys Gln Glu Leu Leu Glu Gln Leu Asn Gly Lys Ile Asn Leu
    530                 535                 540
Thr Tyr Arg Ala Asp Phe Lys Ile Pro Met Glu Met Thr Glu Lys Met
545                 550                 555                 560
Gln Lys Ser Tyr Thr Ala Phe Ala Ile Gln Glu Met Leu Gln Asn Val
                565                 570                 575
Phe Leu Val Phe Arg Asn Asn Phe Ser Ser Thr Gly Trp Asn Glu Thr
            580                 585                 590
Ile Val Val Arg Leu Leu Asp Glu Leu His Gln Gln Thr Val Phe Leu
        595                 600                 605
Lys Thr Val Leu Glu Glu Lys Gln Glu Glu Arg Leu Thr Trp Glu Met
```

```
                610                615                620
Ser Ser Thr Ala Leu His Leu Lys Ser Tyr Tyr Trp Arg Val Gln Arg
625                630                635                640

Tyr Leu Lys Leu Met Lys Tyr Asn Ser Tyr Ala Trp Met Val Val Arg
                645                650                655

Ala Glu Ile Phe Arg Asn Phe Leu Ile Ile Arg Arg Leu Thr Arg Asn
                660                665                670

Phe Gln Asn
        675

<210> SEQ ID NO 132
<211> LENGTH: 2370
<212> TYPE: DNA
<213> ORGANISM: Artificial sequence
<220> FEATURE:
<223> OTHER INFORMATION: Synthetic sequence: Human lg Lap with anti-
      herNeu2 (Herceptin) antibody
<220> FEATURE:
<221> NAME/KEY: CDS
<222> LOCATION: (1)..(2370)

<400> SEQUENCE: 132 atg tac agg atg caa ctc ctg tct tgc att gca cta agt ctt gca ctt    48
Met Tyr Arg Met Gln Leu Leu Ser Cys Ile Ala Leu Ser Leu Ala Leu
1               5                   10                  15 gtc acg aat tcc gag ccc aaa tct tgt gac aaa act cac aca tgc cca    96
Val Thr Asn Ser Glu Pro Lys Ser Cys Asp Lys Thr His Thr Cys Pro
                20                  25                  30 ccg tgc cca gca cct gaa gct gcg ggg gga ccg tca gtc ttc ctc ttc   144
Pro Cys Pro Ala Pro Glu Ala Ala Gly Gly Pro Ser Val Phe Leu Phe
            35                  40                  45 ccc cca aaa ccc aag gac acc ctc atg atc tcc cgg acc cct gag gtc   192
Pro Pro Lys Pro Lys Asp Thr Leu Met Ile Ser Arg Thr Pro Glu Val
        50                  55                  60 aca tgc gtg gtg gtg gac gtg agc cac gaa gac cct gag gtc aag ttc   240
Thr Cys Val Val Val Asp Val Ser His Glu Asp Pro Glu Val Lys Phe
65                  70                  75                  80 aac tgg tac gtg gac ggc gtg gag gtg cat aat gcc aag aca aag ccg   288
Asn Trp Tyr Val Asp Gly Val Glu Val His Asn Ala Lys Thr Lys Pro
                85                  90                  95 cgg gag gag cag tac aac agc acg tac cgt gtg gtc agc gtc ctc acc   336
Arg Glu Glu Gln Tyr Asn Ser Thr Tyr Arg Val Val Ser Val Leu Thr
                100                 105                 110 gtc ctg cac cag gac tgg ctg aat ggc aag gag tac aag tgc aag gtc   384
Val Leu His Gln Asp Trp Leu Asn Gly Lys Glu Tyr Lys Cys Lys Val
            115                 120                 125 tcc aac aaa gcc ctc cca gcc ccc atc gag aaa acc atc tcc aaa gcc   432
Ser Asn Lys Ala Leu Pro Ala Pro Ile Glu Lys Thr Ile Ser Lys Ala
        130                 135                 140 aaa ggg cag ccc cga gaa cca cag gtg tac acc ctg ccc cca tcc cgg   480
Lys Gly Gln Pro Arg Glu Pro Gln Val Tyr Thr Leu Pro Pro Ser Arg
145                 150                 155                 160 gag gag atg acc aag aac cag gtc agc ctg acc tgc ctg gtc aaa ggc   528
Glu Glu Met Thr Lys Asn Gln Val Ser Leu Thr Cys Leu Val Lys Gly
                165                 170                 175 ttc tat ccc agc gac atc gcc gtg gag tgg gag agc aat ggg cag ccg   576
Phe Tyr Pro Ser Asp Ile Ala Val Glu Trp Glu Ser Asn Gly Gln Pro
                180                 185                 190 gag aac aac tac aag acc acg cct ccc gtg ctg gac tcc gac ggc tcc   624
Glu Asn Asn Tyr Lys Thr Thr Pro Pro Val Leu Asp Ser Asp Gly Ser
            195                 200                 205
```

| | | |
|---|---|---|
| ttc ttc ctc tat agc aag ctc acc gtg gac aag agc agg tgg cag cag<br>Phe Phe Leu Tyr Ser Lys Leu Thr Val Asp Lys Ser Arg Trp Gln Gln<br>210                           215                    220 | | 672 |
| ggg aac gtc ttc tca tgc tcc gtg atg cat gag gct ctg cac aac cac<br>Gly Asn Val Phe Ser Cys Ser Val Met His Glu Ala Leu His Asn His<br>225                    230                  235                  240 | | 720 |
| tac acg cag aag agc ctc tcc ctg tct ccg ggt aaa aag ctt cca tgg<br>Tyr Thr Gln Lys Ser Leu Ser Leu Ser Pro Gly Lys Lys Leu Pro Trp<br>                      245                  250                  255 | | 768 |
| agg aat tcc cta tcc acc agt aag act atc gac atg gag ctg gtg aag<br>Arg Asn Ser Leu Ser Thr Ser Lys Thr Ile Asp Met Glu Leu Val Lys<br>                260                  265                  270 | | 816 |
| cgg aag cgc atc gag gcc atc cgc ggc cag atc ctg tcc aag ctg cgg<br>Arg Lys Arg Ile Glu Ala Ile Arg Gly Gln Ile Leu Ser Lys Leu Arg<br>      275                  280                  285 | | 864 |
| ctc gcc agc ccc ccg agc cag ggg gag gtg ccg ccc ggc ccg ctg ccc<br>Leu Ala Ser Pro Pro Ser Gln Gly Glu Val Pro Pro Gly Pro Leu Pro<br>290                           295                  300 | | 912 |
| gag gcc gtg ctc gcc ctg tac aac agc acc cgc gac cgg gtg gcc ggg<br>Glu Ala Val Leu Ala Leu Tyr Asn Ser Thr Arg Asp Arg Val Ala Gly<br>305                       310                  315                  320 | | 960 |
| gag agt gca gaa ccg gag ccc gag cct gag gcc gac tac tac gcc aag<br>Glu Ser Ala Glu Pro Glu Pro Glu Pro Glu Ala Asp Tyr Tyr Ala Lys<br>                         325                  330                  335 | | 1008 |
| gag gtc acc cgc gtg cta atg gtg gaa acc cac aac gaa atc tat gac<br>Glu Val Thr Arg Val Leu Met Val Glu Thr His Asn Glu Ile Tyr Asp<br>                  340                  345                  350 | | 1056 |
| aag ttc aag cag agt aca cac agc ata tat atg ttc ttc aac aca tca<br>Lys Phe Lys Gln Ser Thr His Ser Ile Tyr Met Phe Phe Asn Thr Ser<br>      355                  360                  365 | | 1104 |
| gag ctc cga gaa gcg gta cct gaa ccc gtg ttg ctc tcc cgg gca gag<br>Glu Leu Arg Glu Ala Val Pro Glu Pro Val Leu Leu Ser Arg Ala Glu<br>370                           375                  380 | | 1152 |
| ctg cgt ctg ctg agg ctc aag tta aaa gtg gag cag cac gtg gag ctg<br>Leu Arg Leu Leu Arg Leu Lys Leu Lys Val Glu Gln His Val Glu Leu<br>385                       390                  395                  400 | | 1200 |
| tac cag aaa tac agc aac aat tcc tgg cga tac ctc agc aac cgg ctg<br>Tyr Gln Lys Tyr Ser Asn Asn Ser Trp Arg Tyr Leu Ser Asn Arg Leu<br>                      405                  410                  415 | | 1248 |
| ctg gca ccc agc gac tcg cca gag tgg tta tct ttt gat gtc acc gga<br>Leu Ala Pro Ser Asp Ser Pro Glu Trp Leu Ser Phe Asp Val Thr Gly<br>                  420                  425                  430 | | 1296 |
| gtt gtg cgg cag tgg ttg agc cgt gga ggg gaa att gag ggc ttt cgc<br>Val Val Arg Gln Trp Leu Ser Arg Gly Gly Glu Ile Glu Gly Phe Arg<br>      435                  440                  445 | | 1344 |
| ctt agc gcc cac tgc tcc tgt gac agc agg gat aac aca ctg caa gtg<br>Leu Ser Ala His Cys Ser Cys Asp Ser Arg Asp Asn Thr Leu Gln Val<br>450                           455                  460 | | 1392 |
| gac atc aac ggg ttc act acc ggc cgc cga ggt gac ctg gcc acc att<br>Asp Ile Asn Gly Phe Thr Thr Gly Arg Arg Gly Asp Leu Ala Thr Ile<br>465                       470                  475                  480 | | 1440 |
| cat ggc atg aac cgg cct ttc ctg ctt ctc atg gcc acc ccg ctg gag<br>His Gly Met Asn Arg Pro Phe Leu Leu Leu Met Ala Thr Pro Leu Glu<br>                       485                  490                  495 | | 1488 |
| agg gcc cag cat ctg caa agc ctg cag gga ggc ggg gtt tca gac gtc<br>Arg Ala Gln His Leu Gln Ser Leu Gln Gly Gly Gly Val Ser Asp Val<br>                  500                  505                  510 | | 1536 |
| caa gag ttc cgc ggc gtc aca gct gtg atc cgt gga ggc ggg ggt tca<br>Gln Glu Phe Arg Gly Val Thr Ala Val Ile Arg Gly Gly Gly Gly Ser | | 1584 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 515 |     |     |     |     | 520 |     |     |     |     |     | 525 |     |     |      |
| gcg | gcc | cag | atg | gcc | gag | gtt | cag | ctg | gtg | gag | tct | ggc | ggt | ggc | ctg | 1632 |
| Ala | Ala | Gln | Met | Ala | Glu | Val | Gln | Leu | Val | Glu | Ser | Gly | Gly | Gly | Leu |      |
|     | 530 |     |     |     |     | 535 |     |     |     |     | 540 |     |     |     |     |      |
| gtg | cag | cca | ggg | ggc | tca | ctc | cgt | ttg | tcc | tgt | gca | gct | tct | ggc | ttc | 1680 |
| Val | Gln | Pro | Gly | Gly | Ser | Leu | Arg | Leu | Ser | Cys | Ala | Ala | Ser | Gly | Phe |      |
| 545 |     |     |     |     | 550 |     |     |     |     | 555 |     |     |     |     | 560 |      |
| aac | att | aaa | gac | acc | tat | ata | cac | tgg | gtg | cgt | cag | gcc | ccg | ggt | aag | 1728 |
| Asn | Ile | Lys | Asp | Thr | Tyr | Ile | His | Trp | Val | Arg | Gln | Ala | Pro | Gly | Lys |      |
|     |     |     |     | 565 |     |     |     |     | 570 |     |     |     |     | 575 |     |      |
| ggc | ctg | gaa | tgg | gtt | gca | agg | att | tat | cct | acg | aat | ggt | tat | gct | aga | 1776 |
| Gly | Leu | Glu | Trp | Val | Ala | Arg | Ile | Tyr | Pro | Thr | Asn | Gly | Tyr | Ala | Arg |      |
|     |     |     | 580 |     |     |     |     | 585 |     |     |     |     | 590 |     |     |      |
| tat | gcc | gat | agc | gtc | aag | ggc | cgt | ttc | act | ata | agc | gca | gac | aca | tcc | 1824 |
| Tyr | Ala | Asp | Ser | Val | Lys | Gly | Arg | Phe | Thr | Ile | Ser | Ala | Asp | Thr | Ser |      |
|     |     | 595 |     |     |     |     | 600 |     |     |     |     | 605 |     |     |     |      |
| aaa | aac | aca | gcc | tac | ctg | cag | atg | aac | agc | ctg | cgt | gct | gag | gac | act | 1872 |
| Lys | Asn | Thr | Ala | Tyr | Leu | Gln | Met | Asn | Ser | Leu | Arg | Ala | Glu | Asp | Thr |      |
|     | 610 |     |     |     |     | 615 |     |     |     |     | 620 |     |     |     |     |      |
| gcc | gtc | tat | tat | tgt | tct | aga | tgg | gga | ggg | gac | ggc | ttc | tat | gct | atg | 1920 |
| Ala | Val | Tyr | Tyr | Cys | Ser | Arg | Trp | Gly | Gly | Asp | Gly | Phe | Tyr | Ala | Met |      |
| 625 |     |     |     |     | 630 |     |     |     |     | 635 |     |     |     |     | 640 |      |
| gac | tac | tgg | ggt | caa | gga | acc | ctg | gtc | acc | gtc | tcc | tcg | ggc | gga | ggc | 1968 |
| Asp | Tyr | Trp | Gly | Gln | Gly | Thr | Leu | Val | Thr | Val | Ser | Ser | Gly | Gly | Gly |      |
|     |     |     |     | 645 |     |     |     |     | 650 |     |     |     |     | 655 |     |      |
| gga | tcc | ggc | gga | ggc | gga | tcg | gga | ggc | gga | tcc | gat | atc | cag | atg | 2016 |
| Gly | Ser | Gly | Gly | Gly | Gly | Ser | Gly | Gly | Gly | Ser | Asp | Ile | Gln | Met |      |
|     |     |     | 660 |     |     |     |     | 665 |     |     |     |     | 670 |     |     |      |
| acc | cag | tcc | ccg | agc | tcc | ctg | tcc | gcc | tct | gtg | ggc | gat | agg | gtc | acc | 2064 |
| Thr | Gln | Ser | Pro | Ser | Ser | Leu | Ser | Ala | Ser | Val | Gly | Asp | Arg | Val | Thr |      |
|     |     | 675 |     |     |     |     | 680 |     |     |     |     | 685 |     |     |     |      |
| atc | acc | tgc | cgt | gcc | agt | cag | gat | gtg | aat | act | gct | gta | gcc | tgg | tat | 2112 |
| Ile | Thr | Cys | Arg | Ala | Ser | Gln | Asp | Val | Asn | Thr | Ala | Val | Ala | Trp | Tyr |      |
|     | 690 |     |     |     |     | 695 |     |     |     |     | 700 |     |     |     |     |      |
| caa | cag | aaa | cca | gga | aaa | gct | ccg | aaa | cta | ctg | att | tac | tcg | gca | tcc | 2160 |
| Gln | Gln | Lys | Pro | Gly | Lys | Ala | Pro | Lys | Leu | Leu | Ile | Tyr | Ser | Ala | Ser |      |
| 705 |     |     |     |     | 710 |     |     |     |     | 715 |     |     |     |     | 720 |      |
| ttc | ctc | tac | tct | gga | gtc | ctt | tct | cgc | ttc | tct | ggg | tcc | aga | tct | ggg | 2208 |
| Phe | Leu | Tyr | Ser | Gly | Val | Leu | Ser | Arg | Phe | Ser | Gly | Ser | Arg | Ser | Gly |      |
|     |     |     |     | 725 |     |     |     |     | 730 |     |     |     |     | 735 |     |      |
| acg | gat | ttc | act | ctg | acc | atc | agc | agt | ctg | cag | ccg | gag | gac | ttc | gca | 2256 |
| Thr | Asp | Phe | Thr | Leu | Thr | Ile | Ser | Ser | Leu | Gln | Pro | Glu | Asp | Phe | Ala |      |
|     |     |     | 740 |     |     |     |     | 745 |     |     |     |     | 750 |     |     |      |
| act | tat | tac | tgt | cag | caa | cat | tat | act | act | cct | ccc | acg | ttc | gga | cag | 2304 |
| Thr | Tyr | Tyr | Cys | Gln | Gln | His | Tyr | Thr | Thr | Pro | Pro | Thr | Phe | Gly | Gln |      |
|     |     | 755 |     |     |     |     | 760 |     |     |     |     | 765 |     |     |     |      |
| ggt | acc | aag | gtg | gag | atc | aaa | cgc | gcg | gat | gcg | gcc | gca | ctc | gag | cac | 2352 |
| Gly | Thr | Lys | Val | Glu | Ile | Lys | Arg | Ala | Asp | Ala | Ala | Ala | Leu | Glu | His |      |
| 770 |     |     |     |     | 775 |     |     |     |     | 780 |     |     |     |     |     |      |
| cac | cac | cac | cac | cac | tga |     |     |     |     |     |     |     |     |     |     | 2370 |
| His | His | His | His | His |     |     |     |     |     |     |     |     |     |     |     |      |
| 785 |     |     |     |     |     |     |     |     |     |     |     |     |     |     |     |      |

<210> SEQ ID NO 133
<211> LENGTH: 789
<212> TYPE: PRT
<213> ORGANISM: Artificial sequence
<220> FEATURE:
<223> OTHER INFORMATION: Synthetic Construct

<400> SEQUENCE: 133

```
Met Tyr Arg Met Gln Leu Leu Ser Cys Ile Ala Leu Ser Leu Ala Leu
1               5                   10                  15

Val Thr Asn Ser Glu Pro Lys Ser Cys Asp Lys Thr His Thr Cys Pro
            20                  25                  30

Pro Cys Pro Ala Pro Glu Ala Ala Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Lys Leu Pro Trp
                245                 250                 255

Arg Asn Ser Leu Ser Thr Ser Lys Thr Ile Asp Met Glu Leu Val Lys
            260                 265                 270

Arg Lys Arg Ile Glu Ala Ile Arg Gly Gln Ile Leu Ser Lys Leu Arg
            275                 280                 285

Leu Ala Ser Pro Pro Ser Gln Gly Glu Val Pro Pro Gly Pro Leu Pro
290                 295                 300

Glu Ala Val Leu Ala Leu Tyr Asn Ser Thr Arg Asp Arg Val Ala Gly
305                 310                 315                 320

Glu Ser Ala Glu Pro Glu Pro Glu Pro Glu Ala Asp Tyr Tyr Ala Lys
                325                 330                 335

Glu Val Thr Arg Val Leu Met Val Glu Thr His Asn Glu Ile Tyr Asp
            340                 345                 350

Lys Phe Lys Gln Ser Thr His Ser Ile Tyr Met Phe Phe Asn Thr Ser
            355                 360                 365

Glu Leu Arg Glu Ala Val Pro Glu Pro Val Leu Leu Ser Arg Ala Glu
        370                 375                 380

Leu Arg Leu Leu Arg Leu Lys Leu Lys Val Glu Gln His Val Glu Leu
385                 390                 395                 400

Tyr Gln Lys Tyr Ser Asn Asn Ser Trp Arg Tyr Leu Ser Asn Arg Leu
                405                 410                 415
```

```
Leu Ala Pro Ser Asp Ser Pro Glu Trp Leu Ser Phe Asp Val Thr Gly
                420                 425                 430

Val Val Arg Gln Trp Leu Ser Arg Gly Gly Glu Ile Glu Gly Phe Arg
            435                 440                 445

Leu Ser Ala His Cys Ser Cys Asp Ser Arg Asp Asn Thr Leu Gln Val
        450                 455                 460

Asp Ile Asn Gly Phe Thr Thr Gly Arg Arg Gly Asp Leu Ala Thr Ile
465                 470                 475                 480

His Gly Met Asn Arg Pro Phe Leu Leu Met Ala Thr Pro Leu Glu
                485                 490                 495

Arg Ala Gln His Leu Gln Ser Leu Gln Gly Gly Gly Ser Asp Val
                500                 505                 510

Gln Glu Phe Arg Gly Val Thr Ala Val Ile Arg Gly Gly Gly Ser
            515                 520                 525

Ala Ala Gln Met Ala Glu Val Gln Leu Val Glu Ser Gly Gly Gly Leu
        530                 535                 540

Val Gln Pro Gly Gly Ser Leu Arg Leu Ser Cys Ala Ala Ser Gly Phe
545                 550                 555                 560

Asn Ile Lys Asp Thr Tyr Ile His Trp Val Arg Gln Ala Pro Gly Lys
                565                 570                 575

Gly Leu Glu Trp Val Ala Arg Ile Tyr Pro Thr Asn Gly Tyr Ala Arg
            580                 585                 590

Tyr Ala Asp Ser Val Lys Gly Arg Phe Thr Ile Ser Ala Asp Thr Ser
        595                 600                 605

Lys Asn Thr Ala Tyr Leu Gln Met Asn Ser Leu Arg Ala Glu Asp Thr
610                 615                 620

Ala Val Tyr Tyr Cys Ser Arg Trp Gly Gly Asp Gly Phe Tyr Ala Met
625                 630                 635                 640

Asp Tyr Trp Gly Gln Gly Thr Leu Val Thr Val Ser Ser Gly Gly Gly
                645                 650                 655

Gly Ser Gly Gly Gly Gly Ser Gly Gly Gly Gly Ser Asp Ile Gln Met
            660                 665                 670

Thr Gln Ser Pro Ser Ser Leu Ser Ala Ser Val Gly Asp Arg Val Thr
        675                 680                 685

Ile Thr Cys Arg Ala Ser Gln Asp Val Asn Thr Ala Val Ala Trp Tyr
690                 695                 700

Gln Gln Lys Pro Gly Lys Ala Pro Lys Leu Leu Ile Tyr Ser Ala Ser
705                 710                 715                 720

Phe Leu Tyr Ser Gly Val Leu Ser Arg Phe Ser Gly Ser Arg Ser Gly
                725                 730                 735

Thr Asp Phe Thr Leu Thr Ile Ser Ser Leu Gln Pro Glu Asp Phe Ala
            740                 745                 750

Thr Tyr Tyr Cys Gln Gln His Tyr Thr Thr Pro Pro Thr Phe Gly Gln
        755                 760                 765

Gly Thr Lys Val Glu Ile Lys Arg Ala Asp Ala Ala Leu Glu His
770                 775                 780

His His His His
785

<210> SEQ ID NO 134
<211> LENGTH: 2370
<212> TYPE: DNA
<213> ORGANISM: Artificial sequence
<220> FEATURE:
<223> OTHER INFORMATION: Synthetic construct
```

<400> SEQUENCE: 134

```
tcagtggtgg tggtggtggt gctcgagtgc ggccgcatcc gcgcgtttga tctccacctt      60
ggtaccctgt ccgaacgtgg gaggagtagt ataatgttgc tgacagtaat aagttgcgaa     120
gtcctccggc tgcagactgc tgatggtcag agtgaaatcc gtcccagatc tggacccaga     180
gaagcgagaa aggactccag agtagaggaa ggatgccgag taaatcagta gtttcggagc     240
ttttcctggt ttctgttgat accaggctac agcagtattc acatcctgac tggcacggca     300
ggtgatggtg accctatcgc ccacagaggc ggacagggag ctcggggact gggtcatctg     360
gatatcggat cctccgcctc ccgatccgcc tccgccggat ccgcctccgc ccaggagac      420
ggtgaccagg gttccttgac cccagtagtc catagcatag aagccgtccc ctccccatct     480
agaacaataa tagacggcag tgtcctcagc acgcaggctg ttcatctgca ggtaggctgt     540
gtttttggat gtgtctgcgc ttatagtgaa acggcccttg acgctatcgg catatctagc     600
ataaccattc gtaggataaa tccttgcaac ccattccagg cccttacccg gggcctgacg     660
cacccagtgt atataggtgt ctttaatgtt gaagccagaa gctgcacagg acaaacggag     720
tgagccccct ggctgcacca ggccaccgcc agactccacc agctgaacct cggccatctg     780
ggccgctgaa cccccgcctc cacggatcac agctgtgacg ccgcggaact cttggacgtc     840
tgaaccccg cctccctgca ggctttgcag atgctgggcc ctctccagcg gggtggccat      900
gagaagcagg aaaggccggt tcatgccatg aatggtggcc aggtcacctc ggcggccggt     960
agtgaacccg ttgatgtcca cttgcagtgt gttatccctg ctgtcacagg agcagtgggc    1020
gctaaggcga aagccctcaa tttcccctcc acggctcaac cactgccgca caactccggt    1080
gacatcaaaa gataaccact ctggcgagtc gctgggtgcc agcagccggt tgctgaggta    1140
tcgccaggaa ttgttgctgt atttctggta cagctccacg tgctgctcca cttttaactt    1200
gagcctcagc agacgcagct ctgcccggga gcaacacg ggttcaggta ccgcttctcg      1260
gagctctgat gtgttgaaga acatatatat gctgtgtgta ctctgcttga acttgtcata    1320
gatttcgttg tgggttttcca ccattagcac gcgggtgacc tccttggcgt agtagtcggc   1380
ctcaggctcg ggctccggtt ctgcactctc cccgccacc cggtcgcggg tgctgttgta     1440
cagggcgagc acggcctcgg gcagcgggcc gggcggcacc tcccctggc tcgggggct      1500
ggcgagccgc agcttggaca ggatctggcc gcggatggcc tcgatgcgct tccgcttcac    1560
cagctccatg tcgatagtct tactggtgga tagggaattc ctccatggaa gctttttacc    1620
cggagacagg gagaggctct tctgcgtgta gtggttgtgc agagcctcat gcatcacgga    1680
gcatgagaag acgttcccct gctgccacct gctcttgtcc acggtgagct tgctatagag    1740
gaagaaggag ccgtcggagt ccagcacggg aggcgtggtc ttgtagttgt tctccggctg    1800
cccattgctc tcccactcca cggcgatgtc gctgggatag aagcctttga ccaggcaggt    1860
caggctgacc tggttcttgg tcatctcctc ccgggatggg ggcagggtgt acacctgtgg    1920
ttctcgggc tgccctttgg ctttggagat ggttttctcg atggggctg ggagggcttt       1980
gttggagacc ttgcacttgt actccttgcc attcagccag tcctggtgca ggacggtgag    2040
gacgctgacc acacggtacg tgctgttgta ctgctcctcc cgcggctttg tcttggcatt    2100
atgcacctcc acgccgtcca cgtaccagtt gaacttgacc tcagggtctt cgtggctcac    2160
gtccaccacc acgcatgtga cctcagggggt ccggagatc atgagggtgt ccttgggttt    2220
tggggggaag aggaagactg acggtccccc cgcagcttca ggtgctgggc acggtgggca    2280
```

```
tgtgtgagtt ttgtcacaag atttgggctc ggaattcgtg acaagtgcaa gacttagtgc    2340
aatgcaagac aggagttgca tcctgtacat                                     2370
```

<210> SEQ ID NO 135
<211> LENGTH: 5
<212> TYPE: PRT
<213> ORGANISM: Artificial sequence
<220> FEATURE:
<223> OTHER INFORMATION: Synthetic sequence: Linker

<400> SEQUENCE: 135

Gly Gly Gly Gly Ser
1               5

<210> SEQ ID NO 136
<211> LENGTH: 15
<212> TYPE: PRT
<213> ORGANISM: Artificial sequence
<220> FEATURE:
<223> OTHER INFORMATION: Synthetic sequence: Linker

<400> SEQUENCE: 136

Gly Gly Gly Gly Ser Gly Gly Gly Gly Ser Gly Gly Gly Gly Ser
1               5                   10                  15

<210> SEQ ID NO 137
<211> LENGTH: 5
<212> TYPE: PRT
<213> ORGANISM: Artificial sequence
<220> FEATURE:
<223> OTHER INFORMATION: Common sequence motif present in hinge
      polypeptide region
<220> FEATURE:
<221> NAME/KEY: VARIANT
<222> LOCATION: (3)..(3)
<223> OTHER INFORMATION: Xaa can be another residue that does not
      interfere with dimerisation, for example proline (P), arginine (R)
      or serine (S)

<400> SEQUENCE: 137

Cys Pro Xaa Cys Pro
1               5

<210> SEQ ID NO 138
<211> LENGTH: 15
<212> TYPE: PRT
<213> ORGANISM: Homo sapiens

<400> SEQUENCE: 138

Glu Pro Lys Ser Cys Asp Lys Thr His Thr Cys Pro Pro Cys Pro
1               5                   10                  15

<210> SEQ ID NO 139
<211> LENGTH: 12
<212> TYPE: PRT
<213> ORGANISM: Homo sapiens

<400> SEQUENCE: 139

Glu Arg Lys Cys Cys Val Glu Cys Pro Pro Cys Pro
1               5                   10

<210> SEQ ID NO 140
<211> LENGTH: 17
<212> TYPE: PRT
<213> ORGANISM: Homo sapiens

<400> SEQUENCE: 140

-continued

```
Glu Leu Lys Thr Pro Leu Gly Asp Thr Thr His Thr Cys Pro Arg Cys
1               5                   10                  15

Pro

<210> SEQ ID NO 141
<211> LENGTH: 15
<212> TYPE: PRT
<213> ORGANISM: Homo sapiens

<400> SEQUENCE: 141

Glu Pro Lys Ser Cys Asp Thr Pro Pro Pro Cys Pro Arg Cys Pro
1               5                   10                  15

<210> SEQ ID NO 142
<211> LENGTH: 12
<212> TYPE: PRT
<213> ORGANISM: Homo sapiens

<400> SEQUENCE: 142

Glu Ser Lys Tyr Gly Pro Pro Cys Pro Ser Cys Pro
1               5                   10

<210> SEQ ID NO 143
<211> LENGTH: 27
<212> TYPE: DNA
<213> ORGANISM: Artificial sequence
<220> FEATURE:
<223> OTHER INFORMATION: Synthetic primer

<400> SEQUENCE: 143
atgaattccg gttgtaagcc ttgcata                                          27

<210> SEQ ID NO 144
<211> LENGTH: 43
<212> TYPE: DNA
<213> ORGANISM: Artificial sequence
<220> FEATURE:
<223> OTHER INFORMATION: Synthetic primer

<400> SEQUENCE: 144
gtgaattcct ccatggaagc tttttaccag gagagtggga gag                        43
```